US010865412B2

(12) United States Patent
Liu et al.

(10) Patent No.: US 10,865,412 B2
(45) Date of Patent: Dec. 15, 2020

(54) THERAPEUTICS TARGETING IGFBP7 FOR THE TREATMENT OR PREVENTION OF HEART FAILURE AND METABOLIC DISEASES

(71) Applicant: Ottawa Heart Institute Research Corporation, Ottawa (CA)

(72) Inventors: Peter Liu, Ottawa (CA); Liyong Zhang, Ottawa (CA)

(73) Assignee: Ottawa Heart Institute Research, Ottawa (CA)

( * ) Notice: Subject to any disclaimer, the term of this patent is extended or adjusted under 35 U.S.C. 154(b) by 0 days.

(21) Appl. No.: 15/803,453

(22) Filed: Nov. 3, 2017

(65) Prior Publication Data

US 2018/0127752 A1  May 10, 2018

Related U.S. Application Data

(60) Provisional application No. 62/418,038, filed on Nov. 4, 2016.

(51) Int. Cl.

| | | |
|---|---|---|
| *C12N 15/113* | (2010.01) | |
| *A61K 31/713* | (2006.01) | |
| *A61K 39/395* | (2006.01) | |
| *C07K 16/18* | (2006.01) | |
| *A61K 31/365* | (2006.01) | |
| *G01N 33/50* | (2006.01) | |
| *G01N 33/68* | (2006.01) | |

(52) U.S. Cl.
CPC .......... *C12N 15/113* (2013.01); *A61K 31/365* (2013.01); *A61K 31/713* (2013.01); *A61K 39/3955* (2013.01); *C07K 16/18* (2013.01); *G01N 33/5061* (2013.01); *G01N 33/6896* (2013.01); *C07K 2317/76* (2013.01); *C12N 2310/14* (2013.01); *G01N 2333/4745* (2013.01)

(58) Field of Classification Search
CPC  A01K 2207/05; C12N 15/113; A61K 31/713; A61K 39/3955
See application file for complete search history.

(56) References Cited

U.S. PATENT DOCUMENTS

| | | | |
|---|---|---|---|
| 2010/0035963 A1 | 2/2010 | Chajut et al. | |
| 2010/0285491 A1* | 11/2010 | Wienhues-Thelen | G01N 33/6893 435/7.1 |
| 2011/0059089 A1 | 3/2011 | Swagemakers et al. | |
| 2013/0004511 A1* | 1/2013 | Thorin | A61P 27/02 424/172.1 |

FOREIGN PATENT DOCUMENTS

| | | | | |
|---|---|---|---|---|
| WO | WO-0035473 A2 * | 6/2000 | ........... | C12Q 1/6883 |

OTHER PUBLICATIONS

Kim et al. Mol Endocrinol. Nov. 2008; 22(11): 2531-2543. (Year: 2008).*
Ock et al.Endocrinology. Jan. 2016; 157(1): 336-345 (Year: 2016).*
Lam et al. Molecular Therapy-Nucleic Acids 4, e252, pp. 1-20 (Year: 2015).*
Altschul et al. "Basic Local Alignment Search Tool." National Center for Biotechnology Information (1990). 8 pages.
Barroso et al. "Serum insulin-like growth factor-1 and its binding protein-7: potential novel biomarkers for heart failure with preserved ejection fraction." BMC Cardiovascular Disorders (2016). 9 pages.
Bennett et al. "RNA Targeting Therapeutics:Molecular Mechanisms of Antisense Oligonucleotides as a Therapeutic Platform." Pharmaceuticals, Inc. (2009). 37 pages.
Bhatia et al. "Outcome of Heart Failure with Preserved Ejection Fraction in a Population-Based Study." The New England Journal of Medicine (2006). 10 pages.
Campisi. "Aging, Cellular Senescence, and Cancer." Buck Institute for Research on Aging (2013). 24 pages.
Chatterjee et al. "Loss of Igfbp7 Causes Precocious Involution in Lactating Mouse Mammary Gland." Plos One Journal (2013). 15 pages.
Vollmann et al. "Biventricular Pacing Improves the Blunted Force—Frequency Relation Present During Univentricular Pacing in Patients With Heart Failure and Conduction Delay." Circulation (2006). 7 pages.
Dinh et al. "Serum insulin like growth factor-I and its binding protein-7: novel promising biomarker in heart failure with preserved ejection fraction." (2012). 1 page.
Gandhi et al. "Prognostic Usefulness of Insulin-Like Growth Factor-Binding Protein 7 in Heart Failure With Reduced Ejection Fraction:ANovel Biomarker ofMyocardialDiastolic Function?" The American Journal of Cardiology (2014). 7 pages.
Gandhi et al. "Insulin-Like Growth Factor-Binding Protein-7 as a Biomarker of Diastolic Dysfunction and Functional Capacity in Heart Failure With Preserved Ejection Fraction: Results From the RELAX Trial." JACC : Heart Failure, vol. 4 , No. 11 (2016). 10 pages.
Garcia-Prat et al. "Autophagy maintains stemness by preventing senescence." Nature (2016). 21 pages.
Gaynor et al. "RNA interference: a chemist's perspective." The Royal Society of Chemistry (2010). 16 pages.

(Continued)

*Primary Examiner* — Brian Whiteman
(74) *Attorney, Agent, or Firm* — Jeffrey G. Sheldon; Katherine B. Sales; Cislo & Thomas LLP

(57) ABSTRACT

Insulin-like growth factor-binding protein 7 (IGFBP7) has been identified herein as a therapeutic target for the treatment or prevention of heart diseases, metabolic diseases, and other related disease or conditions. IGFBP7 inhibitors having IGFBP7 expression and/or activity reducing properties are described herein. Treatment methods, and uses, relating to such IGFBP7 inhibitors for the treatment or prevention of heart failure, IGFBP7-related metabolic diseases, and related diseases or conditions are provided.

17 Claims, 51 Drawing Sheets

Specification includes a Sequence Listing.

(56) References Cited

OTHER PUBLICATIONS

Johmura et al. "Multiple facets of p53 in senescence induction and maintenance." Cancer Science on behalf of Japanese Cancer Association (2016). 6 pages.
Juliano et al. "The Chemistry and Biology of Oligonucleotide Conjugates." Accounts of Chemical Research (2012). 10 pages.
Kuba et al. "Impaired Heart Contractility in Apelin Gene-Deficient Mice Associated With Aging and Pressure Overload." American Heart Association, Inc. (2007). 11 pages.
Kuilman et al. "Oncogene-Induced Senescence Relayed by an Interleukin-Dependent Inflammatory Network." Elsevier Inc. (2008). 13 pages.
Li et al. "Dynamic Changes in Myocardial Matrix and Relevance to Disease: Translational Perspectives." Circulation Research (2014). 12 pages.
Li et al. "MicroRNA-mediated regulation of extracellular matrix formation modulates somatic cell reprogramming." Cold Spring Harbor Laboratory Press for the RNA Society (2014). 17 pages.
Li et al. "Emerging role of CCN family proteins in tumorigenesis and cancer metastasis (Review)." International Journal of Molecular Medicine 36: 1451-1463 (2015). 13 pages.
Methawasin et al. "Experimentally Increasing the Compliance of Titin Through RNA Binding Motif-20 (RBM20) Inhibition Improves Diastolic Function in a Mouse Model of Heart Failure With Preserved Ejection Fraction." Circulation (2016). 15 pages.
Nawathe et al. "Insulin-like growth factor axis in pregnancies affected by fetal growth disorders." Clinical Epigenetics (2016). 13 pages.
Nian et al. "Inflammatory Cytokines and Postmyocardial Infarction Remodeling." Circulation Research (2004). 11 pages.
Ouzounian et al. "Diastolic heart failure: mechanisms and controversies." Nature Clinical Practice: Cardiovascular Medicine (2008). 12 pages.
Schnelle et al. "Echocardiographic evaluation of diastolic function in mouse models of heart disease." Journal of Molecular and Cellular Cardiology (2018). 9 pages.
Liu et al. "Serum IGFBP7 levels associate with insulin resistance and the risk of metabolic syndrome in a Chinese population." Scientific Reports (2015). 7 pages.
Tedgui et I. "Cytokines in Atherosclerosis: Pathogenic and Regulatory Pathways." American Physiological Society (2006). 67 pages.
Tijssen et al. "Laboratory Techniques in Biochemistry and Molecular Biology—Hybridization with Nucleic Acid Probes, Part I." Department of Physiological Chemistry, University of Utrecht, The Netherlands (1993). 65 pages.
Tonnessen-Murray et al. "The Regulation of Cellular Functions by the p53 Protein: Cellular Senescence." Cold Spring Harbor Perspectives in Medicine (2017). 15 pages.
Watanabe et al. "Role of IGFBP7 in Diabetic Nephropathy: TGF-β1 Induces IGFBP7 via Smad2/4 in Human Renal Proximal Tubular Epithelial Cells." PLOS ONE (2016). 20 pages.
Wolchinsky et al. "Angiomodulin is required for cardiogenesis of embryonic stem cells and is maintained by a feedback loop network of p63 and Activin-A." Science Direct (2013). 11 pages.
Wood et al. "Diastolic Heart Failure: Progress, Treatment Challenges, and Prevention." Canadian Journal of Cardiology Symposium Review: Canadian Journal of Cardiology 27 (2011). 9 pages.
Yuan et al. "Recent advances of siRNA delivery by nanoparticles." Expert Opinion on Drug Delivery (2011). 17 pages.
Zhang et al. "HACE1-dependent protein degradation provides cardiac protection in response to haemodynamic stress." Nature Communications (2014). 14 pages.

\* cited by examiner

SEQ ID NO: 1:

Human IGFBP7 mRNA sequence, accession number NM 001553.2, transcript variant 1

```
ACTCGCGCCCTTGCCGCTGCCACCGCACCCCGCCATGGAGCGGCCGTCGCTGCGCGCCCTGCTCCTCGGC
GCCGCTGGGCTGCTGCTCCTGCTCCTGCCCCTCTCCTCTTCCTCCTCTTCGGACACCTGCGGCCCCTGCG
AGCCGGCCTCCTGCCCGCCCCTGCCCCCGCTGGGCTGCCTGCTGGGCGAGACCCGCGACGCGTGCGGCTG
CTGCCCTATGTGCGCCCGCGGCGAGGGCGAGCCGTGCGGGGGTGGCGGCGCCGGCAGGGGTACTGCGCG
CCGGGCATGGAGTGCGTGAAGAGCCGCAAGAGGCGGAAGGGTAAAGCCGGGGCAGCAGCCGGCGGTCCGG
GTGTAAGCGGCGTGTGCGTGTGCAAGAGCCGCTACCCGGTGTGCGGCAGCGACGGCACCACCTACCCGAG
CGGCTGCCAGCTGCGCGCCGCCAGCCAGAGGGCCGAGAGCCGCGGGGAGAAGGCCATCACCCAGGTCAGC
AAGGGCACCTGCGAGCAAGGTCCTTCCATAGTGACGCCCCCAAGGACATCTGGAATGTCACTGGTGCCC
AGGTGTACTTGAGCTGTGAGGTCATCGGAATCCCGACACCTGTCCTCATCTGGAACAAGGTAAAAGGGG
TCACTATGGAGTTCAAAGGACAGAACTCCTGCCTGGTGACCGGGACAACCTGGCCATTCAGACCCGGGGT
GGCCCAGAAAAGCATGAAGTAACTGGCTGGGTGCTGGTATCTCCTCTAAGTAAGGAAGATGCTGGAGAAT
ATGAGTGCCATGCATCCAATTCCCAAGGACAGGCTTCAGCATCAGCAAAAATTACAGTGGTTGATGCCTT
ACATGAAATACCAGTGAAAAAGGTGAAGGTGCCGAGCTATAAACCTCCAGAATATTATTAGTCTGCATG
GTTAAAAGTAGTCATGGATAACTACATTACCTGTTCTTGCCTAATAAGTTTCTTTTAATCCAATCCACTA
ACACTTTAGTTATATTCACTGGTTTTACACAGAGAAATACAAAATAAAGATCACACATCAAGACTATCTA
CAAAAATTTATTATATATTTACAGAAGAAAAGCATGCATATCATTAAACAAATAAAATACTTTTTATCAC
AACACAGTAAAAAAAAA
```

Figure 1A

SEQ ID NO: 2:

Human IGFBP7 mRNA sequence, accession number NM 001253835.1, transcript variant 2

ACTCGCGCCCTTGCCGCTGCCACCGCACCCGCCATGGAGCGGCCGTCGCTGCGCGCCCTGCTCCTCGGC
GCCGCTGGGCTGCTGCTCCTGCTCCTGCCCCTCTCCTCTTCCTCCTCTTCGGACACCTGCGGCCCCTGCG
AGCCGGCCTCCTGCCCGCCCCTGCCCCCGCTGGGCTGCCTGCTGGGCGAGACCCGCGACGCGTGCGGCTG
CTGCCCTATGTGCGCCCGCGGCGAGGGCGAGCCGTGCGGGGGTGGCGGCGCCGGCAGGGGGTACTGCGCG
CCGGGCATGGAGTGCGTGAAGAGCCGCAAGAGGCGGAAGGGTAAAGCCGGGGCAGCAGCCGGCGGTCCGG
GTGTAAGCGGCGTGTGCGTGTGCAAGAGCCGCTACCCGGTGTGCGGCAGCGACGGCACCACCTACCCGAG
CGGCTGCCAGCTGCGCGCCGCCAGCCAGAGGGCCGAGAGCCGCGGGGAGAAGGCCATCACCCAGGTCAGC
AAGGGCACCTGCGAGCAAGGTCCTTCCATAGTGACGCCCCCAAGGACATCTGGAATGTCACTGGTGCCC
AGGTGTACTTGAGCTGTGAGGTCATCGGAATCCCGACACCTGTCCTCATCTGGAACAAGGTAAAAGGGG
TCACTATGGAGTTCAAAGGACAGAACTCCTGCCTGGTGACCGGGACAACCTGGCCATTCAGACCCGGGGT
GGCCCAGAAAAGCATGAAGTAACTGGCTGGGTGCTGGTATCTCCTCTAAGTAAGGAAGATGCTGGAGAAT
ATGAGTGCCATGCATCCAATTCCCAAGGACAGGCTTCAGCATCAGCAAAAATTACAGTGGTTGATGCCTT
ACATGAAATACCAGTGAAAAAAGGTACACAATAAATCTCACAGCCATTTAAAAATGACTAGTACATTTGC
TTTAAAAAGAACAGAACTAAGTATGAAAGTATCAGACGTAGCTATTGATGAAATTCTGTAGTTAGCAACC
CATAAGGGCATTAAGTATGCCATTAAAATGTACAGCATGAGACTCCAAAAGATTATCTGGATGGGTGACT
G

SEQ ID NO: 3:

Human IGFBP7 protein sequence, accession number NP 001544.1, isoform 1 precursor MERPSLRALLLGAAGLLLLLLPLSSSSSSDTCGPCEPASCPPLPPLGCLLGETRDACGCCPMCARGEGEP
CGGGGAGRGYCAPGMECVKSRKRRKGKAGAAAGGPGVSGVCVCKSRYPVCGSDGTTYPSGCQLRAASQRA
ESRGEKAITQVSKGTCEQGPSIVTPPKDIWNVTGAQVYLSCEVIGIPTPVLIWNKVKRGHYGVQRTELLP
GDRDNLAIQTRGGPEKHEVTGWVLVSPLSKEDAGEYECHASNSQGQASASAKITVVDALHEIPVKKGEGA
EL

SEQ ID NO: 4:

Human IGFBP7 protein sequence, accession number NP 001240764.1, isoform 2 precursor MERPSLRALLLGAAGLLLLLLPLSSSSSSDTCGPCEPASCPPLPPLGCLLGETRDACGCCPMCARGEGEP
CGGGGAGRGYCAPGMECVKSRKRRKGKAGAAAGGPGVSGVCVCKSRYPVCGSDGTTYPSGCQLRAASQRA
ESRGEKAITQVSKGTCEQGPSIVTPPKDIWNVTGAQVYLSCEVIGIPTPVLIWNKVKRGHYGVQRTELLP
GDRDNLAIQTRGGPEKHEVTGWVLVSPLSKEDAGEYECHASNSQGQASASAKITVVDALHEIPVKKGTQ

Figure 1B

SEQ ID NO: 5:

Human IGF-1R mRNA sequence, accession number NM 000875.4, transcript variant 1

AGTGTGTGGCAGCGGCGGCGGCGGCGCGGCGAGGCTGGGGCTCTTGTTTACCAGCATTAACTCCGCTGAG
CGGAAAAAAAAGGGAAAAAACCCGAGGAGGAGCGAGCGCACCAGGCGAACTCGAGAGAGGCGGGAGAGC
GAGAGGGACGCCGCCAGCGAGCCTGCCCACGGCCGGCGCTCGCAGACCCTCGGCCCCGCTCCCCGGATCC
CCCCGCGCCCTCCACGCCCCTCCCGCGCGGGGGCAGCTCCACGGCGCGCCTCGCCTCGGCTGTGACCTTC
AGCGAGCCGGAGCCCCCGCGCAGAGCAGGCGGCGGCGGGCGGGGGCCGGGCGGGGCCGGCGCGGGGCGG
GCGGCGGCGCAGAGCCGGGCGGCGCGGCGGGAGTGCTGAGCGCGGCGCGGCCGGCCCGCCGCTTTGTGTG
TGTCCTGGATTTGGGAAGGAGCTCGCCGCGGCGGCGGCGGCGCTGAGGGAGGAGGCGGCGGCGAGCGGAG
CCAGGAGGAGGAGGAGGAGGGGGAGCCGCTCATTCATTTTGACTCCGCGTTTCTGCCCCTCGCCGGCCTC
GCCTGTGACCCGGACTTCGGGGCGATCTTGCGAACTGCGTCGCGCCCTCCCGCGGCGGAAGCTCGGGCGT
CCGGCCGCCTCCCGCGCGGCCAGGGCCGGGCTTGTTTTTCCTCGCCTAGGCAGATTTGGGCTTTGCCCCC
TTTCTTTGCAGTTTTCCCCCCTTCCTGCCTCTCCGGGTTTGAAAATGGAGGCCGACGACGCCGACAGCCC
GCCCCGGCGCGCCTCGGGTTCCCGACTCCGCCGAGCCCTGGGCCGCTGCTGCCGGCGCTGAGGGGCCGCC
CCGCGCCGCCCGCCCCGTCCGCGCACCCGGAGGGCCCCGGCGGCGCCGCCTTCGGAGTATTGTTTCCTTC
GCCCTTGTTTTGGAGGGGGAGCGAAGACTGAGTTTGAGACTTGTTTCCTTTCATTTCCTTTTTTTCTTT
TCTTTTCTTTTTTTTTTTTTTTTTTTTTGAGAAAGGGGAATTTCATCCCAAATAAAAGGAATGAAGT
CTGGCTCCGGAGGAGGGTCCCCGACCTCGCTGTGGGGCTCCTGTTTCTCTCCGCCGCGCTCTCGCTCTG
GCCGACGAGTGGAGAAATCTGCGGGCCAGGCATCGACATCCGCAACGACTATCAGCAGCTGAAGCGCCTG
GAGAACTGCACGGTGATCGAGGGCTACCTCCACATCCTGCTCATCTCCAAGGCCGAGGACTACCGCAGCT
ACCGCTTCCCCAAGCTCACGGTCATTACCGAGTACTTGCTGCTGTTCCGAGTGGCTGGCCTCGAGAGCCT
CGGAGACCTCTTCCCCAACCTCACGGTCATCCGCGGCTGGAAACTCTTCTACAACTACGCCCTGGTCATC
TTCGAGATGACCAATCTCAAGGATATTGGGCTTTACAACCTGAGGAACATTACTCGGGGGGCCATCAGGA
TTGAGAAAAATGCTGACCTCTGTTACCTCTCCACTGTGGACTGGTCCCTGATCCTGGATGCGGTGTCCAA
TAACTACATTGTGGGGAATAAGCCCCCAAAGGAATGTGGGGACCTGTGTCCAGGGACCATGGAGGAGAAG
CCGATGTGTGAGAAGACCACCATCAACAATGAGTACAACTACCGCTGCTGGACCACAAACCGCTGCCAGA
AAATGTGCCCAAGCACGTGTGGGAAGCGGGCGTGCACCGAGAACAATGAGTGCTGCCACCCCGAGTGCCT
GGGCAGCTGCAGCGCGCCTGACAACGACACGGCCTGTGTAGCTTGCCGCCACTACTACTATGCCGGTGTC
TGTGTGCCTGCCTGCCCGCCCAACACCTACAGGTTTGAGGGCTGGCGCTGTGTGGACCGTGACTTCTGCG
CCAACATCCTCAGCGCCGAGAGCAGCGACTCCGAGGGGTTTGTGATCCACGACGGCGAGTGCATGCAGGA
GTGCCCCTCGGGCTTCATCCGCAACGGCAGCCAGAGCATGTACTGCATCCCTTGTGAAGGTCCTTGCCCG
AAGGTCTGTGAGGAAGAAAAGAAAACAAAGACCATTGATTCTGTTACTTCTGCTCAGATGCTCCAAGGAT
GCACCATCTTCAAGGGCAATTTGCTCATTAACATCCGACGGGGAATAACATTGCTTCAGAGCTGGAGAA
CTTCATGGGCTCATCGAGGTGGTGACGGGCTACGTGAAGATCCGCCATTCTCATGCCTTGGTCTCCTTG
TCCTTCCTAAAAAACCTTCGCCTCATCCTAGGAGAGGAGCAGCTAGAAGGGAATTACTCCTTCTACGTCC
TCGACAACCAGAACTTGCAGCAACTGTGGGACTGGGACCACCGCAACCTGACCATCAAAGCAGGGAAAAT
GTACTTTGCTTTCAATCCCAAATTATGTGTTTCCGAAATTTACCGCATGGAGGAAGTGACGGGGACTAAA
GGGCGCCAAAGCAAAGGGGACATAAACACCAGGAACAACGGGGAGAGAGCCTCCTGTGAAAGTGACGTCC

Figure 1C

```
TGCATTTCACCTCCACCACCACGTCGAAGAATCGCATCATCATAACCTGGCACCGGTACCGGCCCCCTGA
CTACAGGGATCTCATCAGCTTCACCGTTTACTACAAGGAAGCACCCTTTAAGAATGTCACAGAGTATGAT
GGGCAGGATGCCTGCGGCTCCAACAGCTGGAACATGGTGGACGTGGACCTCCCGCCCAACAAGGACGTGG
AGCCCGGCATCTTACTACATGGGCTGAAGCCCTGGACTCAGTACGCCGTTTACGTCAAGGCTGTGACCCT
CACCATGGTGGAGAACGACCATATCCGTGGGGCCAAGAGTGAGATCTTGTACATTCGCACCAATGCTTCA
GTTCCTTCCATTCCCTTGGACGTTCTTTCAGCATCGAACTCCTCTTCTCAGTTAATCGTGAAGTGGAACC
CTCCCTCTCTGCCCAACGGCAACCTGAGTTACTACATTGTGCGCTGGCAGCGGCAGCCTCAGGACGGCTA
CCTTTACCGGCACAATTACTGCTCCAAAGACAAAATCCCCATCAGGAAGTATGCCGACGGCACCATCGAC
ATTGAGGAGGTCACAGAGAACCCCAAGACTGAGGTGTGTGGTGGGGAGAAAGGGCCTTGCTGCGCCTGCC
CCAAAACTGAAGCCGAGAAGCAGGCCGAGAAGGAGGAGGCTGAATACCGCAAAGTCTTTGAGAATTTCCT
GCACAACTCCATCTTCGTGCCCAGACCTGAAAGGAAGCGGAGAGATGTCATGCAAGTGGCCAACACCACC
ATGTCCAGCCGAAGCAGGAACACCACGGCCGCAGACACCTACAACATCACCGACCCGGAAGAGCTGGAGA
CAGAGTACCCTTTCTTTGAGAGCAGAGTGGATAACAAGGAGAGAACTGTCATTTCTAACCTTCGGCCTTT
CACATTGTACCGCATCGATATCCACAGCTGCAACCACGAGGCTGAGAAGCTGGGCTGCAGCGCCTCCAAC
TTCGTCTTTGCAAGGACTATGCCCGCAGAAGGAGCAGATGACATTCCTGGGCCAGTGACCTGGGAGCCAA
GGCCTGAAAACTCCATCTTTTTAAAGTGGCCGGAACCTGAGAATCCCAATGGATTGATTCTAATGTATGA
AATAAAATACGGATCACAAGTTGAGGATCAGCGAGAATGTGTGTCCAGACAGGAATACAGGAAGTATGGA
GGGGCCAAGCTAAACCGGCTAAACCCGGGGAACTACACAGCCCGGATTCAGGCCACATCTCTCTCTGGGA
ATGGGTCGTGGACAGATCCTGTGTTCTTCTATGTCCAGGCCAAAACAGGATATGAAAACTTCATCCATCT
GATCATCGCTCTGCCCGTCGCTGTCCTGTTGATCGTGGGAGGGTTGGTGATTATGCTGTACGTCTTCCAT
AGAAAGAGAAATAACAGCAGGCTGGGGAATGGAGTGCTGTATGCCTCTGTGAACCCGGAGTACTTCAGCG
CTGCTGATGTGTACGTTCCTGATGAGTGGGAGGTGGCTCGGGAGAAGATCACCATGAGCCGGGAACTTGG
GCAGGGGTCGTTTGGGATGGTCTATGAAGGAGTTGCCAAGGGTGTGGTGAAAGATGAACCTGAAACCAGA
GTGGCCATTAAAACAGTGAACGAGGCCGCAAGCATGCGTGAGAGGATTGAGTTTCTCAACGAAGCTTCTG
TGATGAAGGAGTTCAATTGTCACCATGTGGTGCGATTGCTGGGTGTGGTGTCCCAAGGCCAGCCAACACT
GGTCATCATGGAACTGATGACACGGGGCGATCTCAAAAGTTATCTCCGGTCTCTGAGGCCAGAAATGGAG
AATAATCCAGTCCTAGCACCTCCAAGCCTGAGCAAGATGATTCAGATGGCCGGAGAGATTGCAGACGGCA
TGGCATACCTCAACGCCAATAAGTTCGTCCACAGAGACCTTGCTGCCCGGAATTGCATGGTAGCCGAAGA
TTTCACAGTCAAAATCGGAGATTTTGGTATGACGCGAGATATCTATGAGACAGACTATTACCGGAAAGGA
GGGAAAGGGCTGCTGCCCGTGCGCTGGATGTCTCCTGAGTCCCTCAAGGATGGAGTCTTCACCACTTACT
CGGACGTCTGGTCCTTCGGGGTCGTCCTCTGGGAGATCGCCACACTGGCCGAGCAGCCCTACCAGGGCTT
GTCCAACGAGCAAGTCCTTCGCTTCGTCATGGAGGGCGGCCTTCTGGACAAGCCAGACAACTGTCCTGAC
ATGCTGTTTGAACTGATGCGCATGTGCTGGCAGTATAACCCCAAGATGAGGCCTTCCTTCCTGGAGATCA
TCAGCAGCATCAAAGAGGAGATGGAGCCTGGCTTCCGGGAGGTCTCCTTCTACTACAGCGAGGAGAACAA
GCTGCCCGAGCCGGAGGAGCTGGACCTGGAGCCAGAGAACATGGAGAGCGTCCCCCTGGACCCCTCGGCC
TCCTCGTCCTCCCTGCCACTGCCCGACAGACACTCAGGACACAAGGCCGAGAACGGCCCCGGCCCTGGGG
TGCTGGTCCTCCGCGCCAGCTTCGACGAGAGACAGCCTTACGCCCACATGAACGGGGGCCGCAAGAACGA
GCGGGCCTTGCCGCTGCCCCAGTCTTCGACCTGCTGATCCTTGGATCCTGAATCTGTGCAAACAGTAACG
TGTGCGCACGCGCAGCGGGGTGGGGGGGGAGAGAGAGTTTTAACAATCCATTCACAAGCCTCCTGTACCT
```

Figure 1C Cont.

```
CAGTGGATCTTCAGAACTGCCCTTGCTGCCCGCGGGAGACAGCTTCTCTGCAGTAAAACACATTTGGGAT
GTTCCTTTTTTCAATATGCAAGCAGCTTTTTATTCCCTGCCCAAACCCTTAACTGACATGGGCCTTTAAG
AACCTTAATGACAACACTTAATAGCAACAGAGCACTTGAGAACCAGTCTCCTCACTCTGTCCCTGTCCTT
CCCTGTTCTCCCTTTCTCTCTCCTCTCTGCTTCATAACGGAAAAATAATTGCCACAAGTCCAGCTGGGAA
GCCCTTTTTATCAGTTTGAGGAAGTGGCTGTCCCTGTGGCCCCATCCAACCACTGTACACACCCGCCTGA
CACCGTGGGTCATTACAAAAAAACACGTGGAGATGGAAATTTTTACCTTTATCTTTCACCTTTCTAGGGA
CATGAAATTTACAAAGGGCCATCGTTCATCCAAGGCTGTTACCATTTTAACGCTGCCTAATTTTGCCAAA
ATCCTGAACTTTCTCCCTCATCGGCCCGGCGCTGATTCCTCGTGTCCGGAGGCATGGGTGAGCATGGCAG
CTGGTTGCTCCATTTGAGAGACACGCTGGCGACACACTCCGTCCATCCGACTGCCCCTGCTGTGCTGCTC
AAGGCCACAGGCACACAGGTCTCATTGCTTCTGACTAGATTATTATTTGGGGGAACTGGACACAATAGGT
CTTTCTCTCAGTGAAGGTGGGGAGAAGCTGAACCGGCTTCCCTGCCCTGCCTCCCCAGCCCCCTGCCCAA
CCCCCAAGAATCTGGTGGCCATGGGCCCCGAAGCAGCCTGGCGGACAGGCTTGGAGTCAAGGGGCCCCAT
GCCTGCTTCTCCCAGCCCCAGCTCCCCGCCCGCCCCCAAGGACACAGATGGGAAGGGGTTTCCAGGG
ACTCAGCCCCACTGTTGATGCAGGTTTGCAAGGAAAGAAATTCAAACACCACAACAGCAGTAAGAAGAAA
AGCAGTCAATGGATTCAAGCATTCTAAGCTTTGTTGACATTTTCTCTGTTCCTAGGACTTCTTCATGGGT
CTTACAGTTCTATGTTAGACCATGAAACATTTGCATACACATCGTCTTTAATGTCACTTTTATAACTTTT
TTACGGTTCAGATATTCATCTATACGTCTGTACAGAAAAAAAAAGCTGCTATTTTTTTTGTTCTTGATC
TTTGTGGATTTAATCTATGAAAACCTTCAGGTCCACCCTCTCCCCTTTCTGCTCACTCCAAGAAACTTCT
TATGCTTTGTACTAGAGTGCGTGACTTCTTCCTCTTTTCCCGGTAATGGATACTTCTATCACATAATTT
GCCATGAACTGTTGGATGCCTTTTTATAAATACATCCCCCATCCCTGCTCCCACCTGCCCCTTTAGTTGT
TTTCTAACCCGTAGGCTCTCTGGGCACGAGGCAGAAAGCAGGCCGGGCACCCATCCTGAGAGGGCCGCGC
TCCTCTCCCCAGCCTGCCCTCACAGCATTGGAGCCTGTTACAGTGCAAGACATGATACAAACTCAGGTCA
GAAAAACAAAGGTTAAATATTTCACACGTCTTTGTTCAGTGTTTCCACTCACCGTGGTTGAGAAGCCTCA
CCCTCTCTTTCCCTTGCCTTTGCTTAGGTTGTGACACACATATATATATATTTTTTAATTCTTGGGTAC
AACAGCAGTGTTAACCGCAGACACTAGGCATTTGGATTACTATTTTCTTAATGGCTATTTAATCCTTCC
ATCCCACGAAAAACAGCTGCTGAGTCCAAGGGAGCAGCAGAGCGTGGTCCGGCAGGGCCTGTTGTGGCCC
TCGCCACCCCCTCACCGGACCGACTGACCTGTCTTTGGAACCAGAACATCCCAAGGGAACTCCTTCGCA
CTGGCGTTGAGTGGGACCCCGGGATCCAGGCTGGCCCAGGGCGGCACCCTCAGGGCTGTGCCCGCTGGAG
TGCTAGGTGGAGGCAGCACAGACGCCACGGTGGCCCAAGAGCCCCTTTGCTTCTTGCTGGGGGACCAGGG
CTGTGGTGCTGGCCCACTTTCCCTCGGCCAGGAATCCAGGTCCTTGGGGCCCAGGGGTCTTGTCTTGTTT
CATTTTTAGCACTTCTCACCAGAGAGATGACAGCACAAGAGTTGCTTCTGGGATAGAAATGTTTAGGAGT
AAGAACAAAGCTGGGATACGGTGATTGCTAGTTGTGACTGAAGATTCAACACAGAAAAGAAAGTTTATAC
GGCTTTTTTGCTGGTCAGCAGTTTGTCCCACTGCTTTCTCTAGTCTCTATCCCATAGCGTGTTCCCTTTA
AAAAAAAAAAAAGGTATTATATGTAGGAGTTTTCTTTTAATTTATTTTGTGATAAATTACCAGTTTCAA
TCACTGTAGAAAAGCCCCATTATGAATTTAAATTTCAAGGAAAGGGTGTGTGTGTGTATGTGTGGGGT
GTGTGTGTGAGAGTGATGGGACAGTTCTTGATTTTTGGGTTTTTTTCCCCAAACATTTATCTACC
TCACTCTTATTTTTTATATGTGTATATAGACAAAAGAATACATCTCACCTTTCTCAGCACCTGACAATAG
GCCGTTGATACTGGTAACCTCATCCACGCCACAGGCGCCACACCCAGGTGATGCAGGGGGAAGCCAGGCT
GTATTCCGGGGTCAAAGCAACACTAACTCACCTCTCTGCTCATTTCAGACAGCTTGCCTTTTTCTGAGAT
```

Figure 1C Cont.

```
GTCCTGTTTTGTGTTGCTTTTTTTGTTTTGTTTTCTATCTTGGTTTCCACCAAGGTGTTAGATTTCTCCT
CCTCCTAGCCAGGTGGCCCTGTGAGGCCAACGAGGGCACCAGAGCACACCTGGGGGAGCCACCAGGCTGT
CCCTGGCTGGTTGTCTTTGGAACAAACTGCTTCTGTGCAGATGGAATGACCAACACATTTCGTCCTTAAG
AGAGCAGTGGTTCCTCAGGTTCTGAGGAGAGGAAGGTGTCCAGGCAGCACCATCTCTGTGCGAATCCCCA
GGGTAAAGGCGTGGGGCATTGGGTTTGCTCCCCTTGCTGCTGCTCCATCCCTGCAGGAGGCTCGCGCTGA
GGCAGGACCGTGCGGCCATGGCTGCTGCATTCATTGAGCACAAAGGTGCAGCTGCAGCAGCAGCTGGAGA
GCAAGAGTCACCCAGCCTGTGCGCCAGAATGCAGAGGCTCCTGACCTCACAGCCAGTCCCTGATAGAACA
CACGCAGGAGCAGAGTCCCCTCCCCCTCCAGGCTGCCCTCTCAACTTCTCCCTCACCTCCTTCCCTAGGG
GTAGACAGAGATGTACCAAACCTTCCGGCTGGAAAGCCCAGTGGCCGGCGCCGAGGCTCGTGGCGTCACG
CCCCCCCCGCCAGGGCTGTACCTCCGTCTCCCTGGTCCTGCTGCTCACAGGACAGACGGCTCGCTCCCCT
CTTCCAGCAGCTGCTCTTACAGGCACTGATGATTTCGCTGGGAAGTGTGGCGGGCAGCTTTGCCTAAGCG
TGGATGGCTCCTCGGCAATTCCAGCCTAAGTGAAGGCGCTCAGGAGCCTCCTGCTGGAACGCGACCCATC
TCTCCCAGGACCCCGGGGATCTTAAGGTCATTGAGAAATACTGTTGGATCAGGGTTTTGTTCTTCCACAC
TGTAGGTGACCCCTTGGAATAACGGCCTCTCCTCTCGTGCACATACCTACCGGTTTCCACAACTGGATTT
CTACAGATCATTCAGCTGGTTATAAGGGTTTTGTTTAAACTGTCCGAGTTACTGATGTCATTTTGTTTTT
GTTTTATGTAGGTAGCTTTTAAGTAGAAAACACTAACAGTGTAGTGCCCATCATAGCAAATGCTTCAGAA
ACACCTCAATAAAAGAGAAAACTTGGCTTGTGTGATGGTGCAGTCACTTTACTGGACCAACCCACCCACC
TTGACTATACCAAGGCATCATCTATCCACAGTTCTAGCCTAACTTCATGCTGATTTCTCTGCCTCTTGAT
TTTTCTCTGTGTGTTCCAAATAATCTTAAGCTGAGTTGTGGCATTTTCCATGCAACCTCCTTCTGCCAGC
AGCTCACACTGCTTGAAGTCATATGAACCACTGAGGCACATCATGGAATTGATGTGAGCATTAAGACGTT
CTCCCACACAGCCCTTCCCTGAGGCAGCAGGAGCTGGTGTGTACTGGAGACACTGTTGAACTTGATCAAG
ACCCAGACCACCCCAGGTCTCCTTCGTGGGATGTCATGACGTTTGACATACCTTTGGAACGAGCCTCCTC
CTTGGAAGATGGAAGACCGTGTTCGTGGCCGACCTGGCCTCTCCTGGCCTGTTTCTTAAGATGCGGAGTC
ACATTTCAATGGTACGAAAAGTGGCTTCGTAAAATAGAAGAGCAGTCACTGTGGAACTACCAAATGGCGA
GATGCTCGGTGCACATTGGGGTGCTTTGGGATAAAAGATTTATGAGCCAACTATTCTCTGGCACCAGATT
CTAGGCCAGTTTGTTCCACTGAAGCTTTTCCCACAGCAGTCCACCTCTGCAGGCTGGCAGCCGAATGGCT
TGCCAGTGGCTCTGTGGCAAGATCACACTGAGATCGATGGGTGAGAAGGCTAGGATGCTTGTCTAGTGTT
CTTAGCTGTCACGTTGGCTCCTTCCAGGGTGGCCAGACGGTGTTGGCCACTCCCTTCTAAAACACAGGCG
CCCTCCTGGTGACAGTGACCCGCCGTGGTATGCCTTGGCCCATTCCAGCAGTCCCAGTTATGCATTTCAA
GTTTGGGGTTTGTTCTTTTCGTTAATGTTCCTCTGTGTTGTCAGCTGTCTTCATTTCCTGGGCTAAGCAG
CATTGGGAGATGTGGACCAGAGATCCACTCCTTAAGAACCAGTGGCGAAAGACACTTTCTTTCTTCACTC
TGAAGTAGCTGGTGGTACAAATGAGAACTTCAAGAGAGGATGTTATTTAGACTGAACCTCTGTTGCCAGA
GATGCTGAAGATACAGACCTTGGACAGGTCAGAGGGTTTCATTTTTGGCCTTCATCTTAGATGACTGGTT
GCGTCATTTGGAGAAGTGAGTGCTCCTTGATGGTGGAATGACCGGGTGGTGGGTACAGAACCATTGTCAC
AGGGATCCTGGCACAGAGAAGAGTTACGAGCAGCAGGGTGCAGGGCTTGGAAGGAATGTGGGCAAGGTTT
TGAACTTGATTGTTCTTGAAGCTATCAGACCACATCGAGGCTCAGCAGTCATCCGTGGGCATTTGGTTTC
AACAAAGAAACCTAACATCCTACTCTGGAAACTGATCTCGGAGTTAAGGCGAATTGTTCAAGAACACAAA
CTACATCGCACTCGTCAGTTGTCAGTTCTGGGGCATGACTTTAGCGTTTTGTTTCTGCGAGAACATAACG
ATCACTCATTTTTATGTCCCACGTGTGTGTGTCCGCATCTTTCTGGTCAACATTGTTTTAACTAGTCACT
```

Figure 1C Cont.

```
CATTAGCGTTTTCAATAGGGCTCTTAAGTCCAGTAGATTACGGGTAGTCAGTTGACGAAGATCTGGTTTA
CAAGAACTAATTAAATGTTTCATTGCATTTTTGTAAGAACAGAATAATTTTATAAAATGTTTGTAGTTTA
TAATTGCCGAAAATAATTTAAAGACACTTTTTTTTTCTCTGTGTGTGCAAATGTGTGTTTGTGATCCATT
TTTTTTTTTTTTTTTAGGACACCTGTTTACTAGCTAGCTTTACAATATGCCAAAAAAGGATTTCTCCCT
GACCCCATCCGTGGTTCACCCTCTTTTCCCCCCATGCTTTTTGCCCTAGTTTATAACAAAGGAATGATGA
TGATTTAAAAGTAGTTCTGTATCTTCAGTATCTTGGTCTTCCAGAACCCTCTGGTTGGGAAGGGGATCA
TTTTTTACTGGTCATTTCCCTTTGGAGTGTAGCTACTTTAACAGATGGAAAGAACCTCATTGGCCATGGA
AACAGCCGAGGTGTTGGAGCCCAGCAGTGCATGGCACCGTTCGGCATCTGGCTTGATTGGTCTGGCTGCC
GTCATTGTCAGCACAGTGCCATGGACATGGGAAGACTTGACTGCACAGCCAATGGTTTTCATGATGATTA
CAGCATACACAGTGATCACATAAACGATGACAGCTATGGGGCACACAGGCCATTTGCTTACATGCCTCGT
ATCATGACTGATTACTGCTTTGTTAGAACACAGAAGAGACCCTATTTTATTTAAGGCAGAACCCCGAAGA
TACGTATTTCCAATACAGAAAAGAATTTTTAATAAAAACTATAACATACACAAAAATTGGTTTTAAAGTT
GACTCCACTTCCTCTAACTCCAGTGGATTGTTGGCCATGTCTCCCCAACTCCACAATATCTCTATCATGG
GAAACACCTGGGGTTTTTGCGCTACATAGGAGAAAGATCTGGAAACTATTTGGGTTTTGTTTTCAACTTT
TCATTTGGATGTTTGGCGTTGCACACACACATCCACCGGTGGAAGAGACGCCCGGTGAAAACACCTGTCT
GCTTTCTAAGCCAGTGAGGTTGAGGTGAGAGGTTTGCCAGAGTTTGTCTACCTCTGGGTATCCCTTTGTC
TGGGATAAAAAAAATCAAACCAGAAGGCGGGATGGAATGGATGCACCGCAAATAATGCATTTCTGAGTT
TTCTTGTTAAAAAAAATTTTTTTAAGTAAGAAAAAAAAAGGTAATAACATGGCCAATTTGTTACATAAA
ATGACTTTCTGTGTATAAATTATTCCTAAAAAATCCTGTTTATATAAAAAATCAGTAGATGAAAAAAATT
TCAAAATGTTTTTGTATATTCTGTTGTAAGAATTTATTCCTGTTATTGCGATATACTCTGGATTCTTTAC
ATAATGGAAAAAGAAACTGTCTATTTTGAATGGCTGAAGCTAAGGCAACGTTAGTTTCTCTTACTCTGC
TTTTTTCTAGTAAAGTACTACATGGTTTAAGTTAAATAAAATAATTCTGTATGCAAAAAAAAAAAAAAAA
AAAAAAAAAAA
```

Figure 1C Cont.

SEQ ID NO: 6:

Human IGF-1R mRNA sequence, accession number NM 001291858.1, transcript variant 2

```
AGTGTGTGGCAGCGGCGGCGGCGGCGCGGCGAGGCTGGGGCTCTTGTTTACCAGCATTAACTCCGCTGAG
CGGAAAAAAAAGGGAAAAAACCCGAGGAGGAGCGAGCGCACCAGGCGAACTCGAGAGAGGCGGGAGAGC
GAGAGGGACGCCGCCAGCGAGCCTGCCCACGGCCGGCGCTCGCAGACCCTCGGCCCCGCTCCCCGGATCC
CCCCGCGCCCTCCACGCCCCTCCCGCGCGGGGGCAGCTCCACGGCGCGCCTCGCCTCGGCTGTGACCTTC
AGCGAGCCGGAGCCCCGCGCAGAGCAGGCGGCGGCGGGCGGGGGCCGGGCGGGGGCCGGCGCGGGGCGG
GCGGCGGCGCAGAGCCGGGCGGCGCGGCGGGAGTGCTGAGCGCGGCGCGGCCGGCCCGCCGCTTTGTGTG
TGTCCTGGATTTGGGAAGGAGCTCGCCGCGGCGGCGGCGGCGCTGAGGGAGGAGGCGGCGGCGAGCGGAG
CCAGGAGGAGGAGGAGGAGGGGGAGCCGCTCATTCATTTTGACTCCGCGTTTCTGCCCCTCGCCGGCCTC
GCCTGTGACCCGGACTTCGGGGCGATCTTGCGAACTGCGTCGCGCCTCCCGCGGCGGAAGCTCGGGCGT
CCGGCCGCCTCCCGCGCGGCCAGGGCCGGGCTTGTTTTCCTCGCCTAGGCAGATTTGGGCTTTGCCCCC
TTTCTTTGCAGTTTTCCCCCCTTCCTGCCTCTCCGGGTTTGAAAATGGAGGCCGACGACGCCGACAGCCC
GCCCCGGCGCGCCTCGGGTTCCCGACTCCGCCGAGCCCTGGGCCGCTGCTGCCGGCGCTGAGGGGCCGCC
CCGCGCCGCCCGCCCCGTCCGCGCACCCGGAGGGCCCCGGCGGCGCCGCCTTCGGAGTATTGTTTCCTTC
GCCCTTGTTTTGGAGGGGGAGCGAAGACTGAGTTTGAGACTTGTTTCCTTTCATTTCCTTTTTTTCTTT
TCTTTTCTTTTTTTTTTTTTTTTTTTTTGAGAAAGGGGAATTTCATCCCAAATAAAAGGAATGAAGT
CTGGCTCCGGAGGAGGGTCCCCGACCTCGCTGTGGGGCTCCTGTTTCTCTCCGCCGCGCTCTCGCTCTG
GCCGACGAGTGGAGAAATCTGCGGGCCAGGCATCGACATCCGCAACGACTATCAGCAGCTGAAGCGCCTG
GAGAACTGCACGGTGATCGAGGGCTACCTCCACATCCTGCTCATCTCCAAGGCCGAGGACTACCGCAGCT
ACCGCTTCCCCAAGCTCACGGTCATTACCGAGTACTTGCTGCTGTTCCGAGTGGCTGGCCTCGAGAGCCT
CGGAGACCTCTTCCCCAACCTCACGGTCATCCGCGGCTGGAAACTCTTCTACAACTACGCCCTGGTCATC
TTCGAGATGACCAATCTCAAGGATATTGGGCTTTACAACCTGAGGAACATTACTCGGGGGGCCATCAGGA
TTGAGAAAAATGCTGACCTCTGTTACCTCTCCACTGTGGACTGGTCCCTGATCCTGGATGCGGTGTCCAA
TAACTACATTGTGGGGAATAAGCCCCCAAAGGAATGTGGGGACCTGTGTCCAGGGACCATGGAGGAGAAG
CCGATGTGTGAGAAGACCACCATCAACAATGAGTACAACTACCGCTGCTGGACCACAAACCGCTGCCAGA
AAATGTGCCCAAGCACGTGTGGGAAGCGGGCGTGCACCGAGAACAATGAGTGCTGCCACCCCGAGTGCCT
GGGCAGCTGCAGCGCGCCTGACAACGACACGGCCTGTGTAGCTTGCCGCCACTACTACTATGCCGGTGTC
TGTGTGCCTGCCTGCCCGCCCAACACCTACAGGTTTGAGGGCTGGCGCTGTGTGGACCGTGACTTCTGCG
CCAACATCCTCAGCGCCGAGAGCAGCGACTCCGAGGGGTTTGTGATCCACGACGGCGAGTGCATGCAGGA
GTGCCCCTCGGGCTTCATCCGCAACGGCAGCCAGAGCATGTACTGCATCCCTTGTGAAGGTCCTTGCCCG
AAGGTCTGTGAGGAAGAAAAGAAAACAAAGACCATTGATTCTGTTACTTCTGCTCAGATGCTCCAAGGAT
GCACCATCTTCAAGGGCAATTTGCTCATTAACATCCGACGGGGAATAACATTGCTTCAGAGCTGGAGAA
CTTCATGGGGCTCATCGAGGTGGTGACGGGCTACGTGAAGATCCGCCATTCTCATGCCTTGGTCTCCTTG
TCCTTCCTAAAAAACCTTCGCCTCATCCTAGGAGAGGAGCAGCTAGAAGGGAATTACTCCTTCTACGTCC
TCGACAACCAGAACTTGCAGCAACTGTGGGACTGGGACCACCGCAACCTGACCATCAAAGCAGGGAAAAT
GTACTTTGCTTTCAATCCCAAATTATGTGTTTCCGAAATTTACCGCATGGAGGAAGTGACGGGGACTAAA
GGGCGCCAAAGCAAAGGGGACATAAACACCAGGAACAACGGGGAGAGAGCCTCCTGTGAAAGTGACGTCC
```

Figure 1D

```
TGCATTTCACCTCCACCACCACGTCGAAGAATCGCATCATCATAACCTGGCACCGGTACCGGCCCCCTGA
CTACAGGGATCTCATCAGCTTCACCGTTTACTACAAGGAAGCACCCTTTAAGAATGTCACAGAGTATGAT
GGGCAGGATGCCTGCGGCTCCAACAGCTGGAACATGGTGGACGTGGACCTCCCGCCCAACAAGGACGTGG
AGCCCGGCATCTTACTACATGGGCTGAAGCCCTGGACTCAGTACGCCGTTTACGTCAAGGCTGTGACCCT
CACCATGGTGGAGAACGACCATATCCGTGGGGCCAAGAGTGAGATCTTGTACATTCGCACCAATGCTTCA
GTTCCTTCCATTCCCTTGGACGTTCTTTCAGCATCGAACTCCTCTTCTCAGTTAATCGTGAAGTGGAACC
CTCCCTCTCTGCCCAACGGCAACCTGAGTTACTACATTGTGCGCTGGCAGCGGCAGCCTCAGGACGGCTA
CCTTTACCGGCACAATTACTGCTCCAAAGACAAAATCCCCATCAGGAAGTATGCCGACGGCACCATCGAC
ATTGAGGAGGTCACAGAGAACCCCAAGACTGAGGTGTGTGGTGGGGAGAAAGGGCCTTGCTGCGCCTGCC
CCAAAACTGAAGCCGAGAAGCAGGCCGAGAAGGAGGAGGCTGAATACCGCAAAGTCTTTGAGAATTTCCT
GCACAACTCCATCTTCGTGCCCAGACCTGAAAGGAAGCGGAGAGATGTCATGCAAGTGGCCAACACCACC
ATGTCCAGCCGAAGCAGGAACACCACGGCCGCAGACACCTACAACATCACCGACCCGGAAGAGCTGGAGA
CAGAGTACCCTTTCTTTGAGAGCAGAGTGGATAACAAGGAGAGAACTGTCATTTCTAACCTTCGGCCTTT
CACATTGTACCGCATCGATATCCACAGCTGCAACCACGAGGCTGAGAAGCTGGGCTGCAGCGCCTCCAAC
TTCGTCTTTGCAAGGACTATGCCCGCAGAAGGAGCAGATGACATTCCTGGGCCAGTGACCTGGGAGCCAA
GGCCTGAAAACTCCATCTTTTTAAAGTGGCCGGAACCTGAGAATCCCAATGGATTGATTCTAATGTATGA
AATAAAATACGGATCACAAGTTGAGGATCAGCGAGAATGTGTGTCCAGACAGGAATACAGGAAGTATGGA
GGGGCCAAGCTAAACCGGCTAAACCCGGGGAACTACACAGCCCGGATTCAGGCCACATCTCTCTCTGGGA
ATGGGTCGTGGACAGATCCTGTGTTCTTCTATGTCCAGGCCAAAAGATATGAAAACTTCATCCATCTGAT
CATCGCTCTGCCCGTCGCTGTCCTGTTGATCGTGGGAGGGTTGGTGATTATGCTGTACGTCTTCCATAGA
AAGAGAAATAACAGCAGGCTGGGGAATGGAGTGCTGTATGCCTCTGTGAACCCGGAGTACTTCAGCGCTG
CTGATGTGTACGTTCCTGATGAGTGGGAGGTGGCTCGGGAGAAGATCACCATGAGCCGGGAACTTGGGCA
GGGGTCGTTTGGGATGGTCTATGAAGGAGTTGCCAAGGGTGTGGTGAAAGATGAACCTGAAACCAGAGTG
GCCATTAAAACAGTGAACGAGGCCGCAAGCATGCGTGAGAGGATTGAGTTTCTCAACGAAGCTTCTGTGA
TGAAGGAGTTCAATTGTCACCATGTGGTGCGATTGCTGGGTGTGGTGTCCCAAGGCCAGCCAACACTGGT
CATCATGGAACTGATGACACGGGGCGATCTCAAAAGTTATCTCCGGTCTCTGAGGCCAGAAATGGAGAAT
AATCCAGTCCTAGCACCTCCAAGCCTGAGCAAGATGATTCAGATGGCCGGAGAGATTGCAGACGGCATGG
CATACCTCAACGCCAATAAGTTCGTCCACAGAGACCTTGCTGCCCGGAATTGCATGGTAGCCGAAGATTT
CACAGTCAAAATCGGAGATTTTGGTATGACGCAGAGATATCTATGAGACAGACTATTACCGGAAGGAGGG
AAAGGGCTGCTGCCCGTGCGCTGGATGTCTCCTGAGTCCCTCAAGGATGGAGTCTTCACCACTTACTCGG
ACGTCTGGTCCTTCGGGGTCGTCCTCTGGGAGATCGCCACACTGGCCGAGCAGCCCTACCAGGGCTTGTC
CAACGAGCAAGTCCTTCGCTTCGTCATGGAGGGCGGCCTTCTGGACAAGCCAGACAACTGTCCTGACATG
CTGTTTGAACTGATGCGCATGTGCTGGCAGTATAACCCCAAGATGAGGCCTTCCTTCCTGGAGATCATCA
GCAGCATCAAAGAGGAGATGGAGCCTGGCTTCCGGGAGGTCTCCTTCTACTACAGCGAGGAGAACAAGCT
GCCCGAGCCGGAGGAGCTGGACCTGGAGCCAGAGAACATGGAGAGCGTCCCCCTGGACCCCTCGGCCTCC
TCGTCCTCCCTGCCACTGCCCGACAGACACTCAGGACACAAGGCCGAGAACGGCCCCGGCCCTGGGGTGC
TGGTCCTCCGCGCCAGCTTCGACGAGAGACAGCCTTACGCCCACATGAACGGGGGCCGCAAGAACGAGCG
GGCCTTGCCGCTGCCCCAGTCTTCGACCTGCTGATCCTTGGATCCTGAATCTGTGCAAACAGTAACGTGT
GCGCACGCGCAGCGGGGTGGGGGGGGAGAGAGAGTTTTAACAATCCATTCACAAGCCTCCTGTACCTCAG
```

Figure 1D Cont.

```
TGGATCTTCAGAACTGCCCTTGCTGCCCGCGGGAGACAGCTTCTCTGCAGTAAAACACATTTGGGATGTT
CCTTTTTTCAATATGCAAGCAGCTTTTTATTCCCTGCCCAAACCCTTAACTGACATGGGCCTTTAAGAAC
CTTAATGACAACACTTAATAGCAACAGAGCACTTGAGAACCAGTCTCCTCACTCTGTCCCTGTCCTTCCC
TGTTCTCCCTTTCTCTCTCCTCTCTGCTTCATAACGGAAAAATAATTGCCACAAGTCCAGCTGGGAAGCC
CTTTTTATCAGTTTGAGGAAGTGGCTGTCCCTGTGGCCCCATCCAACCACTGTACACACCCGCCTGACAC
CGTGGGTCATTACAAAAAAACACGTGGAGATGGAAATTTTTACCTTTATCTTTCACCTTTCTAGGGACAT
GAAATTTACAAAGGGCCATCGTTCATCCAAGGCTGTTACCATTTTAACGCTGCCTAATTTTGCCAAAATC
CTGAACTTTCTCCCTCATCGGCCCGGCGCTGATTCCTCGTGTCCGGAGGCATGGGTGAGCATGGCAGCTG
GTTGCTCCATTTGAGAGACACGCTGGCGACACACTCCGTCCATCCGACTGCCCCTGCTGTGCTGCTCAAG
GCCACAGGCACACAGGTCTCATTGCTTCTGACTAGATTATTATTTGGGGGAACTGGACACAATAGGTCTT
TCTCTCAGTGAAGGTGGGGAGAAGCTGAACCGGCTTCCCTGCCCTGCCTCCCAGCCCCCTGCCCAACCC
CCAAGAATCTGGTGGCCATGGGCCCCGAAGCAGCCTGGCGGACAGGCTTGGAGTCAAGGGGCCCCATGCC
TGCTTCTCTCCCAGCCCCAGCTCCCCCGCCCGCCCCAAGGACACAGATGGGAAGGGGTTTCCAGGGACT
CAGCCCCACTGTTGATGCAGGTTTGCAAGGAAAGAAATTCAAACACCACAACAGCAGTAAGAAGAAAAGC
AGTCAATGGATTCAAGCATTCTAAGCTTTGTTGACATTTTCTCTGTTCCTAGGACTTCTTCATGGGTCTT
ACAGTTCTATGTTAGACCATGAAACATTTGCATACACATCGTCTTTAATGTCACTTTTATAACTTTTTTA
CGGTTCAGATATTCATCTATACGTCTGTACAGAAAAAAAAAAGCTGCTATTTTTTTGTTCTTGATCTTT
GTGGATTTAATCTATGAAAACCTTCAGGTCCACCCTCTCCCCTTTCTGCTCACTCCAAGAAACTTCTTAT
GCTTTGTACTAGAGTGCGTGACTTTCTTCCTCTTTTCCCGGTAATGGATACTTCTATCACATAATTTGCC
ATGAACTGTTGGATGCCTTTTATAAATACATCCCCCATCCCTGCTCCCACCTGCCCCTTTAGTTGTTTT
CTAACCCGTAGGCTCTCTGGGCACGAGGCAGAAAGCAGGCCGGGCACCCATCCTGAGAGGGCCGCGCTCC
TCTCCCCAGCCTGCCCTCACAGCATTGGAGCCTGTTACAGTGCAAGACATGATACAAACTCAGGTCAGAA
AAACAAAGGTTAAATATTTCACACGTCTTTGTTCAGTGTTTCCACTCACCGTGGTTGAGAAGCCTCACCC
TCTCTTTCCCTTGCCTTTGCTTAGGTTGTGACACACATATATATATATTTTTTAATTCTTGGGTACAAC
AGCAGTGTTAACCGCAGACACTAGGCATTTGGATTACTATTTTTCTTAATGGCTATTTAATCCTTCCATC
CCACGAAAAACAGCTGCTGAGTCCAAGGGAGCAGCAGAGCGTGGTCCGGCAGGGCCTGTTGTGGCCCTCG
CCACCCCCTCACCGGACCGACTGACCTGTCTTTGGAACCAGAACATCCCAAGGGAACTCCTTCGCACTG
GCGTTGAGTGGGACCCCGGGATCCAGGCTGGCCCAGGGCGGCACCCTCAGGGCTGTGCCCGCTGGAGTGC
TAGGTGGAGGCAGCACAGACGCCACGGTGGCCCAAGAGCCCCTTTGCTTCTTGCTGGGGGACCAGGGCTG
TGGTGCTGGCCCACTTTCCCTCGGCCAGGAATCCAGGTCCTTGGGGCCCAGGGGTCTTGTCTTGTTTCAT
TTTTAGCACTTCTCACCAGAGAGATGACAGCACAAGAGTTGCTTCTGGGATAGAAATGTTTAGGAGTAAG
AACAAAGCTGGGATACGGTGATTGCTAGTTGTGACTGAAGATTCAACACAGAAAAGAAAGTTTATACGGC
TTTTTTGCTGGTCAGCAGTTTGTCCCACTGCTTTCTCTAGTCTCTATCCCATAGCGTGTTCCCTTTAAAA
AAAAAAAAAGGTATTATATGTAGGAGTTTTCTTTTAATTTATTTTGTGATAAATTACCAGTTTCAATCA
CTGTAGAAAAGCCCCATTATGAATTTAAATTTCAAGGAAAGGGTGTGTGTGTGTATGTGTGGGGTGTG
TGTGTGTGAGAGTGATGGGACAGTTCTTGATTTTTTGGGTTTTTTTCCCCCAAACATTTATCTACCTCA
CTCTTATTTTTTATATGTGTATATAGACAAAAGAATACATCTCACCTTTCTCAGCACCTGACAATAGGCC
GTTGATACTGGTAACCTCATCCACGCCACAGGCGCCACACCCAGGTGATGCAGGGGGAAGCCAGGCTGTA
TTCCGGGGTCAAAGCAACACTAACTCACCTCTCTGCTCATTTCAGACAGCTTGCCTTTTTCTGAGATGTC
```

Figure 1D Cont.

```
CTGTTTTGTGTTGCTTTTTTTGTTTTGTTTTCTATCTTGGTTTCCACCAAGGTGTTAGATTTCTCCTCCT
CCTAGCCAGGTGGCCCTGTGAGGCCAACGAGGGCACCAGAGCACACCTGGGGGAGCCACCAGGCTGTCCC
TGGCTGGTTGTCTTTGGAACAAACTGCTTCTGTGCAGATGGAATGACCAACACATTTCGTCCTTAAGAGA
GCAGTGGTTCCTCAGGTTCTGAGGAGAGGAAGGTGTCCAGGCAGCACCATCTCTGTGCGAATCCCCAGGG
TAAAGGCGTGGGGCATTGGGTTTGCTCCCCTTGCTGCTGCTCCATCCCTGCAGGAGGCTCGCGCTGAGGC
AGGACCGTGCGGCCATGGCTGCTGCATTCATTGAGCACAAAGGTGCAGCTGCAGCAGCAGCTGGAGAGCA
AGAGTCACCCAGCCTGTGCGCCAGAATGCAGAGGCTCCTGACCTCACAGCCAGTCCCTGATAGAACACAC
GCAGGAGCAGAGTCCCCTCCCCCTCCAGGCTGCCCTCTCAACTTCTCCCTCACCTCCTTCCCTAGGGGTA
GACAGAGATGTACCAAACCTTCCGGCTGGAAAGCCCAGTGGCCGGCGCCGAGGCTCGTGGCGTCACGCCC
CCCCCGCCAGGGCTGTACCTCCGTCTCCCTGGTCCTGCTGCTCACAGGACAGACGGCTCGCTCCCCTCTT
CCAGCAGCTGCTCTTACAGGCACTGATGATTTCGCTGGGAAGTGTGGCGGGCAGCTTTGCCTAAGCGTGG
ATGGCTCCTCGGCAATTCCAGCCTAAGTGAAGGCGCTCAGGAGCCTCCTGCTGGAACGCGACCCATCTCT
CCCAGGACCCCGGGGATCTTAAGGTCATTGAGAAATACTGTTGGATCAGGGTTTTGTTCTTCCACACTGT
AGGTGACCCCTTGGAATAACGGCCTCTCCTCTCGTGCACATACCTACCGGTTTCCACAACTGGATTTCTA
CAGATCATTCAGCTGGTTATAAGGGTTTTGTTTAAACTGTCCGAGTTACTGATGTCATTTGTTTTTGTT
TTATGTAGGTAGCTTTTAAGTAGAAAACACTAACAGTGTAGTGCCCATCATAGCAAATGCTTCAGAAACA
CCTCAATAAAAGAGAAAACTTGGCTTGTGTGATGGTGCAGTCACTTTACTGGACCAACCCACCCACCTTG
ACTATACCAAGGCATCATCTATCCACAGTTCTAGCCTAACTTCATGCTGATTTCTCTGCCTCTTGATTTT
TCTCTGTGTGTTCCAAATAATCTTAAGCTGAGTTGTGGCATTTTCCATGCAACCTCCTTCTGCCAGCAGC
TCACACTGCTTGAAGTCATATGAACCACTGAGGCACATCATGGAATTGATGTGAGCATTAAGACGTTCTC
CCACACAGCCCTTCCCTGAGGCAGCAGGAGCTGGTGTGTACTGGAGACACTGTTGAACTTGATCAAGACC
CAGACCACCCCAGGTCTCCTTCGTGGGATGTCATGACGTTTGACATACCTTTGGAACGAGCCTCCTCCTT
GGAAGATGGAAGACCGTGTTCGTGGCCGACCTGGCCTCTCCTGGCCTGTTTCTTAAGATGCGGAGTCACA
TTTCAATGGTACGAAAAGTGGCTTCGTAAAATAGAAGAGCAGTCACTGTGGAACTACCAAATGGCGAGAT
GCTCGGTGCACATTGGGGTGCTTTGGGATAAAAGATTTATGAGCCAACTATTCTCTGGCACCAGATTCTA
GGCCAGTTTGTTCCACTGAAGCTTTTCCCACAGCAGTCCACCTCTGCAGGCTGGCAGCCGAATGGCTTGC
CAGTGGCTCTGTGGCAAGATCACACTGAGATCGATGGGTGAGAAGGCTAGGATGCTTGTCTAGTGTTCTT
AGCTGTCACGTTGGCTCCTTCCAGGGTGGCCAGACGGTGTTGGCCACTCCCTTCTAAAACACAGGCGCCC
TCCTGGTGACAGTGACCCGCCGTGGTATGCCTTGGCCCATTCCAGCAGTCCCAGTTATGCATTTCAAGTT
TGGGGTTTGTTCTTTTCGTTAATGTTCCTCTGTGTTGTCAGCTGTCTTCATTTCCTGGGCTAAGCAGCAT
TGGGAGATGTGGACCAGAGATCCACTCCTTAAGAACCAGTGGCGAAAGACACTTTCTTTCTTCACTCTGA
AGTAGCTGGTGGTACAAATGAGAACTTCAAGAGAGGATGTTATTTAGACTGAACCTCTGTTGCCAGAGAT
GCTGAAGATACAGACCTTGGACAGGTCAGAGGGTTTCATTTTGGCCTTCATCTTAGATGACTGGTTGCG
TCATTTGGAGAAGTGAGTGCTCCTTGATGGTGGAATGACCGGGTGGTGGGTACAGAACCATTGTCACAGG
GATCCTGGCACAGAGAAGAGTTACGAGCAGCAGGGTGCAGGGCTTGGAAGGAATGTGGGCAAGGTTTTGA
ACTTGATTGTTCTTGAAGCTATCAGACCACATCGAGGCTCAGCAGTCATCCGTGGGCATTTGGTTTCAAC
AAAGAAACCTAACATCCTACTCTGGAAACTGATCTCGGAGTTAAGGCGAATTGTTCAAGAACACAAACTA
CATCGCACTCGTCAGTTGTCAGTTCTGGGGCATGACTTTAGCGTTTTGTTCTGCGAGAACATAACGATC
ACTCATTTTTATGTCCCACGTGTGTGTGTCCGCATCTTTCTGGTCAACATTGTTTTAACTAGTCACTCAT
```

Figure 1D Cont.

```
TAGCGTTTTCAATAGGGCTCTTAAGTCCAGTAGATTACGGGTAGTCAGTTGACGAAGATCTGGTTTACAA
GAACTAATTAAATGTTTCATTGCATTTTTGTAAGAACAGAATAATTTTATAAAATGTTTGTAGTTTATAA
TTGCCGAAAATAATTTAAAGACACTTTTTTTTTCTCTGTGTGTGCAAATGTGTGTTTGTGATCCATTTTT
TTTTTTTTTTTTAGGACACCTGTTACTAGCTAGCTTTACAATATGCCAAAAAAGGATTTCTCCCTGAC
CCCATCCGTGGTTCACCCTCTTTTCCCCCATGCTTTTTGCCCTAGTTTATAACAAAGGAATGATGATGA
TTTAAAAAGTAGTTCTGTATCTTCAGTATCTTGGTCTTCCAGAACCCTCTGGTTGGGAAGGGGATCATTT
TTTACTGGTCATTTCCCTTTGGAGTGTAGCTACTTTAACAGATGGAAAGAACCTCATTGGCCATGGAAAC
AGCCGAGGTGTTGGAGCCCAGCAGTGCATGGCACCGTTCGGCATCTGGCTTGATTGGTCTGGCTGCCGTC
ATTGTCAGCACAGTGCCATGGACATGGGAAGACTTGACTGCACAGCCAATGGTTTTCATGATGATTACAG
CATACACAGTGATCACATAAACGATGACAGCTATGGGCACACAGGCCATTTGCTTACATGCCTCGTATC
ATGACTGATTACTGCTTTGTTAGAACACAGAAGAGACCCTATTTTATTTAAGGCAGAACCCCGAAGATAC
GTATTTCCAATACAGAAAAGAATTTTTAATAAAAACTATAACATACACAAAAATTGGTTTTAAAGTTGAC
TCCACTTCCTCTAACTCCAGTGGATTGTTGGCCATGTCTCCCCAACTCCACAATATCTCTATCATGGGAA
ACACCTGGGGTTTTTGCGCTACATAGGAGAAAGATCTGGAAACTATTTGGGTTTTGTTTTCAACTTTTCA
TTTGGATGTTTGGCGTTGCACACACACATCCACCGGTGGAAGAGACGCCCGGTGAAAACACCTGTCTGCT
TTCTAAGCCAGTGAGGTTGAGGTGAGAGGTTTGCCAGAGTTTGTCTACCTCTGGGTATCCCTTTGTCTGG
GATAAAAAAAATCAAACCAGAAGGCGGGATGGAATGGATGCACCGCAAATAATGCATTTTCTGAGTTTTC
TTGTTAAAAAAAATTTTTTAAGTAAGAAAAAAAAAGGTAATAACATGGCCAATTTGTTACATAAAATG
ACTTTCTGTGTATAAATTATTCCTAAAAAATCCTGTTTATATAAAAAATCAGTAGATGAAAAAAATTTCA
AAATGTTTTGTATATTCTGTTGTAAGAATTTATTCCTGTTATTGCGATATACTCTGGATTCTTTACATA
ATGGAAAAAGAAACTGTCTATTTTGAATGGCTGAAGCTAAGGCAACGTTAGTTTCTCTTACTCTGCTTT
TTTCTAGTAAAGTACTACATGGTTTAAGTTAAATAAAATAATTCTGTATGCAAAAAAAAAAAAAAAAA
AAAAAAAA
```

Figure 1D Cont.

SEQ ID NO: 7:

IGF-1R Protein Sequence, Accession number NP 000866.1, isoform 1 precursor

MKSGSGGGSPTSLWGLLFLSAALSLWPTSGEICGPGIDIRNDYQQLKRLENCTVIEGYLHILLISKAEDY
RSYRFPKLTVITEYLLLFRVAGLESLGDLFPNLTVIRGWKLFYNYALVIFEMTNLKDIGLYNLRNITRGA
IRIEKNADLCYLSTVDWSLILDAVSNNYIVGNKPPKECGDLCPGTMEEKPMCEKTTINNEYNYRCWTTNR
CQKMCPSTCGKRACTENNECCHPECLGSCSAPDNDTACVACRHYYYAGVCVPACPPNTYRFEGWRCVDRD
FCANILSAESSDSEGFVIHDGECMQECPSGFIRNGSQSMYCIPCEGPCPKVCEEEKKTKTIDSVTSAQML
QGCTIFKGNLLINIRRGNNIASELENFMGLIEVVTGYVKIRHSHALVSLSFLKNLRLILGEEQLEGNYSF
YVLDNQNLQQLWDWDHRNLTIKAGKMYFAFNPKLCVSEIYRMEEVTGTKGRQSKGDINTRNNGERASCES
DVLHFTSTTTSKNRIIITWHRYRPPDYRDLISFTVYYKEAPFKNVTEYDGQDACGSNSWNMVDVDLPPNK
DVEPGILLHGLKPWTQYAVYVKAVTLTMVENDHIRGAKSEILYIRTNASVPSIPLDVLSASNSSSQLIVK
WNPPSLPNGNLSYYIVRWQRQPQDGYLYRHNYCSKDKIPIRKYADGTIDIEEVTENPKTEVCGGEKGPCC
ACPKTEAEKQAEKEEAEYRKVFENFLHNSIFVPRPERKRRDVMQVANTTMSSRSRNTTAADTYNITDPEE
LETEYPFFESRVDNKERTVISNLRPFTLYRIDIHSCNHEAEKLGCSASNFVFARTMPAEGADDIPGPVTW
EPRPENSIFLKWPEPENPNGLILMYEIKYGSQVEDQRECVSRQEYRKYGGAKLNRLNPGNYTARIQATSL
SGNGSWTDPVFFYVQAKTGYENFIHLIIALPVAVLLIVGGLVIMLYVFHRKRNNSRLGNGVLYASVNPEY
FSAADVYVPDEWEVAREKITMSRELGQGSFGMVYEGVAKGVVKDEPETRVAIKTVNEAASMRERIEFLNE
ASVMKEFNCHHVVRLLGVVSQGQPTLVIMELMTRGDLKSYLRSLRPEMENNPVLAPPSLSKMIQMAGEIA
DGMAYLNANKFVHRDLAARNCMVAEDFTVKIGDFGMTRDIYETDYYRKGGKGLLPVRWMSPESLKDGVFT
TYSDVWSFGVVLWEIATLAEQPYQGLSNEQVLRFVMEGGLLDKPDNCPDMLFELMRMCWQYNPKMRPSFL
EIISSIKEEMEPGFREVSFYYSEENKLPEPEELDLEPENMESVPLDPSASSSSLPLPDRHSGHKAENGPG
PGVLVLRASFDERQPYAHMNGGRKNERALPLPQSSTC

Figure 1E

SEQ ID NO: 8:

IGF-1R Protein Sequence, Accession number NP 001278787.1, isoform 2 precursor

MKSGSGGGSPTSLWGLLFLSAALSLWPTSGEICGPGIDIRNDYQQLKRLENCTVIEGYLHILLISKAEDY
RSYRFPKLTVITEYLLLFRVAGLESLGDLFPNLTVIRGWKLFYNYALVIFEMTNLKDIGLYNLRNITRGA
IRIEKNADLCYLSTVDWSLILDAVSNNYIVGNKPPKECGDLCPGTMEEKPMCEKTTINNEYNYRCWTTNR
CQKMCPSTCGKRACTENNECCHPECLGSCSAPDNDTACVACRHYYAGVCVPACPPNTYRFEGWRCVDRD
FCANILSAESSDSEGFVIHDGECMQECPSGFIRNGSQSMYCIPCEGPCPKVCEEEKKTKTIDSVTSAQML
QGCTIFKGNLLINIRRGNNIASELENFMGLIEVVTGYVKIRHSHALVSLSFLKNLRLILGEEQLEGNYSF
YVLDNQNLQQLWDWDHRNLTIKAGKMYFAFNPKLCVSEIYRMEEVTGTKGRQSKGDINTRNNGERASCES
DVLHFTSTTTSKNRIIITWHRYRPPDYRDLISFTVYYKEAPFKNVTEYDGQDACGSNSWNMVDVDLPPNK
DVEPGILLHGLKPWTQYAVYVKAVTLTMVENDHIRGAKSEILYIRTNASVPSIPLDVLSASNSSSQLIVK
WNPPSLPNGNLSYYIVRWQRQPQDGYLYRHNYCSKDKIPIRKYADGTIDIEEVTENPKTEVCGGEKGPCC
ACPKTEAEKQAEKEEAEYRKVFENFLHNSIFVPRPERKRRDVMQVANTTMSSRSRNTTAADTYNITDPEE
LETEYPFFESRVDNKERTVISNLRPFTLYRIDIHSCNHEAEKLGCSASNFVFARTMPAEGADDIPGPVTW
EPRPENSIFLKWPEPENPNGLILMYEIKYGSQVEDQRECVSRQEYRKYGGAKLNRLNPGNYTARIQATSL
SGNGSWTDPVFFYVQAKRYENFIHLIIALPVAVLLIVGGLVIMLYVFHRKRNNSRLGNGVLYASVNPEYF
SAADVYVPDEWEVAREKITMSRELGQGSFGMVYEGVAKGVVKDEPETRVAIKTVNEAASMRERIEFLNEA
SVMKEFNCHHVVRLLGVVSQGQPTLVIMELMTRGDLKSYLRSLRPEMENNPVLAPPSLSKMIQMAGEIAD
GMAYLNANKFVHRDLAARNCMVAEDFTVKIGDFGMTRDIYETDYYRKGGKGLLPVRWMSPESLKDGVFTT
YSDVWSFGVVLWEIATLAEQPYQGLSNEQVLRFVMEGGLLDKPDNCPDMLFELMRMCWQYNPKMRPSFLE
IISSIKEEMEPGFREVSFYYSEENKLPEPEELDLEPENMESVPLDPSASSSSLPLDRHSGHKAENGPGP
GVLVLRASFDERQPYAHMNGGRKNERALPLPQSSTC

SEQ ID NO: 9:

siRNA 1 sense strand, uppercase = RNA, lower case = DNA

UGGUAUCUCCUCUAAGUAAtt

SEQ ID NO: 10:

siRNA 2 sense strand, uppercase = RNA, lower case = DNA

CGAGCAAGGUCCUUCCAUAtt

Figure 1F

SEQ ID NO: 11:

siRNA 1 antisense strand, uppercase = RNA, lower case = DNA

UUACUUAGAGGAGAUACCAgc

SEQ ID NO: 12:

siRNA 2 antisense strand, uppercase = RNA, lower case = DNA

UAUGGAAGGACCUUGCUCGca

SEQ ID NOs: 13 and 14:

Human IGFBP7: Primer Pair 1 actggctgggtgctggta (SEQ ID NO: 13)    tggatgcatggcactcata (SEQ ID NO: 14)

SEQ ID NOs: 15 and 16:

Human IGFBP7: Primer Pair 2 gaatcccgacacctgtcctc (SEQ ID NO: 15)    cagcacccagccagttactt (SEQ ID NO: 16)

SEQ ID NOs: 17 and 18:

Human HPRT1: Primer Pair tgacactggcaaaacaatgca (SEQ ID NO: 17)    ggtcctttcaccagcaagct (SEQ ID NO: 18)

SEQ ID NOs: 19 and 20:

Human NPPB: Primer Pair caccgcaaaatggtcctcta (SEQ ID NO: 19)    gtccatcttcctcccaaagc (SEQ ID NO: 20)

Figure 1G

SEQ ID NOs: 21 and 22:

Human Tp53: Primer Pair cagcacatgacggaggttgt (SEQ ID NO: 21)     tcatccaaatactccacacgc (SEQ ID NO: 22)

SEQ ID NOs: 23 and 24:

Human p21: Primer Pair tgtccgtcagaacccatgc (SEQ ID NO: 23)     Aaagtcgaagttccatcgctc (SEQ ID NO: 24)

SEQ ID NOs: 25 and 26:

Mouse Nppa: Primer Pair gcttccaggccatattggag (SEQ ID NO: 25)     gggggcatgacctcatctt (SEQ ID NO: 26)

SEQ ID NOs: 27 and 28:

Mouse Nppb: Primer Pair gaggtcactcctatcctctgg (SEQ ID NO: 27)     gccatttcctccgactttctc (SEQ ID NO: 28)

SEQ ID NOs: 29 and 30:

Mouse Trp53: Primer Pair cacgtactctcctcccctcaat (SEQ ID NO: 29)     aactgcacagggcacgtctt (SEQ ID NO: 30)

SEQ ID NOs: 31 and 32:

Mouse Myh6: Primer Pair tgcactacggaaacatgaagtt (SEQ ID NO: 31)     cgatggaatagtacacttgctgt (SEQ ID NO: 32)

Figure 1H

SEQ ID NOs: 33 and 34:

Mouse Myh7: Primer Pair actgtcaacacttaagagggtca (SEQ ID NO: 33)    ttggatgatttgatcttccaggg (SEQ ID NO: 34)

SEQ ID NOs: 35 and 36:

Mouse Hprt1: Primer Pair gctgacctgctggattacat (SEQ ID NO: 35)    ttggggctgtactgcttaac (SEQ ID NO: 36)

SEQ ID NO: 37:

hIGFBP7-CDS Plasmid

ATGGAACGGCCTAGCCTGAGAGCCCTGCTGCTGGGAGCTGCTGGACTTCTCCTTCTG
CTGCTGCCCCTGAGCAGCTCCAGCTCCTCTGATACCTGTGGCCCTTGCGAGCCTGCC
AGCTGTCCTCCTCTGCCTCCACTGGGATGTCTGCTGGGCGAGACAAGAGATGCCTGC
GGCTGCTGTCCATGTGCGCTAGAGGCGAGGGCGAACCTTGTGGCGGAGGCGGAGC
TGGCAGAGGCTATTGTGCCCCTGGCATGGAATGCGTGAAGTCCCGGAAGCGGAGAA
AGGGCAAAGCCGGCGCTGCTGCAGGCGGACCTGGCGTGTCAGGCGTGTGTGTGTGC
AAGAGCAGATACCCCGTGTGCGGCTCCGACGGCACCACATATCCAAGCGGCTGTCA
GCTGAGGGCCGCCTCAGAGAGCCGAGAGCAGAGGCGAGAAGGCCATCACCCAG
GTGTCCAAGGGCACATGCGAGCAGGGCCCTAGCATCGTGACCCCCCCAAGGACAT
CTGGAACGTGACAGGCGCCCAGGTGTACCTGAGCTGCGAAGTGATCGGCATCCCCA
CCCCCGTGCTGATCTGGAACAAAGTGAAGCGGGGCCACTACGGCGTGCAGAGAACA
GAACTGCTGCCCGGCGACAGAGACAACCTGGCCATCCAGACAAGAGGCGGACCCGA
GAAGCACGAAGTGACCGGATGGGTGCTGGTGTCCCCCTGTCCAAAGAGGATGCCG
GCGAGTACGAGTGCCACGCCAGCAATTCTCAGGGCCAGGCCAGCGCCAGTGCCAAG
ATCACAGTGGTGGATGCCCTGCACGAGATCCCCGTGAAGAAGGCGAAGGCGCCGA
GCTG

Figure 11

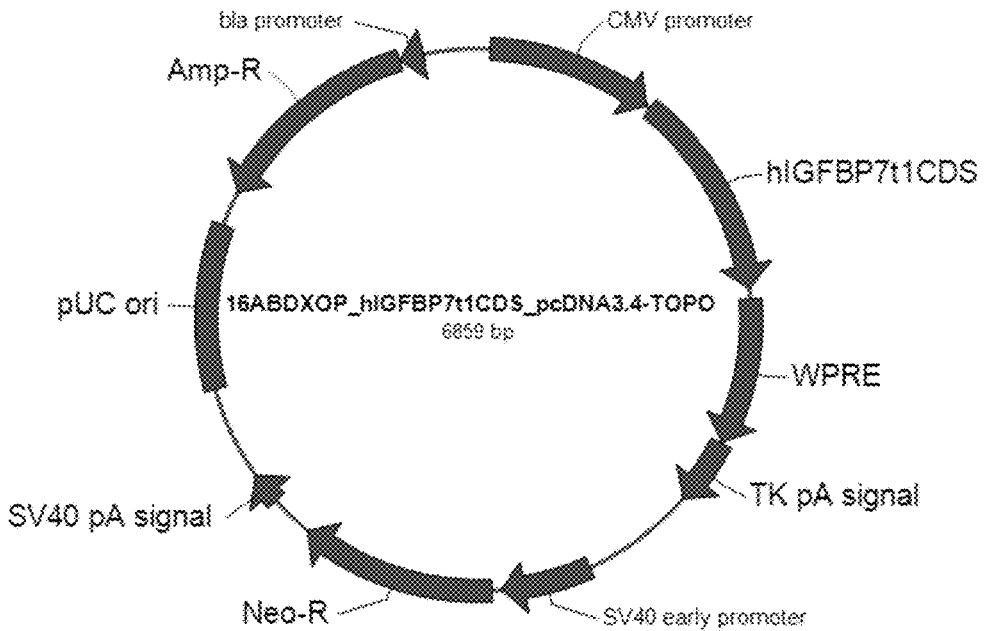

SEQ ID NO: 38:

hIGFBP7-CDS-6xHis Plasmid

ATGGAACGGCCTAGCCTGAGAGCCCTGCTGCTGGGAGCTGCTGGACTTCTCCTTCTG
CTGCTGCCCCTGAGCAGCTCCAGCTCCTCTGATACCTGTGGCCCTTGCGAGCCTGCC
AGCTGTCCTCCTCTGCCTCCACTGGGATGTCTGCTGGGCGAGACAAGAGATGCCTGC
GGCTGCTGTCCATGTGCGCTAGAGGCGAGGGCGAACCTTGTGGCGGAGGCGGAGC
TGGCAGAGGCTATTGTGCCCCTGGCATGGAATGCGTGAAGTCCCGGAAGCGGAGAA
AGGGCAAAGCCGGCGCTGCTGCAGGCGGACCTGGCGTGTCAGGCGTGTGTGTGTGC
AAGAGCAGATACCCCGTGTGCGGCTCCGACGGCACCACATATCCAAGCGGCTGTCA
GCTGAGGGCCGCCTCTCAGAGAGCCGAGAGCAGAGGCGAGAAGGCCATCACCCAG
GTGTCCAAGGGCACATGCGAGCAGGGCCCTAGCATCGTGACCCCCCCAAGGACAT
CTGGAACGTGACAGGCGCCCAGGTGTACCTGAGCTGCGAAGTGATCGGCATCCCCA
CCCCCGTGCTGATCTGGAACAAAGTGAAGCGGGGCCACTACGGCGTGCAGAGAACA
GAACTGCTGCCCGGCGACAGAGACAACCTGGCCATCCAGACAAGAGGCGGACCCGA
GAAGCACGAAGTGACCGGATGGGTGCTGGTGTCCCCCTGTCCAAAGAGGATGCCG
GCGAGTACGAGTGCCACGCCAGCAATTCTCAGGGCCAGGCCAGCGCCAGTGCCAAG
ATCACAGTGGTGGATGCCCTGCACGAGATCCCCGTGAAGAAAGGCGAAGGCGCCGA
GCTGCATCACCATCACCATCACGTTTAA

Figure 1J

SEQ ID NO: 39

(shRNA targeting IGFBP7)

5'-CCGG-GCTGGTATCTCCTCTAAGTAACTCGAGTTACTTAGAGGAGATACCAGC-TTTTTG-3'

SEQ ID NO: 40:

(shRNA targeting sequence)

GCTGGTATCTCCTCTAAGTAA

SEQ ID NO: 41:

(shRNA hairpin loop sequence)

CTCGAG

SEQ ID NO: 42:

(sequence terminating the shRNA expression for U6 promoter)

TTTTT

SEQUENCE LISTING

```
<160> NUMBER OF SEQ ID NOS: 42

<210> SEQ ID NO 1
<211> LENGTH: 1137
<212> TYPE: DNA
<213> ORGANISM: Homo Sapien

<400> SEQUENCE: 1
actcgcgccc ttgccgctgc caccgcaccc cgccatggag cggccgtcgc tgcgcgccct      60
gctcctcggc gccgctgggc tgctgctcct gctcctgccc ctctcctctt cctcctcttc     120
ggacacctgc ggcccctgcg agccggcctc ctgcccgccc ctgcccccgc tgggctgcct     180
gctgggcgag acccgcgacg cgtgcggctg ctgccctatg tgcgcccgcg gcgagggcga     240
gccgtgcggg ggtggcggcg ccggcagggg gtactgcgcg ccgggcatgg agtgcgtgaa     300
gagccgcaag aggcggaagg gtaaagccgg ggcagcagcc ggcggtccgg gtgtaagcgg     360
cgtgtgcgtg tgcaagagcc gctacccggt gtgcggcagc gacggcacca cctacccgag     420
cggctgccag ctgcgcgccg ccagccagag ggccgagagc cgcggggaga aggccatcac     480
ccaggtcagc aagggcacct gcgagcaagg tccttccata gtgacgcccc caaggacat      540 ctggaatgtc actggtgccc aggtgtactt gagctgtgag gtcatcggaa tcccgacacc     600
tgtcctcatc tggaacaagg taaaaagggg tcactatgga gttcaaagga cagaactcct     660
gcctggtgac cgggacaacc tggccattca gacccggggt ggcccagaaa agcatgaagt     720
aactggctgg gtgctggtat ctcctctaag taaggaagat gctggagaat atgagtgcca     780
tgcatccaat tcccaaggac aggcttcagc atcagcaaaa attacagtgg ttgatgcctt     840
acatgaaata ccagtgaaaa aaggtgaagg tgccgagcta taaacctcca gaatattatt     900
agtctgcatg gttaaaagta gtcatggata actacattac ctgttcttgc ctaataagtt     960
```

-continued

```
tcttttaatc caatccacta acactttagt tatattcact ggttttacac agagaaatac      1020
aaaataaaga tcacacatca agactatcta caaaaattta ttatatattt acagaagaaa      1080
agcatgcata tcattaaaca aataaaatac tttttatcac aacacagtaa aaaaaaa         1137
```

<210> SEQ ID NO 2
<211> LENGTH: 1051
<212> TYPE: DNA
<213> ORGANISM: Homo Sapien

<400> SEQUENCE: 2

```
actcgcgccc ttgccgctgc caccgcaccc cgccatggag cggccgtcgc tgcgcgccct        60
gctcctcggc gccgctgggc tgctgctcct gctcctgccc ctctcctctt cctcctcttc       120
ggacacctgc ggcccctgcg agccggcctc ctgcccgccc ctgcccccgc tgggctgcct       180
gctgggcgag acccgcgacg cgtgcggctg ctgccctatg tgcgcccgcg gcgagggcga       240
gccgtgcggg ggtggcggcg ccggcagggg gtactgcgcg ccgggcatgg agtgcgtgaa       300
gagccgcaag aggcggaagg gtaaagccgg ggcagcagcc ggcggtccgg gtgtaagcgg       360
cgtgtgcgtg tgcaagagcc gctacccggt gtgcggcagc gacggcacca cctacccgag       420
cggctgccag ctgcgcgccg ccagccagag ggccgagagc cgcggggaga aggccatcac       480
ccaggtcagc aagggcacct gcgagcaagg tccttccata gtgacgcccc caaggacat       540 ctggaatgtc actggtgccc aggtgtactt gagctgtgag gtcatcggaa tcccgacacc       600
tgtcctcatc tggaacaagg taaaaagggg tcactatgga gttcaaagga cagaactcct       660
gcctggtgac cgggacaacc tggccattca gacccggggt ggcccagaaa agcatgaagt       720
aactggctgg gtgctggtat ctcctctaag taaggaagat gctggagaat atgagtgcca       780
tgcatccaat tcccaaggac aggcttcagc atcagcaaaa attacagtgg ttgatgcctt       840
acatgaaata ccagtgaaaa aaggtacaca ataaatctca cagccattta aaaatgacta       900
gtacatttgc tttaaaaaga acagaactaa gtatgaaagt atcagacgta gctattgatg       960
aaattctgta gttagcaacc cataagggca ttaagtatgc cattaaaatg tacagcatga      1020
gactccaaaa gattatctgg atgggtgact g                                     1051
```

<210> SEQ ID NO 3
<211> LENGTH: 282
<212> TYPE: PRT
<213> ORGANISM: Homo Sapien

<400> SEQUENCE: 3

```
Met Glu Arg Pro Ser Leu Arg Ala Leu Leu Leu Gly Ala Ala Gly Leu
1               5                   10                  15

Leu Leu Leu Leu Pro Leu Ser Ser Ser Ser Ser Ser Asp Thr Cys
            20                  25                  30

Gly Pro Cys Glu Pro Ala Ser Cys Pro Pro Leu Pro Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110
```

Cys Lys Ser Arg Tyr Pro Val Cys Gly Ser Asp Gly Thr Thr Tyr Pro
            115                 120                 125

Ser Gly Cys Gln Leu Arg Ala Ala Ser Gln Arg Ala Glu Ser Arg Gly
            130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
            165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
            195                 200                 205

Leu Pro Gly Asp Arg Asp Asn Leu Ala Ile Gln Thr Arg Gly Gly Pro
            210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
            245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
            275                 280

<210> SEQ ID NO 4
<211> LENGTH: 279
<212> TYPE: PRT
<213> ORGANISM: Homo Sapien

<400> SEQUENCE: 4

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
            20                  25                  30

Gly Pro Cys Glu Pro Ala Ser Cys Pro Pro Leu Pro Pro Leu Gly Cys
            35                  40                  45

Leu Leu Gly Glu Thr Arg Asp Ala Cys Gly Cys Cys Pro Met Cys Ala
            50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
            85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
            115                 120                 125

Ser Gly Cys Gln Leu Arg Ala Ala Ser Gln Arg Ala Glu Ser Arg Gly
            130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
            165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu

|  | 195 |  | 200 |  | 205 |  |
|---|---|---|---|---|---|---|

Leu Pro Gly Asp Arg Asp Asn Leu Ala Ile Gln Thr Arg Gly Gly Pro
    210                         215                      220

Glu Lys His Glu Val Thr Gly Trp Val Leu Val Ser Pro Leu Ser Lys
225                     230                     235                240

Glu Asp Ala Gly Glu Tyr Glu Cys His Ala Ser Asn Ser Gln Gly Gln
                245                     250                     255

Ala Ser Ala Ser Ala Lys Ile Thr Val Val Asp Ala Leu His Glu Ile
            260                     265                     270

Pro Val Lys Lys Gly Thr Gln
       275

<210> SEQ ID NO 5
<211> LENGTH: 12262
<212> TYPE: DNA
<213> ORGANISM: Homo Sapien

<400> SEQUENCE: 5

```
agtgtgtggc agcggcggcg gcggcgcggc gaggctgggg ctcttgttta ccagcattaa      60
ctccgctgag cggaaaaaaa aagggaaaaa acccgaggag gagcgagcgc accaggcgaa     120
ctcgagagag gcgggagagc gagagggacg ccgccagcga gcctgcccac ggccggcgct     180
cgcagaccct cggccccgct ccccggatcc ccccgcgccc tccacgcccc tcccgcgcgg     240
gggcagctcc acgcgcgcc tcgcctcggc tgtgaccttc agcgagccgg agccccgcg      300
cagagcaggc ggcggcggc gggggccggg cggggccgg cgcggggcgg gcggcggcgc      360
agagccgggc ggcgcggcgg gagtgctgag cgcggcgcgg ccggcccgcc gctttgtgtg     420
tgtcctggat ttgggaagga gctcgccgcg gcggcggcgg cgctgaggga ggaggcggcg     480
gcgagcggag ccaggaggag gaggaggagg gggagccgct cattcatttt gactccgcgt     540
ttctgcccct cgccggcctc gcctgtgacc cggacttcgg ggcgatcttg cgaactgcgt     600
cgcgccctcc cgcggcggaa gctcgggcgt ccggccgcct ccgcgcggc cagggccggg     660
cttgttttc ctcgcctagg cagatttggg cttttgccccc tttctttgca gtttttcccc     720
cttcctgcct ctccgggttt gaaaatggag gccgacgacg ccgacagccc gccccggcgc     780
gcctcgggtt cccgactccg ccgagccctg ggccgctgct gccggcgctg aggggccgcc     840
ccgcgccgcc cgccccgtcc gcgcaccccgg agggcccccgg cggcgccgcc ttcggagtat     900
tgtttccttc gccccttgttt ttggaggggg agcgaagact gagtttgaga cttgtttcct     960
ttcatttcct tttttttctt tcttttcttt tttttttttt tttttttttt tgagaaaggg    1020
gaatttcatc ccaaataaaa ggaatgaagt ctggctccgg aggagggtcc ccgacctcgc    1080
tgtggggct cctgtttctc tccgccgcgc tctcgctctg gccgacgagt ggagaaatct    1140
gcgggccagg catcgacatc cgcaacgact atcagcagct gaagcgcctg gagaactgca    1200
cggtgatcga gggctacctc cacatcctgc tcatctccaa ggccgaggac taccgcagct    1260
accgcttccc caagctcacg gtcattaccg agtacttgct gctgttccga gtggctggcc    1320
tcgagagcct cggagacctc ttcccccaacc tcacggtcat ccgcggctgg aaactcttct    1380
acaactacgc cctggtcatc ttcgagatga ccaatctcaa ggatattggg ctttacaacc    1440
tgaggaacat tactcggggg gccatcagga ttgagaaaaa tgctgacctc tgttacctct    1500
ccactgtgga ctggtccctg atcctggatg cggtgtccaa taactacatt gtggggaata    1560
agcccccaaa ggaatgtggg gacctgtgtc cagggaccat ggaggagaag ccgatgtgtg    1620
```

```
agaagaccac catcaacaat gagtacaact accgctgctg gaccacaaac cgctgccaga    1680
aaatgtgccc aagcacgtgt gggaagcggg cgtgcaccga gaacaatgag tgctgccacc    1740
ccgagtgcct gggcagctgc agcgcgcctg acaacgacac ggcctgtgta gcttgccgcc    1800
actactacta tgccggtgtc tgtgtgcctg cctgcccgcc caacacctac aggtttgagg    1860
gctggcgctg tgtggaccgt gacttctgcg ccaacatcct cagcgccgag agcagcgact    1920
ccgaggggtt tgtgatccac gacggcgagt gcatgcagga gtgccctcg ggcttcatcc     1980 gcaacggcag ccagagcatg tactgcatcc cttgtgaagg tccttgcccg aaggtctgtg    2040
aggaagaaaa gaaaacaaag accattgatt ctgttacttc tgctcagatg ctccaaggat    2100
gcaccatctt caagggcaat ttgctcatta acatccgacg ggggaataac attgcttcag    2160
agctggagaa cttcatgggg ctcatcgagg tggtgacggg ctacgtgaag atccgccatt    2220
ctcatgcctt ggtctccttg tccttcctaa aaaaccttcg cctcatccta ggagaggagc    2280
agctagaagg gaattactcc ttctacgtcc tcgacaacca gaacttgcag caactgtggg    2340
actgggacca ccgcaacctg accatcaaag cagggaaaat gtactttgct ttcaatccca    2400
aattatgtgt ttccgaaatt taccgcatgg aggaagtgac ggggactaaa gggcgccaaa    2460
gcaaggggga cataaacacc aggaacaacg gggagagagc ctcctgtgaa agtgacgtcc    2520
tgcatttcac ctccaccacc acgtcgaaga atcgcatcat cataacctgg caccggtacc    2580 ggcccctga ctacagggat ctcatcagct tcaccgttta ctacaaggaa gcacccttta     2640
agaatgtcac agagtatgat gggcaggatg cctgcggctc caacagctgg aacatggtgg    2700
acgtggacct cccgcccaac aaggacgtgg agcccggcat cttactacat gggctgaagc    2760
cctggactca gtacgccgtt tacgtcaagg ctgtgaccct caccatggtg gagaacgacc    2820
atatccgtgg ggccaagagt gagatcttgt acattcgcac caatgcttca gttccttcca    2880
ttcccttgga cgttctttca gcatcgaact cctcttctca gttaatcgtg aagtggaacc    2940
ctccctctct gcccaacggc aacctgagtt actacattgt gcgctggcag cggcagcctc    3000
aggacggcta cctttaccgg cacaattact gctccaaaga caaaatcccc atcaggaagt    3060
atgccgacgg caccatcgac attgaggagg tcacagagaa ccccaagact gaggtgtgtg    3120
gtggggagaa agggccttgc tgcgcctgcc ccaaaactga agccgagaag caggccgaga    3180
aggaggaggc tgaataccgc aaagtctttg agaatttcct gcacaactcc atcttcgtgc    3240
ccagacctga aggaagcgg agagatgtca tgcaagtggc caacaccacc atgtccagcc     3300
gaagcaggaa caccacggcc gcagacacct acaacatcac cgacccggaa gagctggaga    3360
cagagtaccc tttctttgag agcagagtgg ataacaagga gagaactgtc atttctaacc    3420
ttcggccttt cacattgtac cgcatcgata tccacagctg caaccacgag gctgagaagc    3480
tgggctgcag cgcctccaac ttcgtctttg caaggactat gcccgcagaa ggagcagatg    3540
acattcctgg gccagtgacc tgggagccaa ggcctgaaaa ctccatcttt ttaaagtggc    3600
cggaacctga gaatcccaat ggattgattc taatgtatga aataaaatac ggatcacaag    3660
ttgaggatca gcgagaatgt gtgtccagac aggaatacag gaagtatgga ggggccaagc    3720
taaaccggct aaacccgggg aactacacag cccggattca ggccacatct ctctctggga    3780
atgggtcgtg gacagatcct gtgttcttct atgtccaggc caaaacagga tatgaaaact    3840
tcatccatct gatcatcgct ctgcccgtcg ctgtcctgtt gatcgtggga gggttggtga    3900
ttatgctgta cgtcttccat agaaagagaa ataacagcag gctggggaat ggagtgctgt    3960
atgcctctgt gaacccggag tacttcagcg ctgctgatgt gtacgttcct gatgagtggg    4020
```

```
aggtggctcg ggagaagatc accatgagcc gggaacttgg gcaggggtcg tttgggatgg   4080
tctatgaagg agttgccaag ggtgtggtga aagatgaacc tgaaaccaga gtggccatta   4140
aaacagtgaa cgaggccgca agcatgcgtg agaggattga gtttctcaac gaagcttctg   4200
tgatgaagga gttcaattgt caccatgtgg tgcgattgct gggtgtggtg tcccaaggcc   4260
agccaacact ggtcatcatg gaactgatga cacggggcga tctcaaaagt tatctccggt   4320
ctctgaggcc agaaatggag aataatccag tcctagcacc tccaagcctg agcaagatga   4380
ttcagatggc cggagagatt gcagacggca tggcatacct caacgccaat aagttcgtcc   4440
acagagacct tgctgcccgg aattgcatgg tagccgaaga tttcacagtc aaaatcggag   4500
attttggtat gacgcgagat atctatgaga cagactatta ccggaaagga gggaagggc   4560
tgctgcccgt gcgctggatg tctcctgagt ccctcaagga tggagtcttc accacttact   4620
cggacgtctg gtccttcggg gtcgtcctct gggagatcgc cacactggcc gagcagccct   4680
accagggctt gtccaacgag caagtccttc gcttcgtcat ggagggcggc cttctggaca   4740
agccagacaa ctgtcctgac atgctgtttg aactgatgcg catgtgctgg cagtataacc   4800
ccaagatgag gccttccttc ctggagatca tcagcagcat caaagaggag atggagcctg   4860
gcttccggga ggtctccttc tactacagcg aggagaacaa gctgcccgag ccggaggagc   4920
tggacctgga gccagagaac atggagagcg tcccctgga cccctcggcc tcctcgtcct   4980
ccctgccact gcccgacaga cactcaggac acaaggccga gaacggcccc ggccctgggg   5040
tgctggtcct ccgcgccagc ttcgacgaga gacagcctta cgcccacatg aacgggggcc   5100
gcaagaacga gcgggccttg ccgctgcccc agtcttcgac ctgctgatcc ttggatcctg   5160
aatctgtgca acagtaacg tgtgcgcacg cgcagcgggg tggggggga gagagagttt   5220
taacaatcca ttcacaagcc tcctgtacct cagtggatct tcagaactgc ccttgctgcc   5280
cgcgggagac agcttctctg cagtaaaaca catttgggat gttcctttt tcaatatgca   5340
agcagctttt tattccctgc ccaaacccttaactgacatg ggcctttaag aaccttaatg   5400
acaacactta atagcaacag agcacttgag aaccagtctc ctcactctgt ccctgtcctt   5460
ccctgttctc cctttctctc tcctctctgc ttcataacgg aaaaataatt gccacaagtc   5520
cagctgggaa gccctttta tcagtttgag gaagtggctg tccctgtggc cccatccaac   5580
cactgtacac acccgcctga caccgtgggt cattacaaaa aaacacgtgg agatggaaat   5640
tttacctttt atctttcacc tttctaggga catgaaattt acaaagggcc atcgttcatc   5700
caaggctgtt accatttaa cgctgcctaa ttttgccaaa atcctgaact ttctccctca   5760
tcggcccggc gctgattcct cgtgtccgga ggcatgggtg agcatggcag ctggttgctc   5820
catttgagag acacgctggc gacacactcc gtccatccga ctgcccctgc tgtgctgctc   5880
aaggccacag gcacacaggt ctcattgctt ctgactagat tattatttgg gggaactgga   5940
cacaataggt ctttctctca gtgaaggtgg ggagaagctg aaccggcttc cctgccctgc   6000
ctccccagcc ccctgcccaa cccccaagaa tctggtggcc atgggccccg aagcagcctg   6060
gcggacaggc ttggagtcaa ggggcccat gcctgcttct ctcccagccc cagctccccc   6120
gcccgccccc aaggacacag atgggaaggg gtttccaggg actcagcccc actgttgatg   6180
caggtttgca aggaaagaaa ttcaaacacc acaacagcag taagaagaaa agcagtcaat   6240
ggattcaagc attctaagct tgttgacat tttctctgtt cctaggactt cttcatgggt   6300
cttacagttc tatgttagac catgaaacat ttgcatacac atcgtcttta atgtcacttt   6360
```

```
tataacttttt ttacggttca gatattcatc tatacgtctg tacagaaaaa aaaaagctgc    6420 tattttttt gttcttgatc tttgtggatt taatctatga aaaccttcag gtccaccctc      6480 tccccttttct gctcactcca agaaacttct tatgctttgt actagagtgc gtgactttct   6540
tcctcttttc ccggtaatgg atacttctat cacataattt gccatgaact gttggatgcc    6600 ttttttataaa tacatccccc atccctgctc ccacctgccc ctttagttgt tttctaaccc   6660
gtaggctctc tgggcacgag gcagaaagca ggccgggcac ccatcctgag agggccgcgc    6720
tcctctcccc agcctgccct cacagcattg gagcctgtta cagtgcaaga catgatacaa    6780
actcaggtca gaaaaacaaa ggttaaatat ttcacacgtc tttgttcagt gttttccactc   6840 accgtggttg agaagcctca ccctctcttt cccttgcctt tgcttaggtt gtgacacaca    6900
tatatatata ttttttttaat tcttgggtac aacagcagtg ttaaccgcag acactaggca   6960
tttggattac tattttttctt aatggctatt taatccttcc atcccacgaa aaacagctgc   7020
tgagtccaag ggagcagcag agcgtggtcc ggcagggcct gttgtggccc tcgccacccc    7080
cctcaccgga ccgactgacc tgtctttgga accagaacat cccaagggaa ctccttcgca    7140
ctggcgttga gtgggacccc gggatccagg ctggcccagg gcggcaccct cagggctgtg    7200
cccgctggag tgctaggtgg aggcagcaca gacgccacgg tgcccaaga gccccttgc     7260 ttcttgctgg gggaccaggg ctgtggtgct ggcccacttt ccctcggcca ggaatccagg    7320
tccttggggc ccagggtcct tgtcttgttt cattttagc acttctcacc agagagatga    7380
cagcacaaga gttgcttctg ggatagaaat gtttaggagt aagaacaaag ctgggatacg   7440
gtgattgcta gttgtgactg aagattcaac acagaaaaga aagtttatac ggcttttttg    7500
ctggtcagca gtttgtccca ctgctttctc tagtctctat cccatagcgt gttcccttta    7560
aaaaaaaaaa aaaggtatta tatgtaggag ttttctttta atttattttg tgataaatta    7620
ccagtttcaa tcactgtaga aaagccccat tatgaattta aatttcaagg aaagggtgtg   7680
tgtgtgtgta tgtgtgggt gtgtgtgtgt gagagtgatg ggacagttct tgattttttg    7740 ggttttttt cccccaaaca tttatctacc tcactcttat tttttatatg tgtatataga   7800
caaaagaata catctcacct ttctcagcac ctgacaatag gccgttgata ctggtaacct    7860
catccacgcc acaggcgcca cacccaggtg atgcaggggg aagccaggct gtattccggg   7920
gtcaaagcaa cactaactca cctctctgct catttcagac agcttgcctt tttctgagat    7980
gtcctgtttt gtgttgcttt ttttgttttg ttttctatct tggtttccac caaggtgtta    8040
gatttctcct cctcctagcc aggtggccct gtgaggccaa cgagggcacc agagcacacc   8100
tgggggagcc accaggctgt ccctggctgg ttgtctttgg aacaaactgc ttctgtgcag   8160
atggaatgac caaacacattt cgtccttaag agagcagtgg ttcctcaggt tctgaggaga   8220
ggaaggtgtc caggcagcac catctctgtg cgaatcccca gggtaaaggc gtgggcatt    8280 gggtttgctc cccttgctgc tgctccatcc ctgcaggagg ctcgcgctga ggcaggaccg    8340
tgcggccatg gctgctgcat tcattgagca caaaggtgca gctgcagcag cagctggaga   8400
gcaagagtca cccagcctgt gcgccagaat gcagaggctc ctgacctcac agccagtccc    8460
tgatagaaca cacgcaggag cagagtcccc tcccctccca ggctgccctc tcaacttctc    8520
cctcacctcc ttccctaggg gtagacagag atgtaccaaa ccttccggct ggaaagccca    8580
gtggccggcg ccgaggctcg tggcgtcacg cccccccgc cagggctgta cctccgtctc    8640
cctggtcctg ctgctcacag gacagacggc tcgctcccct cttccagcag ctgctcttac    8700
aggcactgat gatttcgctg ggaagtgtgg cgggcagctt tgcctaagcg tggatggctc    8760
```

```
ctcggcaatt ccagcctaag tgaaggcgct caggagcctc ctgctggaac gcgacccatc    8820
tctcccagga ccccggggat cttaaggtca ttgagaaata ctgttggatc agggttttgt    8880
tcttccacac tgtaggtgac cccttggaat aacggcctct cctctcgtgc acatacctac    8940
cggtttccac aactggattt ctacagatca ttcagctggt tataagggtt ttgtttaaac    9000
tgtccgagtt actgatgtca ttttgttttt gttttatgta ggtagctttt aagtagaaaa    9060
cactaacagt gtagtgccca tcatagcaaa tgcttcagaa acacctcaat aaaagagaaa    9120
acttggcttg tgtgatggtg cagtcacttt actggaccaa cccacccacc ttgactatac    9180
caaggcatca tctatccaca gttctagcct aacttcatgc tgatttctct gcctcttgat    9240
ttttctctgt gtgttccaaa taatcttaag ctgagttgtg cattttcca tgcaacctcc     9300 ttctgccagc agctcacact gcttgaagtc atatgaacca ctgaggcaca tcatggaatt    9360
gatgtgagca ttaagacgtt ctcccacaca gcccttccct gaggcagcag gagctggtgt    9420
gtactggaga cactgttgaa cttgatcaag acccagacca ccccaggtct ccttcgtggg    9480
atgtcatgac gtttgacata ccttttggaac gagcctcctc cttggaagat ggaagaccgt    9540
gttcgtggcc gacctggcct ctcctggcct gtttcttaag atgcggagtc acatttcaat    9600
ggtacgaaaa gtggcttcgt aaaatagaag agcagtcact gtggaactac caaatggcga    9660
gatgctcggt gcacattggg gtgctttggg ataaaagatt tatgagccaa ctattctctg    9720
gcaccagatt ctaggccagt tgttccact gaagcttttc ccacagcagt ccacctctgc     9780
aggctggcag ccgaatggct tgccagtggc tctgtggcaa gatcacactg agatcgatgg    9840
gtgagaaggc taggatgctt gtctagtgtt cttagctgtc acgttggctc cttccagggt    9900
ggccagacgg tgttggccac tcccttctaa aacacaggcg ccctcctggt gacagtgacc    9960
cgccgtggta tgccttggcc cattccagca gtcccagtta tgcatttcaa gtttggggtt   10020
tgttcttttc gttaatgttc ctctgtgttg tcagctgtct tcatttcctg ggctaagcag   10080
cattgggaga tgtggaccag agatccactc cttaagaacc agtggcgaaa gacactttct   10140
ttcttcactc tgaagtagct ggtggtacaa atgagaactt caagagagga tgttatttag   10200
actgaacctc tgttgccaga gatgctgaag atacagacct tggacaggtc agagggtttc   10260 attttttggcc ttcatcttag atgactggtt gcgtcatttg gagaagtgag tgctccttga   10320
tggtggaatg accgggtggt gggtacagaa ccattgtcac agggatcctg gcacagaaa    10380 gagttacgag cagcagggtg cagggcttgg aaggaatgtg ggcaaggttt tgaacttgat   10440
tgttcttgaa gctatcagac cacatcgagg ctcagcagtc atccgtgggc atttggtttc   10500
aacaaagaaa cctaacatcc tactctggaa actgatctcg gagttaaggc gaattgttca   10560
agaacacaaa ctacatcgca ctcgtcagtt gtcagttctg gggcatgact ttagcgtttt   10620
gtttctgcga gaacataacg atcactcatt tttatgtccc acgtgtgtgt gtccgcatct   10680
ttctggtcaa cattgtttta actagtcact cattagcgtt tcaatagggg ctcttaagtc   10740
cagtagatta cgggtagtca gttgacgaag atctggttta caagaactaa ttaaatgttt   10800
cattgcattt ttgtaagaac agaataattt tataaaatgt ttgtagttta taattgccga   10860
aaataattta aagacacttt ttttttctct gtgtgtgcaa atgtgtgttt gtgatccatt   10920 ttttttttt tttttagga cacctgttta ctagctagct ttacaatatg ccaaaaaagg    10980
atttctccct gaccccatcc gtggttcacc ctcttttccc cccatgcttt ttgccctagt   11040
ttataacaaa ggaatgatga tgatttaaaa agtagttctg tatcttcagt atcttggtct   11100
```

| | |
|---|---:|
| tccagaaccc tctggttggg aaggggatca ttttttactg gtcatttccc tttggagtgt | 11160 |
| agctacttta acagatggaa agaacctcat tggccatgga aacagccgag gtgttggagc | 11220 |
| ccagcagtgc atggcaccgt tcggcatctg gcttgattgg tctggctgcc gtcattgtca | 11280 |
| gcacagtgcc atggacatgg gaagacttga ctgcacagcc aatggttttc atgatgatta | 11340 |
| cagcatacac agtgatcaca taaacgatga cagctatggg gcacacaggc catttgctta | 11400 |
| catgcctcgt atcatgactg attactgctt tgttagaaca cagaagagac cctattttat | 11460 |
| ttaaggcaga accccgaaga tacgtatttc caatacagaa aagaattttt aataaaaact | 11520 |
| ataacataca caaaaattgg ttttaaagtt gactccactt cctctaactc cagtggattg | 11580 |
| ttggccatgt ctccccaact ccacaatatc tctatcatgg gaaacacctg gggttttttgc | 11640 |
| gctacatagg agaagatct ggaaactatt tgggttttgt tttcaacttt tcatttggat | 11700 |
| gtttggcgtt gcacacacac atccaccggt ggaagagacg cccggtgaaa acacctgtct | 11760 |
| gctttctaag ccagtgaggt tgaggtgaga ggtttgccag agtttgtcta cctctgggta | 11820 |
| tcccttttgtc tgggataaaa aaaatcaaac cagaaggcgg gatggaatgg atgcaccgca | 11880 |
| aataatgcat tttctgagtt ttcttgttaa aaaaaaattt ttttaagtaa gaaaaaaaaa | 11940 |
| ggtaataaca tggccaattt gttacataaa atgactttct gtgtataaat tattcctaaa | 12000 |
| aaatcctgtt tatataaaaa atcagtagat gaaaaaaatt tcaaaatgtt tttgtatatt | 12060 |
| ctgttgtaag aatttattcc tgttattgcg atatactctg gattctttac ataatggaaa | 12120 |
| aaagaaactg tctattttga atggctgaag ctaaggcaac gttagtttct cttactctgc | 12180 |
| ttttttctag taaagtacta catggtttaa gttaaataaa ataattctgt atgcaaaaaa | 12240 |
| aaaaaaaaaa aaaaaaaaaa aa | 12262 |

```
<210> SEQ ID NO 6
<211> LENGTH: 12259
<212> TYPE: DNA
<213> ORGANISM: Homo Sapien

<400> SEQUENCE: 6
```

| | |
|---|---:|
| agtgtgtggc agcggcggcg gcggcgcggc gaggctgggg ctcttgttta ccagcattaa | 60 |
| ctccgctgag cggaaaaaaa aagggaaaaa acccgaggag gagcgagcgc accaggcgaa | 120 |
| ctcgagagag gcgggagagc gagagggacg ccgccagcga gcctgcccac ggccggcgct | 180 |
| cgcagaccct cggccccgct ccccggatcc ccccgcgccc tccacgcccc tcccgcgcgg | 240 |
| gggcagctcc acgcgcgcc tcgcctcggc tgtgaccttc agcgagccgg agccccgcg | 300 |
| cagagcaggc ggcggcgggc gggggccggg cggggccgg cgcggggcgg gcggcggcgc | 360 |
| agagccgggc ggcgcggcgg gagtgctgag cgcggcgcgg ccggcccgcc gctttgtgtg | 420 |
| tgtcctggat ttgggaagga gctcgccgcg gcggcggcgg cgctgaggga ggaggcggcg | 480 |
| gcgagcggag ccaggaggag gaggaggagg gggagccgct cattcatttt gactccgcgt | 540 |
| ttctgcccct cgccggcctc gcctgtgacc cggacttcgg ggcgatcttg cgaactgcgt | 600 |
| cgcgccctcc cgcggcggaa gctcgggcgt ccggccgcct cccgcgcggc cagggccggg | 660 |
| cttgtttttc ctcgcctagg cagatttggg cttttgccccc tttctttgca gttttccccc | 720 |
| cttcctgcct ctccgggttt gaaaatggag gccgacgacg ccgacagccc gccccggcgc | 780 |
| gcctcgggtt cccgactccg ccgagccctg ggccgctgct gccggcgctg aggggccgcc | 840 |
| ccgcgccgcc cgccccgtcc gcgcacccgg agggccccgg cggcgccgcc ttcggagtat | 900 |
| tgtttccttc gcccttgttt ttggaggggg agcgaagact gagtttgaga cttgtttcct | 960 |

```
ttcatttcct tttttctttt tcttttcttt tttttttttt tttttttttt tgagaaaggg    1020
gaatttcatc ccaaataaaa ggaatgaagt ctggctccgg aggagggtcc ccgacctcgc    1080
tgtgggggct cctgtttctc tccgccgcgc tctcgctctg gccgacgagt ggagaaatct    1140
gcgggccagg catcgacatc cgcaacgact atcagcagct gaagcgcctg gagaactgca    1200
cggtgatcga gggctacctc cacatcctgc tcatctccaa ggccgaggac taccgcagct    1260
accgcttccc caagctcacg gtcattaccg agtacttgct gctgttccga gtggctggcc    1320
tcgagagcct cggagacctc ttccccaacc tcacggtcat ccgcggctgg aaactcttct    1380
acaactacgc cctggtcatc ttcgagatga ccaatctcaa ggatattggg ctttacaacc    1440
tgaggaacat tactcggggg gccatcagga ttgagaaaaa tgctgacctc tgttacctct    1500
ccactgtgga ctggtccctg atcctggatg cggtgtccaa taactacatt gtggggaata    1560
agcccccaaa ggaatgtggg gacctgtgtc caggaccat ggaggagaag ccgatgtgtg    1620
agaagaccac catcaacaat gagtacaact accgctgctg gaccacaaac cgctgccaga    1680
aaatgtgccc aagcacgtgt gggaagcggg cgtgcaccga gaacaatgag tgctgccacc    1740
ccgagtgcct gggcagctgc agcgcgcctg acaacgacac ggcctgtgta gcttgccgcc    1800
actactacta tgccggtgtc tgtgtgcctg cctgcccgcc caacacctac aggtttgagg    1860
gctggcgctg tgtggaccgt gacttctgcg ccaacatcct cagcgccgag agcagcgact    1920
ccgaggggtt tgtgatccac gacggcgagt gcatgcagga gtgcccctcg ggcttcatcc    1980
gcaacggcag ccagagcatg tactgcatcc cttgtgaagg tccttgcccg aaggtctgtg    2040
aggaagaaaa gaaaacaaag accattgatt ctgttacttc tgctcagatg ctccaaggat    2100
gcaccatctt caagggcaat tgctctcatta acatccgacg ggggaataac attgcttcag    2160
agctggagaa cttcatgggg ctcatcgagg tggtgacggg ctacgtgaag atccgccatt    2220
ctcatgcctt ggtctccttg tccttcctaa aaaaccttcg cctcatccta ggagaggagc    2280
agctagaagg gaattactcc ttctacgtcc tcgacaacca gaacttgcag caactgtggg    2340
actgggacca ccgcaacctg accatcaaag cagggaaaat gtactttgct ttcaatccca    2400
aattatgtgt ttccgaaatt taccgcatgg aggaagtgac ggggactaaa gggcgccaaa    2460
gcaaagggga cataaacacc aggaacaacg gggagagagc ctcctgtgaa agtgacgtcc    2520
tgcatttcac ctccaccacc acgtcgaaga atcgcatcat cataacctgg caccggtacc    2580
ggccccctga ctacagggat ctcatcagct tcaccgtttta ctacaaggaa gcacccttta    2640
agaatgtcac agagtatgat gggcaggatg cctgcggctc caacagctgg aacatggtgg    2700
acgtggacct cccgcccaac aaggacgtgg agcccggcat cttactacat gggctgaagc    2760
cctggactca gtacgccgtt tacgtcaagg ctgtgacct caccatggtg gagaacgacc    2820
atatccgtgg ggccaagagt gagatcttgt acattcgcac caatgcttca gttccttcca    2880
ttcccttgga cgttctttca gcatcgaact cctcttctca gttaatcgtg aagtggaacc    2940 ctcccttct gcccaacggc aacctgagtt actacattgt gcgctggcag cggcagcctc    3000
aggacggcta ccttttaccgg cacaattact gctccaaaga caaatcccc atcaggaagt    3060 atgccgacgg caccatcgac attgaggagg tcacagaaa ccccaagact gaggtgtgtg    3120
gtggggagaa agggccttgc tgcgcctgcc ccaaaactga agccgagaag caggccgaga    3180 aggaggagc tgaataccgc aaagtctttg agaatttcct gcacaactcc atcttcgtgc    3240
ccagacctga aaggaagcgg agagatgtca tgcaagtggc caacaccacc atgtccagcc    3300
```

```
gaagcaggaa caccacggcc gcagacacct acaacatcac cgacccggaa gagctggaga    3360
cagagtaccc tttctttgag agcagagtgg ataacaagga gagaactgtc atttctaacc    3420
ttcggccttt cacattgtac cgcatcgata tccacagctg caaccacgag gctgagaagc    3480
tgggctgcag cgcctccaac ttcgtctttg caaggactat gcccgcagaa ggagcagatg    3540
acattcctgg gccagtgacc tgggagccaa ggcctgaaaa ctccatcttt ttaaagtggc    3600
cggaacctga gaatcccaat ggattgattc taatgtatga aataaaatac ggatcacaag    3660
ttgaggatca gcgagaatgt gtgtccagac aggaatacag gaagtatgga ggggccaagc    3720
taaaccggct aaacccgggg aactacacag cccggattca ggccacatct ctctctggga    3780
atgggtcgtg gacagatcct gtgttcttct atgtccaggc caaaagatat gaaaacttca    3840
tccatctgat catcgctctg cccgtcgctg tcctgttgat cgtgggaggg ttggtgatta    3900
tgctgtacgt cttccataga aagagaaata acagcaggct ggggaatgga gtgctgtatg    3960
cctctgtgaa cccggagtac ttcagcgctg ctgatgtgta cgttcctgat gagtgggagg    4020
tggctcggga gaagatcacc atgagccggg aacttgggca ggggtcgttt gggatggtct    4080
atgaaggagt tgccaagggt gtggtgaaag atgaacctga aaccagagtg gccattaaaa    4140
cagtgaacga ggccgcaagc atgcgtgaga ggattgagtt tctcaacgaa gcttctgtga    4200
tgaaggagtt caattgtcac catgtggtgc gattgctggg tgtggtgtcc caaggccagc    4260
caacactggt catcatggaa ctgatgacac ggggcgatct caaaagttat ctccggtctc    4320
tgaggccaga aatggagaat aatccagtcc tagcacctcc aagcctgagc aagatgattc    4380
agatggccgg agagattgca gacggcatgg catacctcaa cgccaataag ttcgtccaca    4440
gagaccttgc tgcccggaat tgcatggtag ccgaagattt cacagtcaaa atcggagatt    4500
ttggtatgac gcgagatatc tatgagacag actattaccg gaaaggaggg aaagggctgc    4560
tgcccgtgcg ctggatgtct cctgagtccc tcaaggatgg agtcttcacc acttactcgg    4620
acgtctggtc cttcggggtc gtcctctggg agatcgccac actggccgag cagcccctacc    4680 agggcttgtc caacgagcaa gtccttcgct tcgtcatgga gggcggcctt ctggacaagc    4740
cagacaactg tcctgacatg ctgtttgaac tgatgcgcat gtgctggcag tataacccca    4800 agatgagggcc ttccttcctg gagatcatca gcagcatcaa agaggagatg gagcctggct    4860 tccggggaggt ctccttctac tacagcgagg agaacaagct gcccgagccg gaggagctgg    4920
acctggagcc agagaacatg gagagcgtcc cctggaccc ctcggcctcc tcgtcctccc    4980
tgccactgcc cgacagacac tcaggacaca aggccgagaa cggccccggc cctggggtgc    5040
tggtcctccg cgccagcttc gacgagagac agccttacgc ccacatgaac gggggccgca    5100
agaacgagcg ggccttgccg ctgccccagt cttcgacctg ctgatccttg gatcctgaat    5160
ctgtgcaaac agtaacgtgt gcgcacgcgc agcggggtgg ggggggagag agagttttaa    5220
caatccattc acaagcctcc tgtacctcag tggatcttca gaactgccct tgctgcccgc    5280
gggagacagc ttctctgcag taaaacacat ttgggatgtt cctttttca atatgcaagc    5340 agcttttat tccctgccca aacccttaac tgacatgggc ctttaagaac cttaatgaca    5400
acacttaata gcaacagagc acttgagaac cagtctcctc actctgtccc tgtccttccc    5460
tgttctccct ttctctctcc tctctgcttc ataacggaaa aataattgcc acaagtccag    5520
ctgggaagcc cttttatca gtttgaggaa gtggctgtcc ctgtggcccc atccaaccac    5580
tgtacacacc cgcctgacac cgtgggtcat tacaaaaaaa cacgtggaga tggaaatttt    5640 taccttatc tttcaccttt ctagggacat gaaatttaca aagggccatc gttcatccaa    5700
```

-continued

```
ggctgttacc attttaacgc tgcctaattt tgccaaaatc ctgaactttc tccctcatcg    5760
gcccggcgct gattcctcgt gtccggaggc atgggtgagc atggcagctg ttgctccat    5820 ttgagagaca cgctggcgac acactccgtc catccgactg ccctgctgt gctgctcaag     5880 gccacaggca cacaggtctc attgcttctg actagattat tatttggggg aactggacac    5940
aataggtctt tctctcagtg aaggtgggga gaagctgaac cggcttccct gccctgcctc    6000
cccagccccc tgcccaaccc ccaagaatct ggtggccatg ggccccgaag cagcctggcg    6060
gacaggcttg gagtcaaggg gccccatgcc tgcttctctc ccagcccag ctcccccgcc     6120 cgccccaag acacagatg ggaagggtt tccaggact cagccccact gttgatgcag        6180
gtttgcaagg aaagaaattc aaacaccaca acagcagtaa aagaaaagc agtcaatgga     6240 ttcaagcatt ctaagctttg ttgacatttt ctctgttcct aggacttctt catgggtctt    6300
acagttctat gttagaccat gaaacatttg catacacatc gtctttaatg tcactttat    6360 aactttttta cggttcagat attcatctat acgtctgtac agaaaaaaaa aagctgctat    6420
tttttttgtt cttgatcttt gtggatttaa tctatgaaaa ccttcaggtc caccctctcc    6480
cctttctgct cactccaaga aacttcttat gctttgtact agagtgcgtg actttcttcc    6540
tcttttcccg gtaatggata cttctatcac ataatttgcc atgaactgtt ggatgccttt    6600
ttataaatac atcccccatc cctgctccca cctgcccctt tagttgtttt ctaacccgta    6660
ggctctctgg gcacgaggca gaaagcaggc cgggcaccca tcctgagagg gccgcgctcc    6720 tctcccagc ctgccctcac agcattggag cctgttacag tgcaagacat gatacaaact     6780
caggtcagaa aaacaaaggt taaatatttc acacgtcttt gttcagtgtt tccactcacc    6840
gtggttgaga agcctcaccc tctctttccc ttgcctttgc ttaggttgtg acacacatat    6900
atatatattt ttttaattct tgggtacaac agcagtgtta accgcagaca ctaggcattt    6960
ggattactat ttttcttaat ggctatttaa tccttccatc ccacgaaaaa cagctgctga    7020
gtccaaggga gcagcagagc gtggtccggc agggcctgtt gtggccctcg ccacccccct    7080
caccggaccg actgacctgt ctttggaacc agaacatccc aagggaactc cttcgcactg    7140
gcgttgagtg ggaccccggg atccaggctg cccagggcg gcaccctcag ggctgtgccc     7200
gctggagtgc taggtggagg cagcacagac gccacggtgg cccaagagcc cctttgcttc    7260
ttgctggggg accagggctg tggtgctggc ccactttccc tcggccagga atccaggtcc    7320
ttggggccca ggggtcttgt cttgtttcat ttttagcact tctcaccaga gagatgacag    7380
cacaagagtt gcttctggga tagaaatgtt taggagtaag aacaaagctg ggatacggtg    7440
attgctagtt gtgactgaag attcaacaca gaaagaaag tttatacggc ttttttgctg     7500
gtcagcagtt tgtcccactg ctttctctag tctctatccc atagcgtgtt ccctttaaaa    7560
aaaaaaaaaa ggtattatat gtaggagttt tcttttaatt tattttgtga taaattacca    7620
gtttcaatca ctgtagaaaa gccccattat gaatttaaat ttcaaggaaa gggtgtgtgt    7680
gtgtgtatgt gtggggtgtg tgtgtgtgag agtgatggga cagttcttga ttttttgggt    7740
tttttttccc ccaaacattt atctacctca ctcttatttt ttatatgtgt atatagacaa    7800
aagaatacat ctcacctttc tcagcacctg acaataggcc gttgatactg gtaacctcat    7860
ccacgccaca ggcgccacac ccaggtgatg caggggaag ccaggctgta ttccggggtc     7920
aaagcaacac taactcacct ctctgctcat ttcagacagc ttgcctttt ctgagatgtc     7980 ctgttttgtg ttgcttttttt tgtttgtttt tctatcttgg tttccaccaa ggtgttagat    8040
```

```
ttctcctcct cctagccagg tggccctgtg aggccaacga gggcaccaga gcacacctgg    8100
gggagccacc aggctgtccc tggctggttg tctttggaac aaactgcttc tgtgcagatg    8160
gaatgaccaa cacatttcgt ccttaagaga gcagtggttc ctcaggttct gaggagagga    8220
aggtgtccag gcagcaccat ctctgtgcga atccccaggg taaaggcgtg gggcattggg    8280
tttgctcccc ttgctgctgc tccatccctg caggaggctc gcgctgaggc aggaccgtgc    8340
ggccatggct gctgcattca ttgagcacaa aggtgcagct gcagcagcag ctggagagca    8400
agagtcaccc agcctgtgcg ccagaatgca gaggctcctg acctcacagc cagtccctga    8460
tagaacacac gcaggagcag agtcccctcc ccctccaggc tgccctctca acttctccct    8520
cacctccttc cctaggggta gacagagatg taccaaacct tccggctgga aagcccagtg    8580
gccggcgccg aggctcgtgg cgtcacgccc ccccgccag gctgtacct ccgtctccct    8640 ggtcctgctg ctcacaggac agacggctcg ctcccctctt ccagcagctg ctcttacagg    8700
cactgatgat ttcgctggga agtgtggcgg gcagctttgc ctaagcgtgg atggctcctc    8760
ggcaattcca gcctaagtga aggcgctcag gagcctcctg ctggaacgcg acccatctct    8820
cccaggaccc cggggatctt aaggtcattg agaaatactg ttggatcagg gttttgttct    8880
tccacactgt aggtgacccc ttggaataac ggcctctcct ctcgtgcaca tacctaccgg    8940
tttccacaac tggatttcta cagatcattc agctggttat aagggttttg tttaaactgt    9000
ccgagttact gatgtcattt tgttttttgtt ttatgtaggt agcttttaag tagaaaacac    9060
taacagtgta gtgcccatca tagcaaatgc ttcagaaaca cctcaataaa agagaaaact    9120
tggcttgtgt gatggtgcag tcactttact ggaccaaccc acccaccttg actataccaa    9180
ggcatcatct atccacagtt ctagcctaac ttcatgctga tttctctgcc tcttgatttt    9240
tctctgtgtg ttccaaataa tcttaagctg agttgtggca ttttccatgc aacctccttc    9300
tgccagcagc tcacactgct tgaagtcata tgaaccactg aggcacatca tggaattgat    9360
gtgagcatta agacgttctc ccacacagcc cttccctgag gcagcaggag ctggtgtgta    9420
ctggagacac tgttgaactt gatcaagacc cagaccaccc caggtctcct tcgtgggatg    9480
tcatgacgtt tgacatacct ttggaacgag cctcctcctt ggaagatgga agaccgtgtt    9540
cgtggccgac ctggcctctc ctggcctgtt tcttaagatg cggagtcaca tttcaatggt    9600
acgaaaagtg gcttcgtaaa atagaagagc agtcactgtg gaactaccaa atggcgagat    9660
gctcggtgca cattggggtg ctttgggata aaagatttat gagccaacta ttctctggca    9720
ccagattcta ggccagtttg ttccactgaa gcttttccca cagcagtcca cctctgcagg    9780
ctggcagccg aatggcttgc cagtggctct gtggcaagat cacactgaga tcgatgggtg    9840
agaaggctag gatgcttgtc tagtgttctt agctgtcacg ttggctcctt ccagggtggc    9900
cagacggtgt tggccactcc cttctaaaac acaggcgccc tcctggtgac agtgacccgc    9960
cgtggtatgc cttggcccat tccagcagtc ccagttatgc atttcaagtt tggggtttgt    10020
tcttttcgtt aatgttcctc tgtgttgtca gctgtcttca tttcctgggc taagcagcat    10080
tgggagatgt ggaccagaga tccactcctt aagaaccagt ggcgaaagac actttctttc    10140
ttcactctga agtagctggt ggtacaaatg agaacttcaa gagaggatgt tatttagact    10200
gaacctctgt tgccagagat gctgaagata cagaccttgg acaggtcaga gggtttcatt    10260
tttggccttc atcttagatg actggttgcg tcatttggag aagtgagtgc tccttgatgg    10320
tggaatgacc gggtggtggg tacagaacca ttgtcacagg gatcctggca cagagaagag    10380
ttacgagcag cagggtgcag ggcttggaag gaatgtgggc aaggttttga acttgattgt    10440
```

```
tcttgaagct atcagaccac atcgaggctc agcagtcatc cgtgggcatt tggtttcaac    10500
aaagaaacct aacatcctac tctggaaact gatctcggag ttaaggcgaa ttgttcaaga    10560
acacaaacta catcgcactc gtcagttgtc agttctgggg catgacttta gcgttttgtt    10620
tctgcgagaa cataacgatc actcattttt atgtcccacg tgtgtgtgtc cgcatctttc    10680
tggtcaacat tgttttaact agtcactcat tagcgttttc aatagggctc ttaagtccag    10740
tagattacgg gtagtcagtt gacgaagatc tggtttacaa gaactaatta aatgtttcat    10800 tgcattttg taagaacaga ataatttat aaaatgtttg tagtttataa ttgccgaaaa    10860
taatttaaag acactttttt tttctctgtg tgtgcaaatg tgtgtttgtg atccattttt    10920
tttttttttt tttaggacac ctgtttacta gctagcttta caatatgcca aaaaaggatt    10980
tctccctgac cccatccgtg gttcaccctc ttttcccccc atgcttttg ccctagttta    11040 taacaaagga atgatgatga tttaaaaagt agttctgtat cttcagtatc ttggtcttcc    11100
agaaccctct ggttgggaag gggatcattt tttactggtc atttcccttt ggagtgtagc    11160
tactttaaca gatggaaaga acctcattgg ccatggaaac agccgaggtg ttggagccca    11220
gcagtgcatg gcaccgttcg gcatctggct tgattggtct ggctgccgtc attgtcagca    11280
cagtgccatg gacatgggaa gacttgactg cacagccaat ggttttcatg atgattacag    11340
catacacagt gatcacataa acgatgacag ctatggggca cacaggccat ttgcttacat    11400
gcctcgtatc atgactgatt actgctttgt tagaacacag aagagaccct attttattta    11460
aggcagaacc ccgaagatac gtatttccaa tacagaaaag aattttaat aaaaactata    11520 acatacacaa aaattggttt taagttgac tccacttcct ctaactccag tggattgttg    11580
gccatgtctc cccaactcca caatatctct atcatgggaa acacctgggg ttttgcgct    11640 acataggaga aagatctgga aactatttgg gttttgtttt caacttttca tttggatgtt    11700
tggcgttgca cacacacatc caccggtgga agagacgccc ggtgaaaaca cctgtctgct    11760
ttctaagcca gtgaggttga ggtgagaggt ttgccagagt ttgtctacct ctgggtatcc    11820
ctttgtctgg gataaaaaaa atcaaaccag aaggcgggat ggaatggatg caccgcaaat    11880
aatgcatttt ctgagttttc ttgttaaaaa aaaatttttt taagtaagaa aaaaaaggt    11940 aataacatgg ccaatttgtt acataaaatg actttctgtg tataaattat tcctaaaaaa    12000
tcctgtttat ataaaaaatc agtagatgaa aaaaatttca aaatgttttt gtatattctg    12060
ttgtaagaat ttattcctgt tattgcgata tactctggat tctttacata atggaaaaaa    12120
gaaactgtct atttttgaatg gctgaagcta aggcaacgtt agtttctctt actctgcttt    12180
tttctagtaa agtactacat ggtttaagtt aaataaaata attctgtatg caaaaaaaaa    12240
aaaaaaaaaa aaaaaaaa                                                 12259

<210> SEQ ID NO 7
<211> LENGTH: 1367
<212> TYPE: PRT
<213> ORGANISM: Homo Sapien

<400> SEQUENCE: 7

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45
```

```
Leu Glu Asn Cys Thr Val Ile Glu Gly Tyr Leu His Ile Leu Leu Ile
 50                  55                  60

Ser Lys Ala Glu Asp Tyr Arg Ser Tyr Arg Phe Pro Lys Leu Thr Val
 65                  70                  75                  80

Ile Thr Glu Tyr Leu Leu Leu Phe Arg Val Ala Gly Leu Glu Ser Leu
                 85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Lys Pro Met Cys
            180                 185                 190

Glu Lys Thr Thr Ile Asn Asn Glu Tyr Asn Tyr Arg Cys Trp Thr Thr
    195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460
```

```
Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
                500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
            805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
            850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
```

```
              885                 890                 895
Asn Pro Gly Asn Tyr Thr Ala Arg Ile Gln Ala Thr Ser Leu Ser Gly
            900                 905                 910
Asn Gly Ser Trp Thr Asp Pro Val Phe Phe Tyr Val Gln Ala Lys Thr
            915                 920                 925
Gly Tyr Glu Asn Phe Ile His Leu Ile Ile Ala Leu Pro Val Ala Val
            930                 935                 940
Leu Leu Ile Val Gly Gly Leu Val Ile Met Leu Tyr Val Phe His Arg
945                 950                 955                 960
Lys Arg Asn Asn Ser Arg Leu Gly Asn Gly Val Leu Tyr Ala Ser Val
                965                 970                 975
Asn Pro Glu Tyr Phe Ser Ala Ala Asp Val Tyr Val Pro Asp Glu Trp
            980                 985                 990
Glu Val Ala Arg Glu Lys Ile Thr Met Ser Arg Glu Leu Gly Gln Gly
                995                1000                1005
Ser Phe Gly Met Val Tyr Glu Gly Val Ala Lys Gly Val Val Lys
            1010                1015                1020
Asp Glu Pro Glu Thr Arg Val Ala Ile Lys Thr Val Asn Glu Ala
            1025                1030                1035
Ala Ser Met Arg Glu Arg Ile Glu Phe Leu Asn Glu Ala Ser Val
            1040                1045                1050
Met Lys Glu Phe Asn Cys His His Val Val Arg Leu Leu Gly Val
            1055                1060                1065
Val Ser Gln Gly Gln Pro Thr Leu Val Ile Met Glu Leu Met Thr
            1070                1075                1080
Arg Gly Asp Leu Lys Ser Tyr Leu Arg Ser Leu Arg Pro Glu Met
            1085                1090                1095
Glu Asn Asn Pro Val Leu Ala Pro Pro Ser Leu Ser Lys Met Ile
            1100                1105                1110
Gln Met Ala Gly Glu Ile Ala Asp Gly Met Ala Tyr Leu Asn Ala
            1115                1120                1125
Asn Lys Phe Val His Arg Asp Leu Ala Ala Arg Asn Cys Met Val
            1130                1135                1140
Ala Glu Asp Phe Thr Val Lys Ile Gly Asp Phe Gly Met Thr Arg
            1145                1150                1155
Asp Ile Tyr Glu Thr Asp Tyr Tyr Arg Lys Gly Gly Lys Gly Leu
            1160                1165                1170
Leu Pro Val Arg Trp Met Ser Pro Glu Ser Leu Lys Asp Gly Val
            1175                1180                1185
Phe Thr Thr Tyr Ser Asp Val Trp Ser Phe Gly Val Val Leu Trp
            1190                1195                1200
Glu Ile Ala Thr Leu Ala Glu Gln Pro Tyr Gln Gly Leu Ser Asn
            1205                1210                1215
Glu Gln Val Leu Arg Phe Val Met Glu Gly Gly Leu Leu Asp Lys
            1220                1225                1230
Pro Asp Asn Cys Pro Asp Met Leu Phe Glu Leu Met Arg Met Cys
            1235                1240                1245
Trp Gln Tyr Asn Pro Lys Met Arg Pro Ser Phe Leu Glu Ile Ile
            1250                1255                1260
Ser Ser Ile Lys Glu Glu Met Glu Pro Gly Phe Arg Glu Val Ser
            1265                1270                1275
Phe Tyr Tyr Ser Glu Glu Asn Lys Leu Pro Glu Pro Glu Glu Leu
            1280                1285                1290
```

```
Asp Leu Glu Pro Glu Asn Met Glu Ser Val Pro Leu Asp Pro Ser
    1295                1300                1305

Ala Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365
```

<210> SEQ ID NO 8
<211> LENGTH: 1366
<212> TYPE: PRT
<213> ORGANISM: Homo Sapien

<400> SEQUENCE: 8

```
Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
```

```
            290                 295                 300
Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
    530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
    610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
    690                 695                 700

Thr Glu Ala Glu Lys Gln Ala Glu Lys Glu Glu Ala Glu Tyr Arg Lys
705                 710                 715                 720
```

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
        850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Arg
        915                 920                 925

Tyr Glu Asn Phe Ile His Leu Ile Ile Ala Leu Pro Val Ala Val Leu
930                 935                 940

Leu Ile Val Gly Gly Leu Val Ile Met Leu Tyr Val Phe His Arg Lys
945                 950                 955                 960

Arg Asn Asn Ser Arg Leu Gly Asn Gly Val Leu Tyr Ala Ser Val Asn
                965                 970                 975

Pro Glu Tyr Phe Ser Ala Ala Asp Val Tyr Val Pro Asp Glu Trp Glu
            980                 985                 990

Val Ala Arg Glu Lys Ile Thr Met Ser Arg Glu Leu Gly Gln Gly Ser
        995                 1000                1005

Phe Gly Met Val Tyr Glu Gly Val Ala Lys Gly Val Val Lys Asp
    1010                1015                1020

Glu Pro Glu Thr Arg Val Ala Ile Lys Thr Val Asn Glu Ala Ala
    1025                1030                1035

Ser Met Arg Glu Arg Ile Glu Phe Leu Asn Glu Ala Ser Val Met
    1040                1045                1050

Lys Glu Phe Asn Cys His His Val Val Arg Leu Leu Gly Val Val
    1055                1060                1065

Ser Gln Gly Gln Pro Thr Leu Val Ile Met Glu Leu Met Thr Arg
    1070                1075                1080

Gly Asp Leu Lys Ser Tyr Leu Arg Ser Leu Arg Pro Glu Met Glu
    1085                1090                1095

Asn Asn Pro Val Leu Ala Pro Pro Ser Leu Ser Lys Met Ile Gln
    1100                1105                1110

Met Ala Gly Glu Ile Ala Asp Gly Met Ala Tyr Leu Asn Ala Asn
    1115                1120                1125

```
Lys  Phe  Val  His  Arg  Asp  Leu  Ala  Ala  Arg  Asn  Cys  Met  Val  Ala
     1130                1135                1140

Glu  Asp  Phe  Thr  Val  Lys  Ile  Gly  Asp  Phe  Gly  Met  Thr  Arg  Asp
     1145                1150                1155

Ile  Tyr  Glu  Thr  Asp  Tyr  Tyr  Arg  Lys  Gly  Gly  Lys  Gly  Leu  Leu
     1160                1165                1170

Pro  Val  Arg  Trp  Met  Ser  Pro  Glu  Ser  Leu  Lys  Asp  Gly  Val  Phe
     1175                1180                1185

Thr  Thr  Tyr  Ser  Asp  Val  Trp  Ser  Phe  Gly  Val  Val  Leu  Trp  Glu
     1190                1195                1200

Ile  Ala  Thr  Leu  Ala  Glu  Gln  Pro  Tyr  Gln  Gly  Leu  Ser  Asn  Glu
     1205                1210                1215

Gln  Val  Leu  Arg  Phe  Val  Met  Glu  Gly  Gly  Leu  Leu  Asp  Lys  Pro
     1220                1225                1230

Asp  Asn  Cys  Pro  Asp  Met  Leu  Phe  Glu  Leu  Met  Arg  Met  Cys  Trp
     1235                1240                1245

Gln  Tyr  Asn  Pro  Lys  Met  Arg  Pro  Ser  Phe  Leu  Glu  Ile  Ile  Ser
     1250                1255                1260

Ser  Ile  Lys  Glu  Glu  Met  Glu  Pro  Gly  Phe  Arg  Glu  Val  Ser  Phe
     1265                1270                1275

Tyr  Tyr  Ser  Glu  Glu  Asn  Lys  Leu  Pro  Glu  Pro  Glu  Glu  Leu  Asp
     1280                1285                1290

Leu  Glu  Pro  Glu  Asn  Met  Glu  Ser  Val  Pro  Leu  Asp  Pro  Ser  Ala
     1295                1300                1305

Ser  Ser  Ser  Ser  Leu  Pro  Leu  Pro  Asp  Arg  His  Ser  Gly  His  Lys
     1310                1315                1320

Ala  Glu  Asn  Gly  Pro  Gly  Pro  Gly  Val  Leu  Val  Leu  Arg  Ala  Ser
     1325                1330                1335

Phe  Asp  Glu  Arg  Gln  Pro  Tyr  Ala  His  Met  Asn  Gly  Gly  Arg  Lys
     1340                1345                1350

Asn  Glu  Arg  Ala  Leu  Pro  Leu  Pro  Gln  Ser  Ser  Thr  Cys
     1355                1360                1365

<210> SEQ ID NO 9
<211> LENGTH: 21
<212> TYPE: RNA
<213> ORGANISM: Artificial Sequence
<220> FEATURE:
<223> OTHER INFORMATION: siRNA 1 sense strand
<220> FEATURE:
<221> NAME/KEY: misc_feature
<222> LOCATION: (20)..(21)
<223> OTHER INFORMATION: n is DNA T

<400> SEQUENCE: 9
ugguaucucc ucuaaguaan n                                              21

<210> SEQ ID NO 10
<211> LENGTH: 21
<212> TYPE: RNA
<213> ORGANISM: Artificial Sequence
<220> FEATURE:
<223> OTHER INFORMATION: siRNA 2 sense strand
<220> FEATURE:
<221> NAME/KEY: misc_feature
<222> LOCATION: (20)..(21)
<223> OTHER INFORMATION: n is DNA T

<400> SEQUENCE: 10
cgagcaaggu ccuuccauan n                                              21
```

<210> SEQ ID NO 11
<211> LENGTH: 21
<212> TYPE: RNA
<213> ORGANISM: Artificial Sequence
<220> FEATURE:
<223> OTHER INFORMATION: siRNA 1 antisense strand
<220> FEATURE:
<221> NAME/KEY: misc_feature
<222> LOCATION: (20)..(20)
<223> OTHER INFORMATION: n is DNA G
<220> FEATURE:
<221> NAME/KEY: misc_feature
<222> LOCATION: (21)..(21)
<223> OTHER INFORMATION: n is DNA C

<400> SEQUENCE: 11
uuacuuagag gagauaccan n                                           21

<210> SEQ ID NO 12
<211> LENGTH: 21
<212> TYPE: RNA
<213> ORGANISM: Artificial Sequence
<220> FEATURE:
<223> OTHER INFORMATION: siRNA 2 antisense strand
<220> FEATURE:
<221> NAME/KEY: misc_feature
<222> LOCATION: (20)..(20)
<223> OTHER INFORMATION: n is DNA C
<220> FEATURE:
<221> NAME/KEY: misc_feature
<222> LOCATION: (21)..(21)
<223> OTHER INFORMATION: n is DNA A

<400> SEQUENCE: 12
uauggaagga ccuugcucgn n                                           21

<210> SEQ ID NO 13
<211> LENGTH: 18
<212> TYPE: DNA
<213> ORGANISM: Artificial Sequence
<220> FEATURE:
<223> OTHER INFORMATION: Human IGFBP7: Primer Pair 1

<400> SEQUENCE: 13
actggctggg tgctggta                                               18

<210> SEQ ID NO 14
<211> LENGTH: 19
<212> TYPE: DNA
<213> ORGANISM: Artificial Sequence
<220> FEATURE:
<223> OTHER INFORMATION: Human IGFBP7: Primer Pair 1

<400> SEQUENCE: 14
tggatgcatg gcactcata                                              19

<210> SEQ ID NO 15
<211> LENGTH: 20
<212> TYPE: DNA
<213> ORGANISM: Artificial Sequence
<220> FEATURE:
<223> OTHER INFORMATION: Human IGFBP7: Primer Pair 2

<400> SEQUENCE: 15
gaatcccgac acctgtcctc                                             20

<210> SEQ ID NO 16

```
<211> LENGTH: 20
<212> TYPE: DNA
<213> ORGANISM: Artificial Sequence
<220> FEATURE:
<223> OTHER INFORMATION: Human IGFBP7: Primer Pair 2

<400> SEQUENCE: 16
cagcacccag ccagttactt                                               20

<210> SEQ ID NO 17
<211> LENGTH: 21
<212> TYPE: DNA
<213> ORGANISM: Artificial Sequence
<220> FEATURE:
<223> OTHER INFORMATION: Human HPRT1: Primer Pair

<400> SEQUENCE: 17
tgacactggc aaaacaatgc a                                             21

<210> SEQ ID NO 18
<211> LENGTH: 21
<212> TYPE: DNA
<213> ORGANISM: Artificial Sequence
<220> FEATURE:
<223> OTHER INFORMATION: Human HPRT1: Primer Pair

<400> SEQUENCE: 18
ggtccttttc accagcaagc t                                             21

<210> SEQ ID NO 19
<211> LENGTH: 20
<212> TYPE: DNA
<213> ORGANISM: Artificial Sequence
<220> FEATURE:
<223> OTHER INFORMATION: Human NPPB: Primer Pair

<400> SEQUENCE: 19
caccgcaaaa tggtcctcta                                               20

<210> SEQ ID NO 20
<211> LENGTH: 20
<212> TYPE: DNA
<213> ORGANISM: Artificial Sequence
<220> FEATURE:
<223> OTHER INFORMATION: Human NPPB: Primer Pair

<400> SEQUENCE: 20
gtccatcttc ctcccaaagc                                               20

<210> SEQ ID NO 21
<211> LENGTH: 20
<212> TYPE: DNA
<213> ORGANISM: Artificial Sequence
<220> FEATURE:
<223> OTHER INFORMATION: Human Tp53: Primer Pair

<400> SEQUENCE: 21
cagcacatga cggaggttgt                                               20

<210> SEQ ID NO 22
<211> LENGTH: 21
<212> TYPE: DNA
<213> ORGANISM: Artificial Sequence
<220> FEATURE:
<223> OTHER INFORMATION: Human Tp53: Primer Pair

<400> SEQUENCE: 22
```
tcatccaaat actccacacg c                                          21

<210> SEQ ID NO 23
<211> LENGTH: 19
<212> TYPE: DNA
<213> ORGANISM: Artificial Sequence
<220> FEATURE:
<223> OTHER INFORMATION: Human p21: Primer Pair

<400> SEQUENCE: 23
tgtccgtcag aacccatgc                                             19

<210> SEQ ID NO 24
<211> LENGTH: 21
<212> TYPE: DNA
<213> ORGANISM: Artificial Sequence
<220> FEATURE:
<223> OTHER INFORMATION: Human p21: Primer Pair

<400> SEQUENCE: 24
aaagtcgaag ttccatcgct c                                          21

<210> SEQ ID NO 25
<211> LENGTH: 20
<212> TYPE: DNA
<213> ORGANISM: Artificial Sequence
<220> FEATURE:
<223> OTHER INFORMATION: Mouse Nppa: Primer Pair

<400> SEQUENCE: 25
gcttccaggc catattggag                                            20

<210> SEQ ID NO 26
<211> LENGTH: 19
<212> TYPE: DNA
<213> ORGANISM: Artificial Sequence
<220> FEATURE:
<223> OTHER INFORMATION: Mouse Nppa: Primer Pair

<400> SEQUENCE: 26
gggggcatga cctcatctt                                             19

<210> SEQ ID NO 27
<211> LENGTH: 21
<212> TYPE: DNA
<213> ORGANISM: Artificial Sequence
<220> FEATURE:
<223> OTHER INFORMATION: Mouse Nppb: Primer Pair

<400> SEQUENCE: 27
gaggtcactc ctatcctctg g                                          21

<210> SEQ ID NO 28
<211> LENGTH: 22
<212> TYPE: DNA
<213> ORGANISM: Artificial Sequence
<220> FEATURE:
<223> OTHER INFORMATION: Mouse Nppb: Primer Pair

<400> SEQUENCE: 28
gccatttcct ccgactttc tc                                          22

<210> SEQ ID NO 29
<211> LENGTH: 22
<212> TYPE: DNA

```
<213> ORGANISM: Artificial Sequence
<220> FEATURE:
<223> OTHER INFORMATION: Mouse Trp53: Primer Pair

<400> SEQUENCE: 29
cacgtactct cctcccctca at                                              22

<210> SEQ ID NO 30
<211> LENGTH: 20
<212> TYPE: DNA
<213> ORGANISM: Artificial Sequence
<220> FEATURE:
<223> OTHER INFORMATION: Mouse Trp53: Primer Pair

<400> SEQUENCE: 30
aactgcacag ggcacgtctt                                                 20

<210> SEQ ID NO 31
<211> LENGTH: 22
<212> TYPE: DNA
<213> ORGANISM: Artificial Sequence
<220> FEATURE:
<223> OTHER INFORMATION: Mouse Myh6: Primer Pair

<400> SEQUENCE: 31
tgcactacgg aaacatgaag tt                                              22

<210> SEQ ID NO 32
<211> LENGTH: 23
<212> TYPE: DNA
<213> ORGANISM: Artificial Sequence
<220> FEATURE:
<223> OTHER INFORMATION: Mouse Myh6: Primer Pair

<400> SEQUENCE: 32
cgatggaata gtacacttgc tgt                                             23

<210> SEQ ID NO 33
<211> LENGTH: 23
<212> TYPE: DNA
<213> ORGANISM: Artificial Sequence
<220> FEATURE:
<223> OTHER INFORMATION: Mouse Myh7: Primer Pair

<400> SEQUENCE: 33
actgtcaaca cttaagaggg tca                                             23

<210> SEQ ID NO 34
<211> LENGTH: 23
<212> TYPE: DNA
<213> ORGANISM: Artificial Sequence
<220> FEATURE:
<223> OTHER INFORMATION: Mouse Myh7: Primer Pair

<400> SEQUENCE: 34
ttggatgatt tgatcttcca ggg                                             23

<210> SEQ ID NO 35
<211> LENGTH: 20
<212> TYPE: DNA
<213> ORGANISM: Artificial Sequence
<220> FEATURE:
<223> OTHER INFORMATION: Mouse Hprt1: Primer Pair

<400> SEQUENCE: 35
gctgacctgc tggattacat                                                 20
```

<210> SEQ ID NO 36
<211> LENGTH: 20
<212> TYPE: DNA
<213> ORGANISM: Artificial Sequence
<220> FEATURE:
<223> OTHER INFORMATION: Mouse Hprt1: Primer Pair

<400> SEQUENCE: 36
ttggggctgt actgcttaac                                                 20

<210> SEQ ID NO 37
<211> LENGTH: 846
<212> TYPE: DNA
<213> ORGANISM: Artificial Sequence
<220> FEATURE:
<223> OTHER INFORMATION: hIGFBP7-CDS Plasmid

<400> SEQUENCE: 37
atggaacggc ctagcctgag agccctgctg ctgggagctg ctggacttct ccttctgctg      60
ctgcccctga gcagctccag ctcctctgat acctgtggcc cttgcgagcc tgccagctgt     120
cctcctctgc ctccactggg atgtctgctg ggcgagacaa gagatgcctg cggctgctgt     180
cccatgtgcg ctagaggcga gggcgaacct tgtggcggag gcggagctgg cagaggctat     240 tgtgccctg gcatggaatg cgtgaagtcc cggaagcgga gaaagggcaa agccggcgct     300
gctgcaggcg gacctggcgt gtcaggcgtg tgtgtgtgca agagcagata ccccgtgtgc     360
ggctccgacg gcaccacata tccaagcggc tgtcagctga gggccgcctc tcagagagcc     420
gagagcagag gcgagaaggc catcacccag gtgtccaagg gcacatgcga gcagggccct     480
agcatcgtga cccccccaa ggacatctgg aacgtgacag gcgcccaggt gtacctgagc     540
tgcgaagtga tcggcatccc caccccgtg ctgatctgga caaagtgaa gcggggccac     600 tacggcgtgc agagaacaga actgctgccc ggcgacagag acaacctggc catccagaca     660
agaggcggac ccgagaagca cgaagtgacc ggatgggtgc tggtgtcccc cctgtccaaa     720
gaggatgccg cgagtacga gtgccacgcc agcaattctc agggccaggc cagcgccagt     780
gccaagatca cagtggtgga tgccctgcac gagatccccg tgaagaaagg cgaaggcgcc     840
gagctg                                                              846

<210> SEQ ID NO 38
<211> LENGTH: 870
<212> TYPE: DNA
<213> ORGANISM: Artificial Sequence
<220> FEATURE:
<223> OTHER INFORMATION: hIGFBP7-CDS-6xHis Plasmid

<400> SEQUENCE: 38
atggaacggc ctagcctgag agccctgctg ctgggagctg ctggacttct ccttctgctg      60
ctgcccctga gcagctccag ctcctctgat acctgtggcc cttgcgagcc tgccagctgt     120
cctcctctgc ctccactggg atgtctgctg ggcgagacaa gagatgcctg cggctgctgt     180
cccatgtgcg ctagaggcga gggcgaacct tgtggcggag gcggagctgg cagaggctat     240 tgtgccctg gcatggaatg cgtgaagtcc cggaagcgga gaaagggcaa agccggcgct     300
gctgcaggcg gacctggcgt gtcaggcgtg tgtgtgtgca agagcagata ccccgtgtgc     360
ggctccgacg gcaccacata tccaagcggc tgtcagctga gggccgcctc tcagagagcc     420
gagagcagag gcgagaaggc catcacccag gtgtccaagg gcacatgcga gcagggccct     480

```
agcatcgtga cccccccaa ggacatctgg aacgtgacag gcgcccaggt gtacctgagc      540
tgcgaagtga tcggcatccc caccccgtg ctgatctgga acaaagtgaa gcggggccac      600
tacggcgtgc agagaacaga actgctgccc ggcgacagag acaacctggc catccagaca    660
agaggcggac ccgagaagca cgaagtgacc ggatgggtgc tggtgtcccc cctgtccaaa    720
gaggatgccg gcgagtacga gtgccacgcc agcaattctc agggccaggc cagcgccagt    780
gccaagatca cagtggtgga tgccctgcac gagatccccg tgaagaaagg cgaaggcgcc    840
gagctgcatc accatcacca tcacgtttaa                                     870

<210> SEQ ID NO 39
<211> LENGTH: 58
<212> TYPE: DNA
<213> ORGANISM: Artificial Sequence
<220> FEATURE:
<223> OTHER INFORMATION: shRNA targeting IGFBP7

<400> SEQUENCE: 39
ccgggctggt atctcctcta agtaactcga gttacttaga ggagatacca gcttttg       58

<210> SEQ ID NO 40
<211> LENGTH: 21
<212> TYPE: DNA
<213> ORGANISM: Artificial Sequence
<220> FEATURE:
<223> OTHER INFORMATION: shRNA targeting sequence

<400> SEQUENCE: 40
gctggtatct cctctaagta a                                              21

<210> SEQ ID NO 41
<211> LENGTH: 6
<212> TYPE: DNA
<213> ORGANISM: Artificial Sequence
<220> FEATURE:
<223> OTHER INFORMATION: shRNA hairpin loop sequence

<400> SEQUENCE: 41 ctcgag                                                                6

<210> SEQ ID NO 42
<211> LENGTH: 5
<212> TYPE: DNA
<213> ORGANISM: Artificial Sequence
<220> FEATURE:
<223> OTHER INFORMATION: sequence terminating the shRNA expression for
      U6 promoter

<400> SEQUENCE: 42 ttttt                                                                 5
```

THERAPEUTICS TARGETING IGFBP7 FOR THE TREATMENT OR PREVENTION OF HEART FAILURE AND METABOLIC DISEASES

CROSS REFERENCE TO RELATED APPLICATION

This application claims priority to U.S. provisional patent application No. 62/418,038, filed Nov. 4, 2016, which is incorporated herein by reference in its entirety.

FIELD OF INVENTION

The present invention relates generally to treatment or prevention of heart failure, metabolic diseases, and related conditions. More specifically, the present invention relates to treatment methods and uses of insulin-like growth factor-binding protein 7 (IGFBP7) inhibitors for the treatment or prevention of heart failure and IGFBP7-related metabolic diseases.

SEQUENCE LISTING

The present application is being filed along with a Sequence Listing in electronic format. The Sequence Listing is provided as a file titled "935599US1_ST25," created Nov. 3, 2017, last modified Nov. 3, 2017, and is 72,000 bytes in size. The information in the electronic format of the Sequence Listing is incorporated herein by reference in its entirety.

BACKGROUND

The World Health Organization (WHO) identifies heart disease as a leading cause of death globally. Heart failure (HF) is a major global public health concern despite tremendous effort and resources aimed at its diagnosis and treatment. Pressure overload-induced cardiac hypertrophy and heart failure are both conditions contributing to cardiovascular disease morbidity and mortality. Hypertrophy is an important risk factor in heart disease, and myocardial infarction (i.e. heart attack) involves damage to the heart muscle and may lead to heart failure or cardiac arrest resulting in death. HF is associated with significant morbidity and mortality and accounts for a substantial number of hospitalizations, a large percentage of healthcare resource utilization, and increased cost.

A new challenge in heart failure is its changing epidemiology—in that heart failure with reduced ejection fraction (HFrEF) is decreasing; while heart failure with preserved ejection fraction (HFpEF) is increasing (Bhatia, Liu, NEJM 2006). HFpEF is associated with risk factors of hypertension, diabetes and elderly age. The phenotype of the HEpEF heart typically includes myocyte hypertrophy, increased diastolic stiffness, matricellular fibrosis, innate immunity activation and cell death and loss. To date there is no evidence based effective treatment for HFpEF. The actual pathophysiology of HFpEF, and strategies for treatment have been elusive.

The biochemical pathways underlying cardiovascular disease are an active area of ongoing study. Much research has been focused on identifying markers for evaluating cardiovascular disease risk in a subject (see, for example, US patent application publication no. 2011/0059089), and on identifying therapeutic targets and gene silencing agents for treatment of cardiovascular disease (see, for example, US patent application publication no. 2010/0035963). Despite these efforts, heart disease remains a major health concern worldwide.

According to the National Center for Biotechnology Information (NCBI), Insulin-like growth factor-binding protein 7 (IGFBP7) is a protein involved in the regulation of insulin-like growth factors (IGFs) and modulation of IGF receptor binding. IGFBP7 is a known binder of insulin-like growth factor 1 (IGF-I) and 2 (IGF-II). IGFBP7 has been implicated in a variety of diseases, including certain forms of cancer and in metabolic syndrome (Liu et al., 2015, Serum IGFBP7 levels associate with insulin resistance and the risk of metabolic syndrome in a Chinese population, *Sci. Rep.*, 5:10227).

Alternative, additional, and/or improved treatments for heart disease and/or metabolic diseases is desirable.

SUMMARY OF INVENTION

Insulin-like growth factor-binding protein 7 (IGFBP7) has been identified herein as a therapeutic target for the treatment or prevention of heart diseases, metabolic diseases, and other related diseases or conditions. IGFBP7 inhibitors having IGFBP7 expression and/or activity reducing properties are described herein. Treatment methods, and uses, relating to such IGFBP7 inhibitors for the treatment or prevention of heart failure, IGFBP7-related metabolic diseases, and related diseases or conditions are provided.

In an embodiment, there is provided herein a method for the treatment or prevention of heart failure in a subject in need thereof, said method comprising:

administering an insulin-like growth factor-binding protein 7 (IGFBP7) inhibitor to said subject to reduce IGFBP7 expression and/or activity levels in the heart of said subject, thereby treating or preventing heart failure in said subject.

In another embodiment of the above method, the heart failure may be pressure overload induced heart failure.

In still another embodiment of the method or methods above, the method may prevent or attenuate pressure overload induced cardiac fibrosis, fibrosis remodeling, or both, in said subject.

In yet another embodiment of the method or methods above, the method may prevent or reduce stress-induced cellular senescence in said subject.

In another embodiment of the method or methods above, the method may prevent or reduce cardiac hypertrophy, hypertrophic remodeling, or both, in said subject.

In another embodiment of the method or methods above, the heart failure may comprise heart failure with preserved ejection fraction (HFpEF).

In yet another embodiment of the method or methods above, the IGFBP7 inhibitor may comprise a gene silencing nucleic acid targeting an IGFBP7 gene or an IGFBP7 mRNA in said subject. In particular embodiments, the IGFBP7 inhibitor may comprise an IGFBP7-targeting siRNA such as siRNA 1 (SEQ ID NOs: 9 and 11), siRNA 2 (SEQ ID NOs: 10 and 12), or a combination thereof.

In still another embodiment of the method or methods above, the IGFBP7 inhibitor may comprise an anti-IGFBP7 antibody.

In yet another embodiment of the method or methods above, the method may additionally comprise a step of: administering an insulin-like growth factor 1 receptor (IGF-1R) inhibitor to said subject to inhibit IGF-1R expression and/or activity levels in the heart of said subject.

In still another embodiment of the method above, the IGF-1R inhibitor may comprise a gene silencing nucleic acid targeting an IGF-1R gene or an IGF-1R mRNA in said subject, or an anti-IGF-1R antibody. In a particular embodiment, the IGF-1R inhibitor may comprise picropodophyllin (ppp).

In an embodiment, there is provided herein a use of an insulin-like growth factor-binding protein 7 (IGFBP7) inhibitor for the treatment or prevention of heart failure in a subject in need thereof, wherein said IGFBP7 inhibitor is for administration to said subject to reduce IGFBP7 expression and/or activity levels in the heart of said subject.

In another embodiment of the use above, the heart failure may be pressure overload induced heart failure.

In still another embodiment of the use or uses above, the IGFBP7 inhibitor may be for preventing or attenuating pressure overload induced cardiac fibrosis, fibrosis remodeling, or both, in said subject.

In yet another embodiment of the use or uses above, the IGFBP7 inhibitor may be for preventing or reducing stress-induced cellular senescence in said subject.

In another embodiment of the use or uses above, the IGFBP7 inhibitor may be for preventing or reducing cardiac hypertrophy, hypertrophic remodeling, or both, in said subject.

In another embodiment of the use or uses above, the heart failure may comprise heart failure with preserved ejection fraction (HFpEF).

In still another embodiment of the use or uses above, the IGFBP7 inhibitor may comprise a gene silencing nucleic acid targeting an IGFBP7 gene or an IGFBP7 mRNA in said subject. In particular embodiments, the IGFBP7 inhibitor may comprise an IGFBP7-targeting siRNA such as siRNA 1 (SEQ ID NOs: 9 and 11), siRNA 2 (SEQ ID NOs: 10 and 12), or a combination thereof.

In another embodiment of the use or uses above, the IGFBP7 inhibitor may comprise an anti-IGFBP7 antibody.

In still another embodiment of the use or uses above, the IGFBP7 inhibitor may be for use in combination with an insulin-like growth factor 1 receptor (IGF-1R) inhibitor which is for administration to said subject to inhibit IGF-1R expression and/or activity levels in the heart of said subject.

In another embodiment of the above use, the IGF-1R inhibitor may comprise a gene silencing nucleic acid targeting an IGF-1R gene or an IGF-1R mRNA in said subject, or an anti-IGF-1R antibody. In a particular embodiment, the IGF-1R inhibitor may comprise picropodophyllin (ppp).

In an embodiment, there is provided herein a method for the treatment or prevention of an insulin-like growth factor-binding protein 7 (IGFBP7)-related metabolic disease in a subject in need thereof, said method comprising:
administering an IGFBP7 inhibitor to said subject to reduce IGFBP7 expression and/or activity levels in said subject, thereby treating or preventing the metabolic disease in said subject.

In another embodiment of the method above, the method may additionally comprise a step of:
administering an insulin-like growth factor 1 receptor (IGF-1R) inhibitor to said subject to inhibit IGF-1R expression and/or activity levels in said subject.

In another embodiment, there is provided herein a use of an insulin-like growth factor-binding protein 7 (IGFBP7) inhibitor for the treatment or prevention of an IGFBP7-related metabolic disease in a subject in need thereof, wherein said IGFBP7 inhibitor is for administration to said subject to reduce IGFBP7 expression and/or activity levels in said subject.

In another embodiment of the above use, the IGFBP7 inhibitor may be for use in combination with an insulin-like growth factor 1 receptor (IGF-1R) inhibitor which is for administration to said subject to inhibit IGF-1R expression and/or activity levels in said subject.

In another embodiment of the method(s)/use(s) above, the IGF-1R inhibitor may comprise a gene silencing nucleic acid targeting an IGF-1R gene or an IGF-1R mRNA in said subject, an anti-IGF-1R antibody, or picropodophyllin (ppp).

In yet another embodiment of the method(s)/use(s) above, the IGFBP7-related metabolic disease may be diabetes, a kidney disease, a liver disease, or an IGFBP7-related cardiometabolic dysregulation disease.

In still another embodiment of the method(s)/use(s) above, the IGFBP7 inhibitor may comprise a gene silencing nucleic acid targeting an IGFBP7 gene or an IGFBP7 mRNA in said subject, or an anti-IGFBP7 antibody. In particular embodiments, the IGFBP7 inhibitor may comprise an IGFBP7-targeting siRNA such as siRNA 1 (SEQ ID NOs: 9 and 11), siRNA 2 (SEQ ID NOs: 10 and 12), or a combination thereof.

In an embodiment, there is provided herein a method for identifying an IGFBP7 inhibitor, said method comprising:
screening a library of potential IGFBP7 inhibitor candidates by administering potential IGFBP7 inhibitor candidates of the library to cardiac cells and determining the effect of each potential IGFBP7 inhibitor candidate on the expression level, activity level, or both, of IGFBP7 in said cardiac cells following administration;
wherein an observed reduction in IGFBP7 expression level, activity level, or both, following potential IGFBP7 inhibitor candidate administration identifies the potential IGFBP7 inhibitor candidate as an IGFBP7 inhibitor.

In another embodiment of the above method, the cardiac cells may be cultured in vitro, or may be cardiac cells of an animal model.

In still another embodiment of the method or methods above, the cardiac cells may be human cardiac myocytes.

In yet another embodiment of the method or methods above, the effect of each potential IGFBP7 inhibitor candidate on the expression level, activity level, or both, of IGFBP7 in said cardiac cells may be determined by RT-PCR, immunoblotting, or immunostaining.

In still another embodiment of the method or methods above, the effect of each potential IGFBP7 inhibitor candidate on the expression level, activity level, or both, of IGFBP7 in said cardiac cells may be determined by assessing protection from pressure induced overload heart failure, attenuation of pressure overload induced cardiac fibrosis in TAC, stress-induced cellular senescence levels, IGF-1/insulin receptor-dependent signaling levels, cardiac hypertrophy levels in TAC hearts, hypertrophic and cellular senescence signaling levels, or depression of IGF-1/Insulin induced AKT activation.

In an embodiment, there is provided herein a method for identifying a therapeutic for the treatment or prevention of heart failure or an insulin-like growth factor-binding protein 7 (IGFBP7)-related metabolic disease, said method comprising:
screening a library of potential therapeutic candidates by administering potential therapeutic candidates of the library to cardiac cells and determining the effect of each potential therapeutic candidate on the expression level, activity level, or both, of IGFBP7 in said cardiac cells following administration;
wherein an observed reduction in IGFBP7 expression level, activity level, or both, following potential therapeutic candidate administration identifies the potential therapeutic candidate as a therapeutic for the treatment or prevention of heart failure or an IGFBP7-related metabolic disease.

In another embodiment of the method above, the cardiac cells may be cultured in vitro, or may be cardiac cells of an animal model.

In still another embodiment of the method or methods above, the cardiac cells may be human cardiac myocytes.

In yet another embodiment of the method or methods above, the effect of each potential therapeutic candidate on the expression level, activity level, or both, of IGFBP7 in said cardiac cells may be determined by RT-PCR, immunoblotting, or immunostaining.

In still another embodiment of the method or methods above, the effect of each potential therapeutic candidate on the expression level, activity level, or both, of IGFBP7 in said cardiac cells may be determined by assessing protection from pressure induced overload heart failure, attenuation of pressure overload induced cardiac fibrosis in TAC, stress-induced cellular senescence levels, IGF-1/insulin receptor-dependent signaling levels, cardiac hypertrophy levels in TAC hearts, hypertrophic and cellular senescence signaling levels, or depression of IGF-1/Insulin induced AKT activation.

In an embodiment, there is provided herein a use of IGFBP7 for identifying an IGFBP7 inhibitor, where the IGFBP7 is for use in a screening assay in which the effect of potential IGFBP7 inhibitor candidates on an expression level, activity level, or both, of the IGFBP7 in cardiac cells is determined.

In another embodiment, there is provided herein a use of IGFBP7 for identifying a therapeutic for the treatment or prevention of heart failure or an insulin-like growth factor-binding protein 7 (IGFBP7)-related metabolic disease, where the IGFBP7 is for use in a screening assay in which the effect of potential therapeutic candidates on an expression level, activity level, or both, of the IGFBP7 in cardiac cells is determined.

In another embodiment, there is provided herein a method for treating a heart disease or insulin-like growth factor-binding protein 7 (IGFBP7)-related metabolic disease in a subject in need thereof, said method comprising:
   treating the subject with a heart disease or IGFBP7-related metabolic disease therapeutic,
   monitoring IGFBP7 expression levels, activity levels, or both, in a companion diagnostic assay to evaluate efficacy of the therapeutic in the subject; and
   optionally, adjusting therapeutic treatment of the subject to improve results of the companion diagnostic assay when subsequently repeated.

In another embodiment, there is provided herein a use of IGFBP7 in a companion diagnostic assay for monitoring treatment of heart disease or insulin-like growth factor-binding protein 7 (IGFBP7)-related metabolic disease in a subject in need thereof.

In yet another embodiment, there is provided herein a method of preventing or reducing stress-induced cellular senescence in heart tissue, said method comprising:
   administering an insulin-like growth factor-binding protein 7 (IGFBP7) inhibitor to said heart tissue to reduce IGFBP7 expression and/or activity levels in the heart tissue;
thereby preventing or reducing stress-induced cellular senescence in the heart tissue.

In another embodiment of the above method, the heart tissue may comprise human cardiac myocytes.

In yet another embodiment, there is provided herein a method of preventing or reducing hypertrophy in heart tissue, said method comprising:
   administering an insulin-like growth factor-binding protein 7 (IGFBP7) inhibitor to said heart tissue to reduce IGFBP7 expression and/or activity levels in the heart tissue;
   thereby preventing or reducing hypertrophy in the heart tissue.

In another embodiment of the above method, the heart tissue may comprise human cardiac myocytes.

In still another embodiment, there is provided herein a method of suppressing IGF-1 receptor/insulin receptor signaling pathway in heart tissue, said method comprising:
   administering an insulin-like growth factor-binding protein 7 (IGFBP7) inhibitor to said heart tissue to reduce IGFBP7 expression and/or activity levels in the heart tissue;
   thereby suppressing IGF-1 receptor/insulin receptor signaling pathway in the heart tissue.

In another embodiment of the above method, the heart tissue may comprise human cardiac myocytes.

In still another embodiment, there is provided herein a method of reducing or preventing fibrosis in heart tissue, said method comprising:
administering an insulin-like growth factor-binding protein 7 (IGFBP7) inhibitor to said heart tissue to reduce IGFBP7 expression and/or activity levels in the heart tissue;
thereby reducing or preventing fibrosis in the heart tissue.

In another embodiment of the above method, the heart tissue may comprise human cardiac myocytes.

In yet another embodiment, there is provided herein a method of reducing or preventing loss of diastolic function, or of improving diastolic function, in heart tissue, said method comprising:
administering an insulin-like growth factor-binding protein 7 (IGFBP7) inhibitor to said heart tissue to reduce IGFBP7 expression and/or activity levels in the heart tissue;
thereby reducing or preventing loss of diastolic function, or improving diastolic function, in the heart tissue.

In another embodiment of the above method, the heart tissue may comprise human cardiac myocytes.

BRIEF DESCRIPTION OF DRAWINGS

FIGS. 1A-1L show nucleic acid (mRNA) sequences and protein sequences of IGFBP7 and IGF-1R, two example siRNA nucleic acid sequences targeting IGFBP7 mRNA, RT-qPCR primer sequences used in the Examples provided herein, nucleic acid sequences of IGFBP7 expression plasmids used in the Examples provided herein, and sequences relating to an example of an AAV virus targeting IGFBP7 via shRNA;

DETAILED DESCRIPTION

Figure 1K:
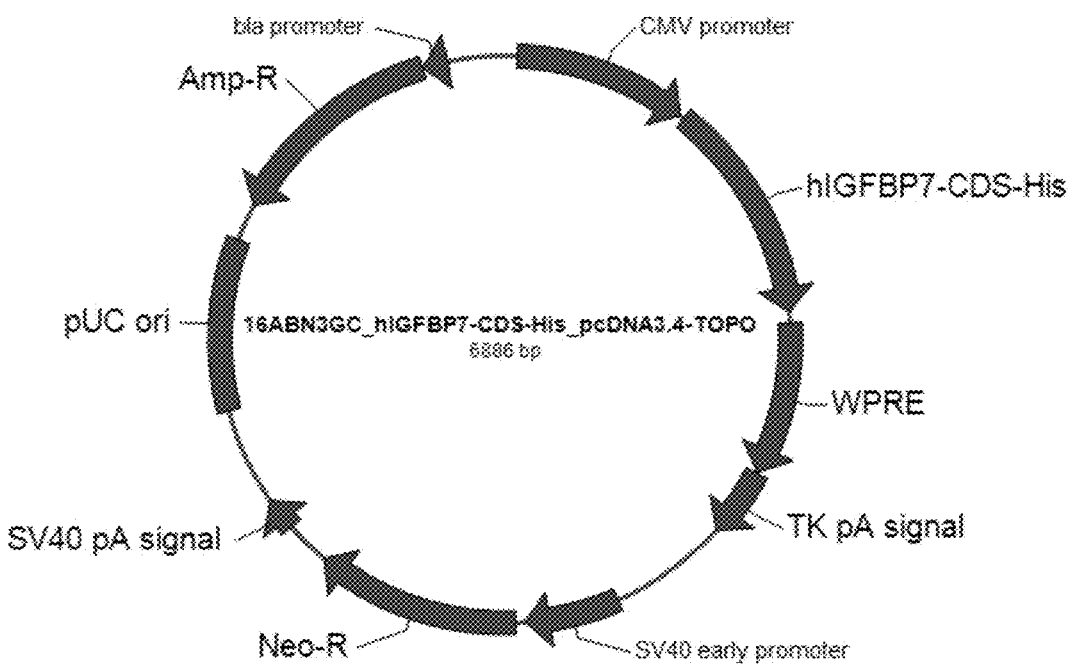

Described herein are treatment methods, and uses, relating to insulin-like growth factor-binding protein 7 (IGFBP7) inhibitors for the treatment or prevention of heart failure, IGFBP7-related metabolic diseases, and related diseases or conditions. It will be appreciated that embodiments and examples are provided for illustrative purposes intended for those skilled in the art, and are not meant to be limiting in any way.

IGFBP7 is believed to be an excellent prognostic marker for heart failure (HF), in that it correlates very reliably with diastolic function in patients with HFpEF [Gandhi P U, Liu P, Januzzi J L et al., Am J Cardiol 2014; 114:1543-9, Gandhi, 2016, Dinh, 2013]. In particular, in the I-PRESERE trial of patients with HFpEF, IGFBP7 demonstrated very a high correlation with prognosis, such that for every 70 ug/ml increase of IGFBP7, the mortality doubles during follow-up (Barroso, 2017).

While IGFBP7 is believed to be a useful biomarker for HFpEF, it was not previously known in the field whether or not IGFBP7 contributes biologically to the HFpEF process. There is very little information in the literature on IGFBP7 in the heart. IGFBP7 is located in both intracellular and secreted extracellular compartments of many cells, and is particularly abundant in the cardiovascular system, as well as in immune cells. IGFBP7, through its interaction with IGF-1, may play an important role during cardiac development. IGFBP7 is involved in embryonic stem cells committing to a cardiac lineage [Wolchinsky, 2014].

The present inventors hypothesized that IGFBP7 may be a potential regulator of pathological cardiac hypertrophy process, a hallmark of HFpEF. The structure and function of IGFBP7 share key similarities with an important group of matricellular proteins—the CCN family. CCN members play important roles in cardiac matrix modulation, including remodeling and fibrosis [Li, 2014]. The present inventors further hypothesized that IGFBP7 may have important matrix modulatory properties in concert with CTGF when expressed at high levels, which in turn contribute to cardiac fibrosis.

HFpEF typically is associated with oxidative stress, inflammation and accelerated cardiovascular aging [Tedgui, 2006; Nian, 2004]. Cardiovascular senescence has previously only been sparingly studied. Multiple stresses such as DNA damage, oxidative stress, oncogenic activation or innate immunity/inflammasome formation all contribute to cellular senescence. Intriguingly, IGFBP7 has been associated with the stress-senescence pathway in human cancer, aging or immune cells, and is a prominent member of the so called senescence associated secretory phenotype proteome (SASP) [Campisi, 2013; Kuilman, 2008]. Excessive SASP activation and inflammation leads to accelerated cellular aging, tissue degeneration and organ dysfunction, as typically found in chronic organ injury associated with aging. The present inventors hypothesized that this process is likely active in HFpHF, as it is associated with aging, oxidative stress and chronic injury such as pressure overload from hypertension or metabolic perturbation from diabetes. The inventors further hypothesized that IGFBP7 when persistently elevated may promote accelerated myocyte senescence and fibrosis, which in turn contribute to development of HFpEF. Accordingly, studies as described hereinbelow were performed to investigate whether IGFBP7 targeting may provide treatment for intervention in heart failure such as, for example, HFpEF.

As part of the studies described in detail hereinbelow, results are provided which demonstrate, in what is believed to be for the first time and without wishing to be bound by theory, that IGFBP7 regulates pathological cardiac hypertrophy, senescence and fibrosis remodeling by modulating IGF-1 signaling pathway, which in turn contributes to the progression of HFpEF. These finding identify IGFBP7 as not only an excellent prognostic marker for HFpEF, but also a target for therapeutic intervention in heart failure such as, but not limited to, HFpEF. Therapeutic targeting of IGFBP7, guided by IGFBP7 levels, may represent a new paradigm in personalized medicine for HFpEF, for example.

In an embodiment, there is provided herein a method for the treatment or prevention of heart failure in a subject in need thereof, said method comprising:

administering an insulin-like growth factor-binding protein 7 (IGFBP7) inhibitor to said subject to reduce IGFBP7 expression and/or activity levels in the heart of said subject, thereby treating or preventing heart failure in said subject.

In another embodiment, there is provided herein a use of an IGFBP7 inhibitor for the treatment or prevention of heart failure in a subject in need thereof, wherein said IGFBP7 inhibitor is for administration to said subject to reduce IGFBP7 expression and/or activity levels in the heart of said subject.

In certain embodiments, the subject may be a mammalian subject. In certain further embodiments, the subject may be human.

It will be understood that treatment or prevention of heart failure may involve treatment or prevention of a cardiovascular event. As well, treatment or prevention as referred to herein may refer to treatment or prevention of certain negative symptoms or conditions associated with or arising as a result of a cardiovascular event. By way of example, treatment or prevention may involve reducing or preventing negative changes in fractional shortening, heart weight/tibia length, lung weight/tibia length, myocyte cross sectional area, pressure overload induced cardiac fibrosis, stress induced cellular senescence, and/or cardiac hypertrophy properties, or any combination thereof, associated with or arising as a result of a cardiovascular event. Treatment may be administered in preparation for or in response to a cardiovascular event to alleviate negative effects. Prevention may involve a pro-active or prophylactic type of treatment to prevent the cardiovascular event or to reduce the onset of negative effects of a cardiovascular event.

In certain embodiments, heart failure may involve pressure overload induced heart failure, pressure overload induced cardiac fibrosis, stress-induced cellular senescence, and/or cardiac hypertrophy, or any combination thereof. Indeed, heart failure may refer to any suitable cardiovascular event or condition such as (but not limited to) a heart disease, a hypertrophy such as a pressure overload-induced cardiac hypertrophy, a cardiac fibrosis such as a pressure overload induced cardiac fibrosis, a cellular senescence such as a stress induced cellular senescence, and/or a myocardial infarction (i.e. heart attack). In certain embodiments, the heart failure may comprise heart failure with preserved ejection fraction (HFpEF).

In still another embodiment, there is provided herein a method for the treatment or prevention of an insulin-like growth factor-binding protein 7 (IGFBP7)-related metabolic disease in a subject in need thereof, said method comprising: administering an IGFBP7 inhibitor to said subject to reduce IGFBP7 expression and/or activity levels in said subject, thereby treating or preventing the metabolic disease in said subject.

In yet another embodiment, there is provided herein a use of an insulin-like growth factor-binding protein 7 (IGFBP7) inhibitor for the treatment or prevention of an IGFBP7-related metabolic disease in a subject in need thereof, wherein said IGFBP7 inhibitor is for administration to said subject to reduce IGFBP7 expression and/or activity levels in said subject.

It will be understood that treatment or prevention of an IGFBP7-related metabolic disease in a subject in need thereof may involve treatment or prevention of any suitable metabolic disease arising from or depending on IGFBP7 overexpression or upregulation. As well, treatment or prevention as referred to herein may refer to treatment or prevention of certain negative symptoms or conditions associated with or arising as a result of an IGFBP7-related metabolic disease. By way of example, treatment or prevention may involve reducing or preventing diabetes, a kidney disease, or a liver disease (such as, for example, fatty liver) associated with IGFBP7, or a cardiometabolic dysregulation associated with IGFBP7. Some examples of IGFBP7-related metabolic disease are further described in, for example: Liu et al., 2015, Serum IGFBP7 levels associate with insulin resistance and the risk of metabolic syndrome in a Chinese population, *Sci. Rep.*, 5:10227; and Watanabe J et al., 2016. Role of IGFBP7 in Diabetic Nephropathy: TGF-β1 Induces IGFBP7 via Smad2/4 in Human Renal Proximal Tubular Epithelial Cells. PLoS One. 11:e0150897 (both of which are herein incorporated by reference in their entirety). Treatment may be administered in preparation for, or in response to, a metabolic disease event to alleviate negative effects. Prevention may involve a pro-active or prophylactic type of treatment to prevent the metabolic disease or to reduce the onset of negative effects of a metabolic disease.

Insulin-like growth factor-binding protein 7 (IGFBP7) is a protein involved in the regulation of insulin-like growth factors (IGFs) and modulation of IGF receptor binding. IGFBP7 is a known binder of insulin-like growth factor 1 (IGF-I) and 2 (IGF-II). The human IGFBP7 gene nucleic acid sequence may be found on the NCBI website using the following accession number and chromosome location information: Location: 4q12 NC_000004.12 (57031071 . . . 57110385, complement). The mRNA transcribed from this gene is shown in FIG. 1A as SEQ ID NO: 1 (human IGFBP7 mRNA sequence, Accession number NM_001553.2, transcript variant 1) and SEQ ID NO: 2 (human IGFBP7 mRNA sequence, Accession number NM 001253835.1, transcript variant 2), and the amino acid sequence of human IGFBP7 protein is shown in FIG. 1B as SEQ ID NO: 3 (human IGFBP7 protein sequence, Accession number NP 001544.1, isoform 1 precursor) and SEQ ID NO: 4 (human IGFBP7 protein sequence, Accession number NP_001240764.1, isoform 2 precursor). Mouse IGFBP7 gene, mRNA, and protein sequences are similar to those of the human sequences, and can be found on the NCBI website as accession numbers NM_001159518.1 (Mus musculus insulin-like growth factor binding protein 7 (Igfbp7), transcript variant 1, mRNA), NP_001152990.1 (insulin-like growth factor-binding protein 7 isoform 1 precursor [Mus musculus]), NM_008048.3 (Mus musculus insulin-like growth factor binding protein 7 (Igfbp7), transcript variant 2, mRNA), and NP_032074.3 (insulin-like growth factor-binding protein 7 isoform 2 precursor [Mus musculus]). As identified and described in detail herein, IGFBP7 is unregulated and/or upregulated in stressed myocardium, and IGFBP7 deficiency may protect from pressure overload induced heart failure, pressure overload induced cardiac fibrosis, stress induced cellular senescence, and/or cardiac hypertrophy. IGFBP7 deficiency or down regulation may also treat or prevent certain IGFBP7-related metabolic diseases and/or conditions or symptoms associated therewith. IGFBP7 is cell-surface exposed, and represents a druggable target as described in detail herein.

As such, insulin-like growth factor-binding protein 7 (IGFBP7) inhibitors for targeting IGFBP7 and reducing IGFBP7 expression and/or activity levels have been identified. The person of skill in the art will recognize that a suitable IGFBP7 inhibitor may be any suitable inhibitor able to reduce IGFBP7 expression levels, activity levels, or both. By way of non-limiting example, a suitable IGFBP7 inhibitor may be a gene silencing nucleic acid (such as, but not limited to, an siRNA, an antisense oligonucleotide, a short-hairpin RNA, a miRNA, a dicer-substrate RNA, a DNAzyme, or an aptamer targeting the IGFBP7 gene or the IGFBP7 messenger RNA so as to reduce expression thereof, or a chemically modified derivative of such molecules), or an aptamer which binds and inhibits IGFBP7, or an anti-IGFBP7 antibody (such as a monoclonal, polyclonal, murine, chimeric, humanized, or human antibody targeting an IGFBP7 epitope so as to interfere with IGFBP7 activity), or a small molecule which can bind and inhibit IGFBP7 activity specifically. In certain embodiments, an IGFBP7 inhibitor may comprise a gene editing composition such as, but not limited to, a CRISPR system for targeting IGFBP7 for gene knockdown and/or to reduce IGFBP7 activity level.

In certain embodiments, an IGFBP7 inhibitor may comprise, for example, a virus or other vector which is able to target IGFBP7 via, for example, gene silencing. By way of non-limiting example, in certain embodiments, an IGFBP7 inhibitor may comprise an Adeno-associated virus (AAV), or other suitable vector, which is able to deliver and/or express an shRNA sequence targeting IGFBP7 in a target cell. In an embodiment, an IGFBP7 inhibitor may include an Adeno-associated virus (AAV), Serotypes: Caspsid AAV-9, ITR AAV-2, employing a U6 promoter and a transgene for providing an Igfbp7-targeting shRNA for human, mouse, and rat, for example (Genebank RefSeq: NM_001553, NM_00115918, NM_001013048). In certain embodiments, an optional reporter/marker may be included, such as an eGFP driven by a CMV promoter. As will be understood, the shRNA sequence may be selected to suit the particular application. In certain embodiments, the shRNA may include, for example, the following sequence:

```
                                      (SEQ ID NO: 39)
5'-CCGG-GCTGGTATCTCCTCTAAGTAACTCGAGTTACTTAGAGGAGAT
ACCAGC-TTTTTG-3'
``` for which a targeting sequence may be:

```
                                      (SEQ ID NO: 40)
           GCTGGTATCTCCTCTAAGTAA
``` and a hairpin loop sequence of:

```
                                      (SEQ ID NO: 41)
                 CTCGAG
``` with a sequence of:

```
                                      (SEQ ID NO: 42)
                 TTTTT
``` terminating the shRNA expression for U6 promoter.

As will be understood, the skilled person will be able to select a suitable shRNA sequence depending on application. In certain embodiments, a control virus may be used as a comparator, such as AAV9-GFP-U6-scrmb-shRNA (Vector BioLabs, Lot #170529-170623).

Exemplary non-limiting examples of human IGFBP7 inhibitors are described below in Examples 7 and 8, wherein two IGFBP7 inhibitors in the form of two different human IGFBP7 mRNA-targeting siRNAs are described in detail. The sense strand primary nucleic acid sequences of these two siRNAs are provided in FIG. 1F as SEQ ID NO: 9 and SEQ ID NO: 10, and the antisense strand primary nucleic acid sequences of these two siRNAs are provided in FIG. 1G as SEQ ID NO: 11 and SEQ ID NO: 12, respectively. In Examples 7 and 8, the siRNAs each carried two 3' overhang DNA T nucleotides on their sense strands, and either a DNA "GC" or DNA "CA" two nucleotide 3' overhang on their antisense strands as follows:

```
(siRNA 1 sense strand, uppercase = RNA, lower
case = DNA):
                                        SEQ ID NO: 9
UGGUAUCUCCUCUAAGUAAtt (siRNA 2 sense strand, uppercase = RNA, lower
case = DNA):
                                        SEQ ID NO: 10
CGAGCAAGGUCCUUCCAUAtt (siRNA 1 antisense strand, uppercase = RNA, lower
case = DNA)
                                        SEQ ID NO: 11
UUACUUAGAGGAGAUACCAgc (siRNA 2 antisense strand, uppercase = RNA, lower
case = DNA)
                                        SEQ ID NO: 12
UAUGGAAGGACCUUGCUCGca
```

In certain embodiments, it will be understood that an IGFBP7 inhibitor may comprise more than one IGFBP7 inhibiting agent. Such IGFBP7 inhibiting agents may be used together or in combination, and may for example be administered together as a mixture, or administered separately either simultaneously or sequentially, or both. For example, an IGFBP7 inhibitor may comprise two different siRNAs, each targeting a different region of the IGFBP7 mRNA. By way of example, the siRNAs described in Examples 7 and 8, and shown in SEQ ID NOs: 9/11 and 10/12, may be used together as a mixture, or may be used separately either simultaneously or sequentially with one another, or both.

The person of skill in the art having regard to the teachings herein will recognize that many different IGFBP7 inhibitors may be possible. A suitable IGFBP7 inhibitor may be any suitable small molecule, biomolecule, or other construct or molecule able to reduce IGFBP7 expression levels, IGFBP7 protein levels, and/or IGFBP7 protein activity.

The person of skill in the art will recognize that the expression of a particular gene within a cell may be reduced, prevented, or "silenced" using any of a variety of well-known methods. By way of non-limiting example, a gene silencing nucleic acid may be used to reduce, prevent, or silence the expression of a target gene. Without wishing to be limiting, suitable gene silencing nucleic acids may include short interfering RNAs (siRNAs), antisense oligonucleotides (AONs), short hairpin RNAs (shRNAs), microRNAs (miRNAs), or other RNA interference (RNAi) or antisense gene silencing triggers, among others (see, for example, Gaynor et al., RNA interference: a chemist's perspective. Chem. Soc. Rev. (2010) 39: 4196-4184; Bennett et al., RNA Targeting Therapeutics: Molecular Mechanisms of Antisense Oligonucleotides as a Therapeutic Platform, Annual Review of Pharmacology and Toxicology, (2010) 50: 259-293). Given a particular gene sequence, the person of skill in the art will be able to design gene silencing oligonucleotides capable of targeting said gene or mRNA transcribed therefrom, reducing expression (either transcription, translation, or both) of the gene. For example, an siRNA antisense strand, or an antisense oligonucleotide, which is fully or substantially complementary to a region of the gene-expressed mRNA sequence may be prepared, and used for targeted gene silencing by triggering RISC or RNase H-mediated mRNA degradation. As well, gene expression may be decreased by other pre- or post-transcriptional gene silencing techniques known in the art.

Various software-based tools are available for designing siRNAs or AONs for targeting a particular gene, including those available from the Whitehead Institute (http://sirna.wi.mit.edu/) or those available from commercial providers of siRNAs. Gene silencing nucleic acids may be prepared as described in, for example, Current Protocols in Nucleic Acids Chemistry, published by Wiley.

Gene silencing oligonucleotides may be introduced into cells using any of a number of well-known methods. Expression vectors (either viral, plasmid, or other) may be transfected, electroporated, or otherwise introduced into cells, which may then express the gene silencing nucleotide(s). Alternatively, gene silencing nucleotides themselves may be directly introduced into cells, for example via transfection or electroporation (i.e. using a transfection reagent such as but not limited to Lipofectamine™, Oligofectamine™, or any other suitable delivery agent known in the art), or via targeted gene or nucleic acid delivery vehicles known in the art. Many delivery vehicles and/or agents are well-known in the art, several of which are commercially available. Delivery strategies for gene silencing nucleic acids are described in, for example, Yuan et al., Expert Opin. Drug Deliv. (2011) 8:521-536; Juliano et al., Acc. Chem. Res. (2012) 45: 1067-1076; and Rettig et al., Mol. Ther. (2012) 20:483-512. Examples of transfection methods are described in, for example, Ausubel et al., (1994) Current Protocols in Molecular Biology, John Wiley & Sons, New York. Expression vector examples are described in, for example, Cloning Vectors: A Laboratory Manual (Pouwels et al., 1985, Supp. 1987).

It will be understood that gene expression may refer to the production of a polypeptide from the nucleic acid sequence of a gene. Gene expression may include both transcription and translation processes, and so gene expression may refer to production of a nucleic acid sequence such as an mRNA (i.e. transcription), production of a protein (i.e. translation), or both.

The skilled person will further understand that antibodies, or antibody fragments, targeting one or more of the amino acids, nucleic acids, proteins, or enzymes described herein, such as monoclonal or polyclonal antibodies or $F_{ab}$ fragments thereof, may be generated for targeting a particular amino acid, nucleic acid, protein or enzyme target using standard laboratory techniques. By way of non-limiting example, monoclonal antibodies to a particular target (i.e. IGFBP7 protein, the sequence of which is shown in FIG. 1B as SEQ ID NO: 3 or 4) may be prepared using a hybridoma technique (see, for example, Harlow et al., Antibodies: A Laboratory Manual, (Cold Spring Harbor Laboratory Press, 2nd ed. 1988); Hammerling, et al., in: Monoclonal Antibodies and T-Cell Hybridomas pp 563-681 (Elsevier, N.Y., 1981)). The person of skill in the art will be aware of methods and techniques for preparing antibodies for a particular amino acid, protein, nucleic acid, or enzyme target. Such antibodies may be used to bind an amino acid, protein, nucleic acid, or enzyme target, preventing it from performing its regular function, resulting in a similar outcome to that arising from gene silencing of the same amino acid, nucleic acid, protein or enzyme. Therefore, in certain embodiments, antibodies may be used in place of gene silencing nucleic acids for targeting or "silencing" a particular gene, and are also considered as IGFBP7 inhibitors.

Examples of an IGFBP7-targeting antibody may include, for example, Rabbit monoclonal Anti-IGFBP7 antibody (Abcam, ab171085), Rabbit polyclonal Anti-IGFBP7 antibody (Abcam, ab74169), and Goat polyclonal Anti human IGFBP7 antibody (R&D Systems, AF1334).

It will be understood that compounds and/or compositions comprising or consisting of one or more of the nucleic acid and/or polypeptides or antibodies as described herein may be used. Compositions may additionally comprise one or more pharmaceutically acceptable diluents, carriers, excipients, or buffers. Compositions may be used for administering one or more nucleic acids and/or polypeptides to a cell in vitro or in vivo.

Introduction of a gene, in the context of inserting a nucleic acid sequence into a cell, refers to "transfection", "transformation", or "transduction", and includes the incorporation or introduction of a nucleic acid sequence into a eukaryotic cell where the nucleic acid sequence may optionally be incorporated into the genome of the cell, or transiently expressed (for example, transfected mRNA). A protein or enzyme may be introduced into a cell by delivering the protein or enzyme itself into the cell, or by expressing an mRNA encoding the protein or enzyme within the cell, leading to its translation.

As referenced herein, percent (%) identity or % sequence identity with respect to a particular sequence, or a specified portion thereof, may be defined as the percentage of nucleotides or amino acids in the candidate sequence identical with the nucleotides or amino acids in the subject sequence (or specified portion thereof), after aligning the sequences and introducing gaps, if necessary, to achieve the maximum percent sequence identity, as generated by the program WU-BLAST-2.0 with search parameters set to default values (Altschul et al., J. Mol. Biol. (1990) 215:403-410; website at blast.wustl.edu/blast/README.html).

By way of example, a % identity value may be determined by the number of matching identical nucleotides or amino acids divided by the sequence length for which the percent identity is being reported. Percent (%) amino acid sequence similarity may be determined by the same calculation as used for determining % amino acid sequence identity, but may, for example, include conservative amino acid substitutions in addition to identical amino acids in the computation. Oligonucleotide alignment algorithms such as, for example, BLAST (GenBank; using default parameters) may be used to calculate sequence identity %.

An alternative indication that two nucleic acid sequences may be substantially identical is that the two sequences hybridize to each other under moderately stringent, or preferably stringent, conditions. Hybridization to filter-bound sequences under moderately stringent conditions may, for example, be performed according to Ausubel, et al. (eds), 1989, Current Protocols in Molecular Biology, Vol. 1, Green Publishing Associates, Inc., and John Wiley & Sons, Inc., New York, at p. 2.10.3. Alternatively, hybridization to filter-bound sequences under stringent conditions may, for example, be performed according to Ausubel, et al. (eds), 1989, supra. Hybridization conditions may be modified in accordance with known methods depending on the sequence of interest (see, for example, Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, by way of non-limiting example, stringent conditions may be about 5° C. lower than the thermal melting point for the specific sequence at a defined ionic strength and pH.

It will be understood that the specific amino acid or nucleic acid sequence of a particular gene may vary from species to species. By way of example, according to the BLAST Tool provided by the NCBI, the human IGFBP7 amino acid sequence has homologs in other species falling between about an 85%-100% sequence identity range. IGFBP7 is generally highly conserved in mammals, and thus the amino acid sequence of IGFBP7 has about 92% sequence identity between human and rodent (e.g. rat and mouse). Homologous sequences from different species may represent, or be considered as, variants of a particular gene.

As will be known to one of skill in the art, nucleotide sequences for expressing a particular gene may encode or include features as described in "Genes VII", Lewin, B. Oxford University Press (2000) or "Molecular Cloning: A Laboratory Manual", Sambrook et al., Cold Spring Harbor Laboratory, 3rd edition (2001). A nucleotide sequence encoding a polypeptide or protein may be incorporated into a suitable vector, such as a commercially available vector. Vectors may also be individually constructed or modified using standard molecular biology techniques, as outlined, for example, in Sambrook et al. (Cold Spring Harbor Laboratory, 3rd edition (2001)). The person of skill in the art will recognize that a vector may include nucleotide sequences encoding desired elements that may be operably linked to a nucleotide sequence encoding a polypeptide or protein. Such nucleotide sequences encoding desired elements may include transcriptional promoters, transcriptional enhancers, transcriptional terminators, translational initiators, translational terminators, ribosome binding sites, 5'-untranslated region, 3'-untranslated regions, cap structure, poly A tail, and/or an origin of replication. Selection of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

It will be understood that contemplated herein is a nucleic acid comprising a sequence:
  a) encoding a protein as defined herein, or a fragment thereof;
  b) that is the complement of a sequence encoding a protein as defined herein, or a fragment thereof;
  c) that is capable of hybridizing to a nucleic acid encoding a protein as defined herein or fragment thereof under stringent hybridization conditions; or
  d) that exhibits greater than or equal to about 70%, or greater than or equal to about 85%, sequence identity with the nucleic acid defined in a) or b) or another nucleic acid sequence as described herein, for example, but not limited to, 86%, 87%, 88%, 89%, 90%, 91%, 92%, 93%, 94%, 95%, 96%, 97%, 98%, 99%, or 100%. The nucleic acid may also be characterized by a range of identities, for example any two of the percentages outlined above.

Derivative or variant nucleic acid molecules of a particular nucleic acid molecule may include sequences that hybridize to the nucleic acid sequence as discussed herein, or a sequence complementary to a nucleic acid sequence as discussed here. The stringency of hybridization may be controlled by temperature, ionic strength, pH, and the presence of denaturing agents such as formamide during hybridization and washing. Conditions routinely used would be well known to those in the art (see, for example, Current Protocol in Molecular Biology, Vol. I, Chap. 2.10, John Wiley & Sons, Publishers (1994)).

In further embodiments, there are described herein treatment methods, and uses, relating to insulin-like growth factor-binding protein 7 (IGFBP7) inhibitors for the treatment or prevention of heart failure, IGFBP7-related metabolic diseases, and related diseases or conditions as already described in detail above which additionally comprise:

administering an insulin-like growth factor 1 receptor (IGF-1R) inhibitor to said subject to inhibit IGF-1R expression and/or activity levels in said subject.

In such embodiments, the IGFBP7 inhibitor is to be used in combination with an IGF-1R inhibitor. For example, the IGFBP7 inhibitor and the IGF-1R inhibitor may be used simultaneously (i.e. co-administered), sequentially (i.e. administered in separate administrations spaced apart by a given time period), or in combination (i.e. administered as a single composition) with one another. As described in further detail below in Example 8, such combination treatments may, in certain embodiments, provide further benefit or enhancement of certain therapeutic effects such as a reduction in IGF-1/insulin induced AKT activation.

According to the NCBI, insulin-like growth factor 1 receptor (IGF-1R) is a transmembrane tyrosine kinase-type receptor activated by IGF-1 and IGF-2. The human IGF-1R gene nucleic acid sequence may be found on the NCBI website using the following accession number and chromosome location information: Location: 15q26.3 NC_000015.10 (98648539 . . . 98964530). The mRNA transcribed from this gene is shown in FIG. 1C as SEQ ID NO: 5 (human IGF-1R mRNA sequence, Accession number NM_000875.4, human insulin like growth factor 1 receptor, transcript variant 1) and shown in FIG. 1D as SEQ ID NO: 6 (human IGF-1R mRNA sequence, Accession number NM_001291858.1, homan insulin like growth factor 1 receptor, transcript variant 2). The amino acid sequence of human IGF-1R protein is shown in FIG. 1E as SEQ ID NO: 7 (human IGF-1R protein sequence, Accession number NP_000866.1, isoform 1 precursor) and SEQ ID NO: 8 (human IGF-1R protein sequence, Accession number NP 001278787.1, isoform 2 precursor). Mouse IGF-1R gene, mRNA, and protein sequences are similar to those of the human sequences, and can be found on the NCBI website as accession numbers NM_010513.2 (Mus musculus insulin-like growth factor I receptor (Igf1r), mRNA) and NP_034643.2 (insulin-like growth factor 1 receptor precursor [Mus musculus]).

IGF-1R inhibitors for targeting or inhibiting IGF-1R expression and/or activity levels have been identified. The person of skill in the art will recognize that a suitable IGF-1R inhibitor may be any suitable inhibitor able to reduce IGF-1R expression levels, activity levels, or both. By way of non-limiting example, a suitable IGF-1R inhibitor may be a gene silencing nucleic acid (such as, but not limited to, an siRNA, an antisense oligonucleotide, a short-hairpin RNA, a miRNA, a dicer-substrate RNA, a DNAzyme, or an aptamer targeting the IGF-1R gene or the IGF-1R messenger RNA so as to reduce expression thereof), an anti-IGF-1R antibody (such as a monoclonal, polyclonal, murine, chimeric, humanized, or human antibody targeting an IGF-1R epitope so as to interfere with IGF-1R activity), a small molecule inhibitor of IGF-1R, or another IGF-1R inhibiting agent. Such gene silencing nucleic acids and/or antibodies may be designed and developed as already discussed above with reference to IGFBP7 gene silencing nucleic acids and antibodies.

In certain embodiments, it will be understood that an IGF-1R inhibitor may comprise more than one IGF-1R inhibiting agent. Such IGF-1R inhibiting agents may be used together or in combination, and may for example be administered together as a mixture, or administered separately either simultaneously or sequentially, or both.

Exemplary non-limiting examples of human IGF-1R inhibitors are described below in Example 8, wherein a small-molecule IGF-1R inhibitor in the form of picropodophyllin (ppp) is described in detail.

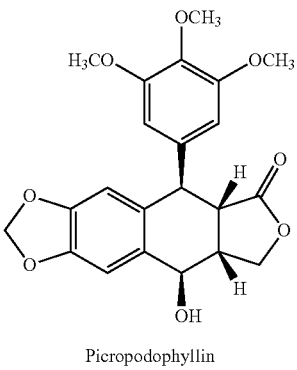 [SMILES: COc1cc([C@@H]2c3cc4c(cc3[C@H](O)[C@H]3COC(=O)[C@@H]23)OCO4)cc(OC)c1OC]

Picropodophyllin

The person of skill in the art having regard to the teachings herein will recognize that many different IGF-1R inhibitors may be possible. A suitable IGF-1R inhibitor may be any suitable small molecule, biomolecule, or other construct or molecule able to reduce IGF-1R expression levels, IGF-1R protein levels, and/or IGF-1R protein activity.

The person of skill in the art will further understand that IGFBP7 inhibitors and IGR-1R inhibitors may be administered to a subject in need thereof using any suitable administration technique, and in any suitable dosage form, as will be known in the art. By way of example, administration of these inhibitors may be performed intranasally via aerosol, by oral dosage, intravenously by injection, or via local injection, for example, depending on the particular inhibitors used and the intended application. The person of skill in the art will be able to select a suitable administration method to suit particular applications and/or particular subject needs.

The person of skill in the art will understand that biomolecules and/or compounds described herein may be provided in pharmaceutical compositions together with a pharmaceutically acceptable diluent, carrier, or excipient, and/or together with one or more separate active agents or drugs as part of a pharmaceutical combination or pharmaceutical composition.

Biomolecules, compounds, and/or compositions as described herein may include one or more pharmaceutically acceptable excipients, diluents, and/or carriers. A pharmaceutically acceptable carrier, diluent, or excipient may include any suitable carrier, diluent, or excipient known to the person of skill in the art. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, buffers, glidants, and disentegrants known in the art (see, for example, Remington: The Science and Practice of Pharmacy (2006)). Examples of pharmaceutically acceptable carriers, diluents, and excipients may be found in, for example, Remington's Pharmaceutical Sciences (2000—20th edition) and in the United States Pharmacopeia: The National Formulary (USP 24 NF19) published in 1999.

In certain embodiments, the biomolecules, compounds, and/or pharmaceutical compositions may be administered in a treatment regimen simultaneously, sequentially, or in combination with other drugs or pharmaceutical compositions, either separately or as a combined formulation or combination.

In another embodiment, there is provided herein a method for identifying an IGFBP7 inhibitor, said method comprising:

screening a library of potential IGFBP7 inhibitor candidates by administering potential IGFBP7 inhibitor candidates of the library to cardiac cells and determining the effect of each potential IGFBP7 inhibitor candidate on the expression level, activity level, or both, of IGFBP7 in said cardiac cells following administration;

wherein an observed reduction in IGFBP7 expression level, activity level, or both, following potential IGFBP7 inhibitor candidate administration identifies the potential IGFBP7 inhibitor candidate as an IGFBP7 inhibitor.

It will be understood that a library of potential IGFBP7 inhibitor candidates may include any suitable collection of small molecules, biomolecules, and/or other compounds or compositions. Libraries may comprise similar or related compounds/molecules, or may comprise a variety of different types of compounds/molecules. By way of example, the person of skill in the art will be aware of several libraries suitable for such screening applications which have been made available through academic institutions and private or commercial organizations. These libraries are commonly used in high-throughput screens as part of drug discovery efforts to identify lead compounds, and are well-known in the art.

It will further be understood that, in certain embodiments, the cardiac cells of the method may be cultured in vitro, or may be cardiac cells of an animal model such as a mouse model. For example, the cardiac cells may be human cardiac myocytes, or cardiac cells of mice animal models being used for inhibitor candidate screening.

In embodiments of such methods for identifying IGFBP7 inhibitors, the effect of each potential IGFBP7 inhibitor candidate on the expression level, activity level, or both, of IGFBP7 in the cardiac cells may be determined by RT-PCR, immunoblotting, or immunostaining. Alternatively, or in addition, the effect of each potential IGFBP7 inhibitor candidate on the expression level, activity level, or both, of IGFBP7 in the cardiac cells may be determined by assessing protection from pressure induced overload heart failure, attenuation of pressure overload induced cardiac fibrosis in TAC, stress-induced cellular senescence levels, IGF-1/insulin receptor-dependent signaling levels, cardiac hypertrophy levels in TAC hearts, hypertrophic and cellular senescence signaling levels, or depression of IGF-1/Insulin induced AKT activation. Exemplary experimental methods for such determinations are provided in Examples 1-8 described below. The skilled person will understand that various changes, alternative techniques, or substitutions may be made to the experimental methods provided in these Examples, and that the following Examples are intended to be non-limiting.

In still another embodiment, there is provided herein a method for identifying a therapeutic for the treatment or prevention of heart failure or an insulin-like growth factor-binding protein 7 (IGFBP7)-related metabolic disease, said method comprising:

screening a library of potential therapeutic candidates by administering potential therapeutic candidates of the library to cardiac cells and determining the effect of each potential therapeutic candidate on the expression level, activity level, or both, of IGFBP7 in said cardiac cells following administration;

wherein an observed reduction in IGFBP7 expression level, activity level, or both, following potential therapeutic candidate administration identifies the potential therapeutic candidate as a therapeutic for the treatment or prevention of heart failure or an IGFBP7-related metabolic disease.

It will be understood that a library of potential therapeutic candidates may include any suitable collection of small molecules, biomolecules, and/or other compounds or compositions. Libraries may comprise similar or related compounds/molecules, or may comprise a variety of different types of compounds/molecules. By way of example, the person of skill in the art will be aware of several libraries suitable for such screening applications which have been made available through academic institutions and private or commercial organizations. These libraries are commonly used in high-throughput screens as part of drug discovery efforts to identify lead compounds, and are well-known in the art.

It will further be understood that, in certain embodiments, the cardiac cells of the method may be cultured in vitro, or may be cardiac cells of an animal model such as a mouse model. For example, the cardiac cells may be human cardiac myocytes, or cardiac cells of mice animal models being used for therapeutic candidate screening.

In embodiments of such methods for identifying therapeutics for the treatment or prevention of heart failure or an insulin-like growth factor-binding protein 7 (IGFBP7)-related metabolic disease, the effect of each potential therapeutic candidate on the expression level, activity level, or both, of IGFBP7 in the cardiac cells may be determined by RT-PCR, immunoblotting, or immunostaining. Alternatively, or in addition, the effect of each potential therapeutic candidate on the expression level, activity level, or both, of IGFBP7 in the cardiac cells may be determined by assessing protection from pressure induced overload heart failure, attenuation of pressure overload induced cardiac fibrosis in TAC, stress-induced cellular senescence levels, IGF-1/insulin receptor-dependent signaling levels, cardiac hypertrophy levels in TAC hearts, hypertrophic and cellular senescence signaling levels, or depression of IGF-1/Insulin induced AKT activation. Exemplary experimental methods for such determinations are provided in Examples 1-8 described below. The skilled person will understand that various changes, alternative techniques, or substitutions may be made to the experimental methods provided in these Examples, and that the following Examples are intended to be non-limiting.

In still another embodiment, there is provided herein a use of IGFBP7 for identifying an IGFBP7 inhibitor, where the IGFBP7 is for use in a screening assay, such as a high-throughput screening assay, in which the effect of potential IGFBP7 inhibitor candidates on an expression level, activity level, or both, of the IGFBP7 in cardiac cells is determined.

In yet another embodiment, there is provided herein a use of IGFBP7 for identifying a therapeutic for the treatment or prevention of heart failure or an insulin-like growth factor-binding protein 7 (IGFBP7)-related metabolic disease, where the IGFBP7 is for use in a screening assay, such as a high-throughput screening assay, in which the effect of potential therapeutic candidates on an expression level, activity level, or both, of the IGFBP7 in cardiac cells is determined.

In yet another embodiment, there is provided herein a method for treating a heart disease or insulin-like growth factor-binding protein 7 (IGFBP7)-related metabolic disease in a subject in need thereof, said method comprising:

treating the subject with a heart disease or IGFBP7-related metabolic disease therapeutic, monitoring IGFBP7 expression levels, activity levels, or both, in a companion diagnostic assay to evaluate efficacy of the therapeutic in the subject; and optionally, adjusting therapeutic treatment of the subject to improve results of the companion diagnostic assay when subsequently repeated.

In still another embodiment, there is provided herein a use of IGFBP7 in a companion diagnostic assay for monitoring treatment of heart disease or insulin-like growth factor-binding protein 7 (IGFBP7)-related metabolic disease in a subject in need thereof.

The person of skill in the art will recognize that a companion diagnostic may be any suitable assay or test used in connection with a therapeutic treatment in order to determine and/or monitor the efficacy of the therapeutic treatment in a subject. The companion diagnostic may be used, for example, to determine whether a particular subject is susceptible to a particular treatment, whether a particular subject is benefiting (or will benefit) from a particular treatment, whether a particular treatment should be adjusted (i.e. increased or decreased dosage, altered dosage regimen, altered administration route, etc. . . . ) or substituted (i.e. switched to an alternative therapeutic treatment) to improve therapeutic benefit to the subject, or any combination thereof.

The following experimental Examples are provided to further illustrate certain embodiments of the present invention. These Examples are intended for the person of skill in the art, and are not meant to be limiting in any way.

Example 1: IGFBP7 is Unregulated in the Stressed Myocardium

Figure 2:
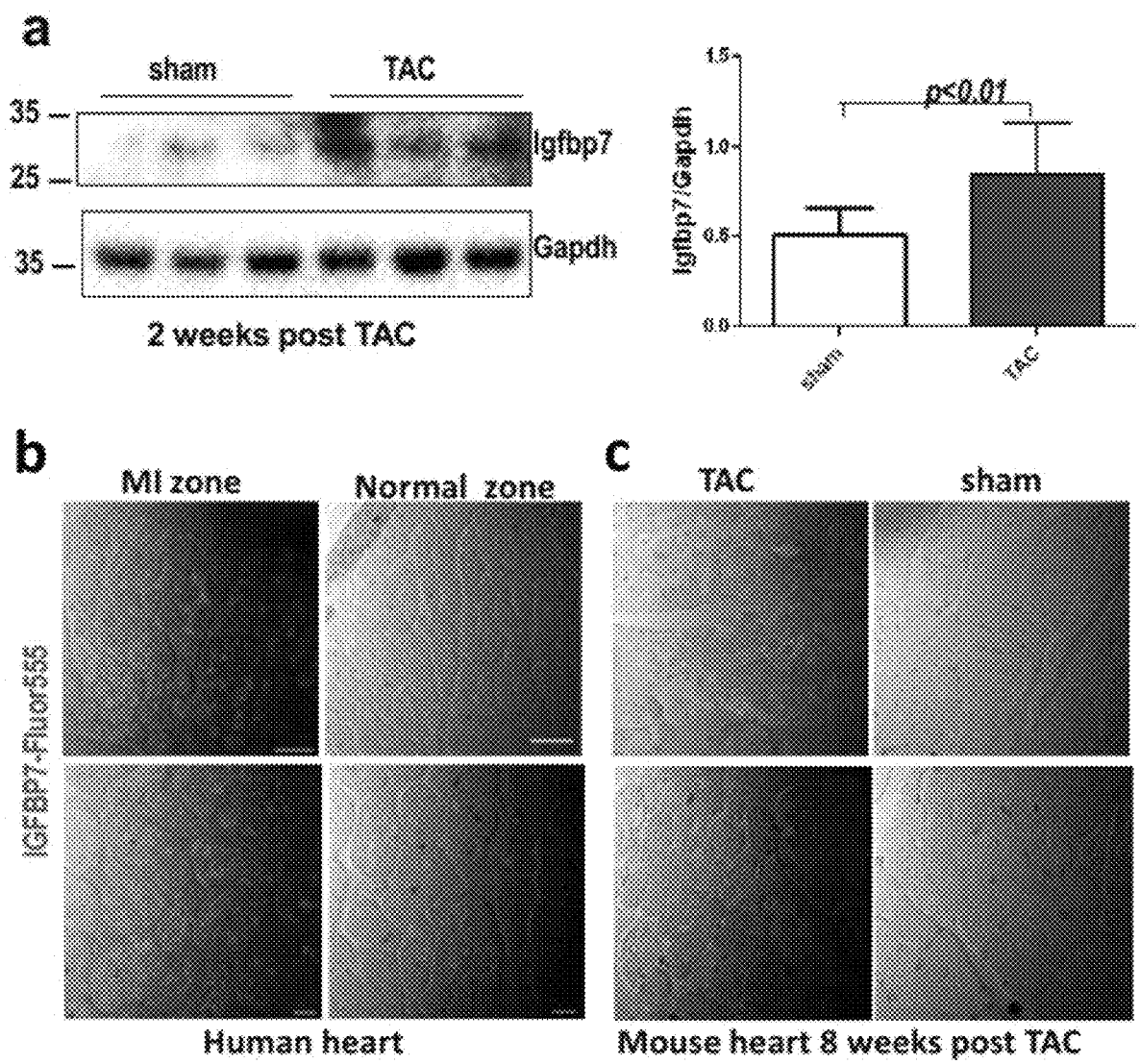
FIG. 2 shows that IGFBP7 is unregulated in the stressed myocardium. (a) shows representative immunoblotting and quantification. IGFBP7 protein expression is markedly increased in C57BL/6 mouse TAC heart compared to sham operated control 2 weeks post-surgery. Expression levels were normalized to GAPDH. n=3 per group, p<0.01 (unpaired two-tailed Student t-tests). (b) and (c) show representative confocal microscopy images. (b) shows human heart sections immunofluoresently stained with anti-IGFBP7 antibody. IGFBP7 expression (red) was significantly increased in infarct zone of a patient suffering from myocardial infarction, compared with normal zone of the same patient. Human heart sections were probed with anti-IG-FBP7 antibody, and were visualized by staining with Alexa Fluor 555 secondary antibody. Nuclear staining was accomplished with DEPI (blue). (c) shows that IGFBP7 immunofluoresent staining (red) was significantly elevated in C57BL/6 mouse TAC heart compared to sham control 8 weeks post-surgery. Nuclear staining was accomplished with DEPI (blue). In all images, scale bars=30 μm in upper panels and 10 μm in lower panels.

This example indicates that under the conditions tested, IGFBP7 is unregulated in the stressed myocardium. Experimental protocols are provided in the Methods section below, and results are provided in FIG. 2.

To investigate the role of IGFBP7 in the development of heart failure, IGFBP7 protein expression in heart tissue biopsies from a heart failure patient who suffered from myocardial infarction (MI) was examined. FIG. 2(a) shows representative immunoblotting and quantification. As shown in FIG. 2(a), IGFBP7 protein expression is markedly increased in C57BL/6 mouse transaortic constriction (TAC) heart compared to sham operated control 2 weeks post-surgery. FIGS. 2(b) and 2(c) show representative confocal microscopy images. FIG. 2(b) shows immunofluorescent staining showing that there was a significant increase in IGFBP7 expression in the MI zone as compared to normal zone. In FIG. 2(b), human heart sections immunofluoresently stained with Alexa Fluor 555 labeled anti-IGFBP7 antibody (Rabbit polyclonal anti-IGFBP7 antibody (abcam. ab74169). IGFBP7 expression (red) was significantly increased in infarct zone of a patient suffering from myocardial infarction, compared with normal zone of the same patient. Nuclear staining was accomplished with DEPI (blue). In addition, Igfbp7 protein expression was checked in a murine model of heart failure induced by transverse aortic constriction (TAC) compared to a sham operated control group. Immunofluorescent staining indicated a significant increased Igfbp7 expression in cardiomyocytes of TAC heart compared with sham operated heart 8 weeks post operation (FIG. 2(c)). FIG. 2(c) shows that IGFBP7 immunofluoresent staining (red) was significantly elevated in C57BL/6 mouse TAC heart compared to sham control 8 weeks post-surgery. Nuclear staining was also accomplished with DEPI (blue).

These results were further confirmed by Igfbp7 protein immunoblot in C57BL/6 mouse TAC heart compared to sham operated control 2 weeks post-surgery (unpaired two-tailed Student t test, p=0.01) (FIG. 2(a)).

Together, these experimental results indicate that IGFBP7 is unregulated in the stressed myocardium under the conditions tested.

Figure 3:
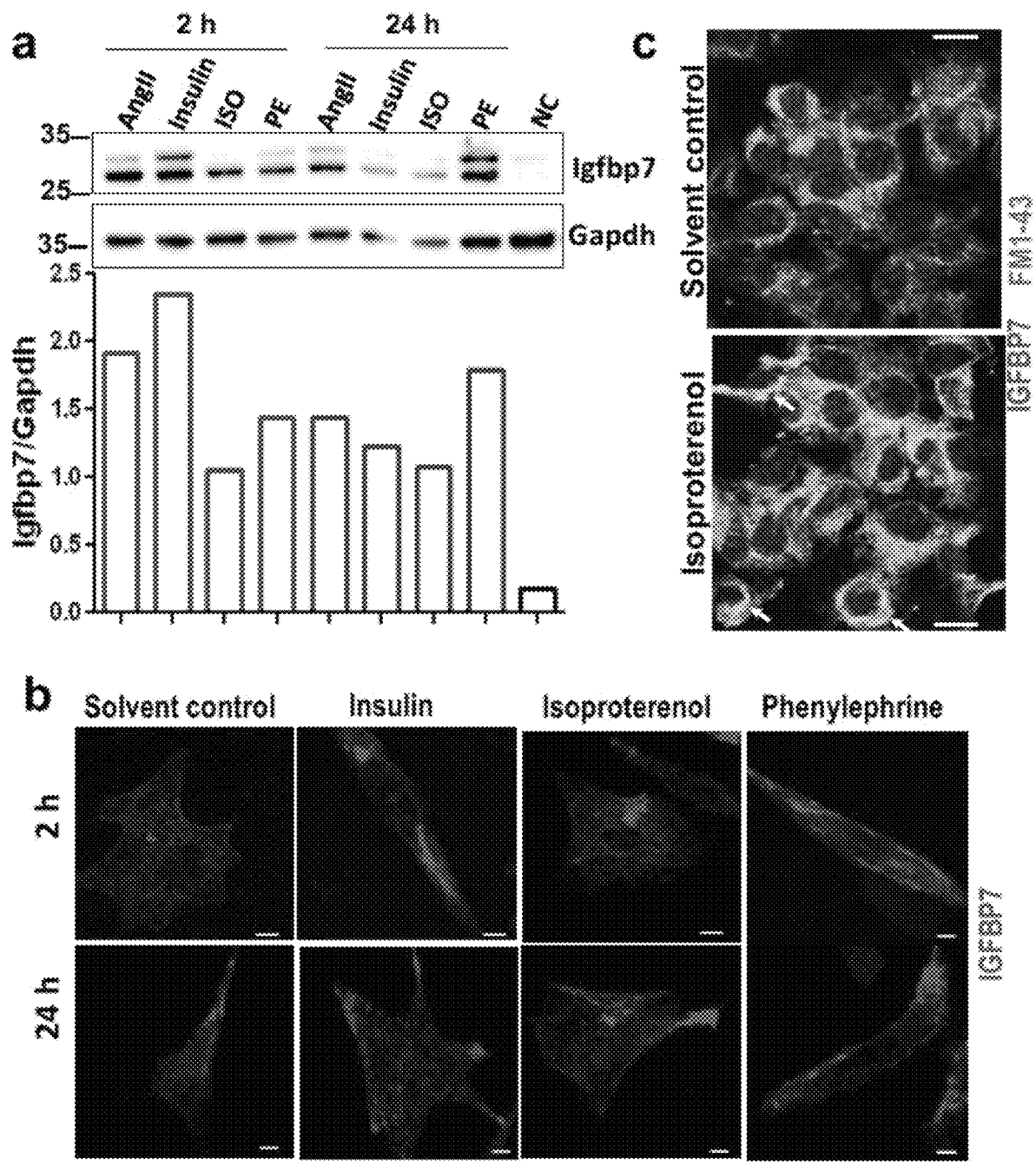
FIG. 3 shows that significantly up-regulated IGFBP7 proteins co-localize with membrane bound vesicles in hypertrophic stimuli treated cardiomyocytes in vitro. (a) Representative immunoblotting showing IGFBP7 protein is significantly up-regulated in rat neonatal cardiomyocytes treated with hypertrophic stimuli; angiotensin II (AngII), 100 nM; insulin, 4 μg/ml; isoproterenol (ISO), 100 nM; phenylephrine (PE), 200 nM; NC, solvent treated control. (b) and (c) show representative confocal microscopy images. (b) shows increased IGFBP7 (Red) movement to cell membrane region upon hypertrophic stimuli in rat neonatanal cardiomyocyte. IGFBP7 were immunofluoresently stained with anti-IGFBP7 antibody and were visualized by staining with Alexa Fluor 555 secondary antibody. (c) shows that upon isoproterenol treatment, IGFBP7 (red) not only moved to cell membrane region, but also co-localized with FM1-43 labeled membrane bound vesicle (green), indicating that IGFBP7 was trapped into the membrane bound vesicles for secretion. Scale bars=10 μm in all images.

Example 2: Significantly Up-Regulated IGFBP7 Proteins Co-Localize with Membrane Bound Vesicles in Hypertrophic Stimuli Treated Cardiomyocytes In Vitro This example indicates that under the conditions tested, up-regulated IGFBP7 proteins co-localize with membrane bound vesicles in hypertrophic stimuli-treated cardiomyocytes in vitro. Experimental protocols are provided in the Methods section below, and results are provided in FIG. 3.

Rat neonatal cardiomyocytes (rNCM) were challenged with several hypertrophic stimuli; again, Igfbp7 protein is significantly up-regulated in treated group compared with solvent treatment control group as shown by immunobot (FIG. 3(a)). In order to investigate where Igfbp7 is localized under stress, immunofluorescent staining were used to visualize Igfbp7 in rNCM 2 and 24 hours post treatment. As shown in FIG. 3(b), Igfbp7 were evenly distributed in untreated control cells. Hypertrophic stimuli not only led to increased Igfbp7 expression, but also led to Igfbp7 being localized to the cell membrane. Co-immunostaining with FM1-43 as shown (FIG. 3(c)), upon isoproterenol treatment, Igfbp7 (red) not only moved to cell membrane region, but also co-localized with FM1-43 labeled membrane bound vesicle (green), indicating Igfbp7 was trapped into the membrane bound vesicles for secretion. The robust induction of IGFBP7 protein expression in the heart and in cardiomyocytes in vitro under pathological stress conditions suggests that IGFBP7 participates in stress induced cardiac hypertrophic remodeling.

Indeed, FIG. 3(a) shows representative immunoblotting showing that IGFBP7 protein is significantly up-regulated in rat neonatal cardiomyocytes treated with hypertrophic stimuli: angiotensin II (AngII), 100 nM; insulin, 4 µg/ml; isoproterenol (ISO), 100 nM; and phenylephrine (PE), 200 nM. NC represents solvent treated control. FIGS. 3(b) and 3(c) show representative confocal microscopy images. FIG. 3(b) shows increased IGFBP7 (Red) movement to cell membrane region upon hypertrophic stimuli in rat neonatanal cardiomyocyte. IGFBP7 was immunofluoresently stained with Alexa Fluor 555 labeled anti-IGFBP7 antibody. FIG. 3(c) shows that upon isoproterenol treatment, IGFBP7 (red) not only moved to cell membrane region, but also co-localized with FM1-43 labeled membrane bound vesicle (green), indicating that IGFBP7 was trapped into the membrane bound vesicles for secretion.

Together, these experimental results indicate that up-regulated IGFBP7 proteins co-localize with membrane bound vesicles in hypertrophic stimuli-treated cardiomyocytes in vitro under the conditions tested.

Example 3: Igfbp7 is a Key Regulator of Cardiac Hypertrophic Remodeling. IGFBP7 Deficiency Protects Mice from Pressure Overload Induced Heart Failure This example indicates that under the conditions tested, IGFBP7 deficiency protects mice from pressure overload induced heart failure. Experimental protocols are provided in the Methods section below, and results are provided in FIG. 4.

Surgical models of cardiac pressure overload by transverse aortic constriction (TAC) in mice have provided a platform for studying hypertrophy-diastolic dysfunction induced HEpEF. To investigate Igfbp7's role in the progression of HEpEF, 8-10 weeks old Igfbp7$^{-/-}$ and control wild type (WT) mice on CD-1 genetic background with a body weight at around 25 g were subjected to either TAC or sham operation as previously described (Kuba K, Zhang L, Imai Y, Arab S, Chen M, Maekawa Y, Leschnik M, Leibbrandt A, Markovic M, Schwaighofer J, Beetz N, Musialek R, Neely G G, Komnenovic V, Kolm U, Metzler B, Ricci R, Hara H, Meixner A, Nghiem M, Chen X, Dawood F, Wong K M, Sarao R, Cukerman E, Kimura A, Hein L, Thalhammer J, Liu P P, Penninger J M. Impaired heart contractility in Apelin gene-deficient mice associated with aging and pressure overload. Circ Res. 101, e32-42 (2007)).

To evaluate pressure overload induced cardiac hypertrophy, mice were randomized to sacrifice on weeks 2 and 8 posts TAC. Increased cardiac mass, a key indicator of left ventricular hypertrophy, was measured by heart weight/tibia length ratio (HW/TL). Surprisingly, no significant increases in HW/TL were observed in Igfbp7$^{-/-}$ TAC mice. In contrast, as expected, starting from 2 weeks post TAC, significantly growing HW/TL was observed in WT TAC mice, with this increase is continuing to 8 weeks post TAC (FIG. 4(b)). This was further confirmed by measurement of heart weight/body weight (FIG. 4(i)). Next, cardiac myocytes enlargement was examined, a key factor for cardiac hypertrophy, by measuring cardiac myocyte cross-sectional area in wheat germ agglutinin (WGA) stained left ventricle cross-sections, which confirmed that the retained HW/BW in Igfbp$^{-/-}$ TAC mice was due to abolished cardiac myocyte enlargement as compared to WT mice (FIGS. 4(d) and 4(e)). During the processes leading to adverse cardiac remodeling and heart failure, cardiomyocytes react to stress by reactivating fetal genes (Dirkx E et al, BBA 2013). Real-time quantification of reverse transcription (qRT-PCR) of selected fetal genes in cardiac tissue 2 weeks post TAC reveled Igfbp7 deficiency attenuated Natriuretic Peptide B (nppb), Natriuretic Peptide A (nppa) and Myosin heavy chain 7 (Myh7) activation, in contrast to elevated expression of these genes in WT TAC heart (FIG. 4(f)-4(h)). In addition, significantly increased lung weight/tibia length ratio (LW/TL) (FIG. 4(c)), as well as lung weight/body weight ratio (LW/BW) (FIG. 4(i)), a sign of heart failure, were evidenced in WT mice 8 weeks post TAC. Again, this increase was eliminated by Igfbp7 deficiency. These results suggest Igfbp7 as a key regulator of cardiac hypertrophic remodeling induced heart failure.

Figure 4:
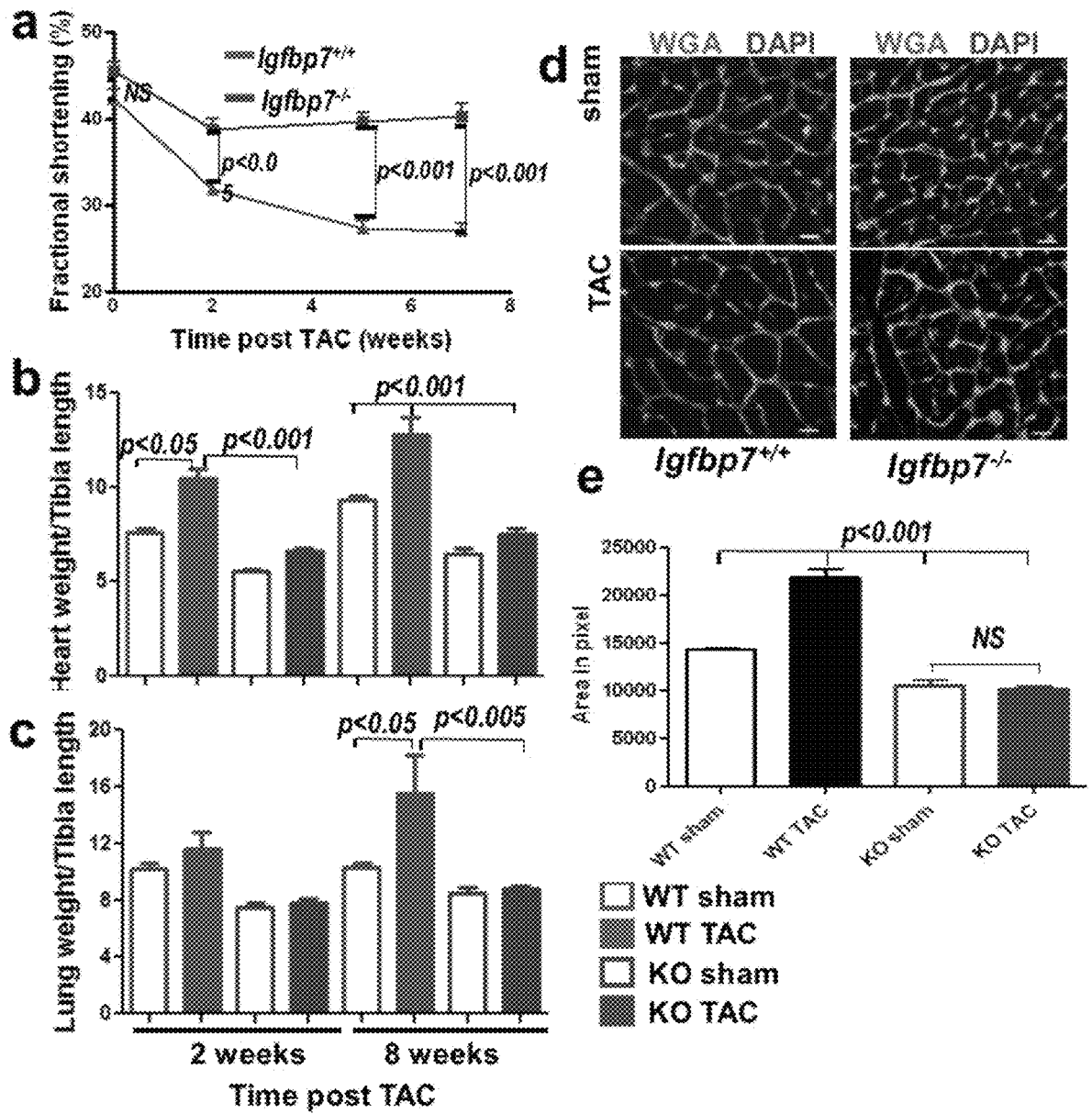
FIG. 4 shows that IGFBP7 deficiency protects mice from pressure overload induced heart failure. IGFBP7$^{-/-}$ and WT mice were subjected to transaortic constriction (TAC) or sham surgery and analyzed 2-8 weeks after the operation. (a) serial echocardiographic measurement of left ventricular (LV) fractional shortening (FS=(LVEDD−LVESD)/LVEDD×100%); n=10-12 for each group; (b) heart weight/tibia length ratios (HW/TL) at 8 weeks, n=10-12 for each group. (c) lung weight/tibia length ratios (LW/TL) at 8 weeks, n=10-12 for each group. (d) Representative wheat germ agglutinin (WGA) staining of transverse heart (8 weeks) cross-sections showing myocyte cross sectional area (scale bars=20 μm). (e) quantitation. (f)-(h) RT-qPCR reveals Igfbp7 deficiency abolished elevated fatal gene expression in TAC heart 2 weeks post surgery. Relative gene expression of (f) Nppb/Hprt1, (g) Nppa/Hprt1, and (h) Myh7/Myh6 ratio were show as fold changes against WT sham group, n=3 per group. (i) shows lung weight/tibia length ratios (LW/TL) at 8 weeks, n=10-12 for each group. In all panels, error bars represent s.e.m., one way ANOVA was used to calculate P values. (j-k) echocardiographic measurement of cardiac function. Transmitral Doppler flow velocity were used to analyze LV diastolic function parameters, like Isovolumlc relaxation time (j), Mitral E/e' Ratio (k) and ESPVR (l), at 8 weeks post-surgery. (l-o) Measurement of cardiac function by Pressure-volume conductance catheterization 8 weeks post sham and TAC surgery. (l) Representative images of pressure-volume loop recordings of WT and Igfbp7$^{-/-}$ sham and TAC mice respectively. (m-n) Parameters of Left ventricular diastolic functions; (m) LV end-diastolic pressure (LVEDP) and (n) Isovolumic relaxation constant (Tau) (Glantz method). (o) Parameters of Left ventricular systolic functions; Ejection fraction (EF) and peak rates of pressure rise (+dP/dt) and pressure fall (−dP/dt). In all panels error bars represent s.e.m., one way ANOVA were used to calculate P values, n=10-12 mice/group.
Figure 4:
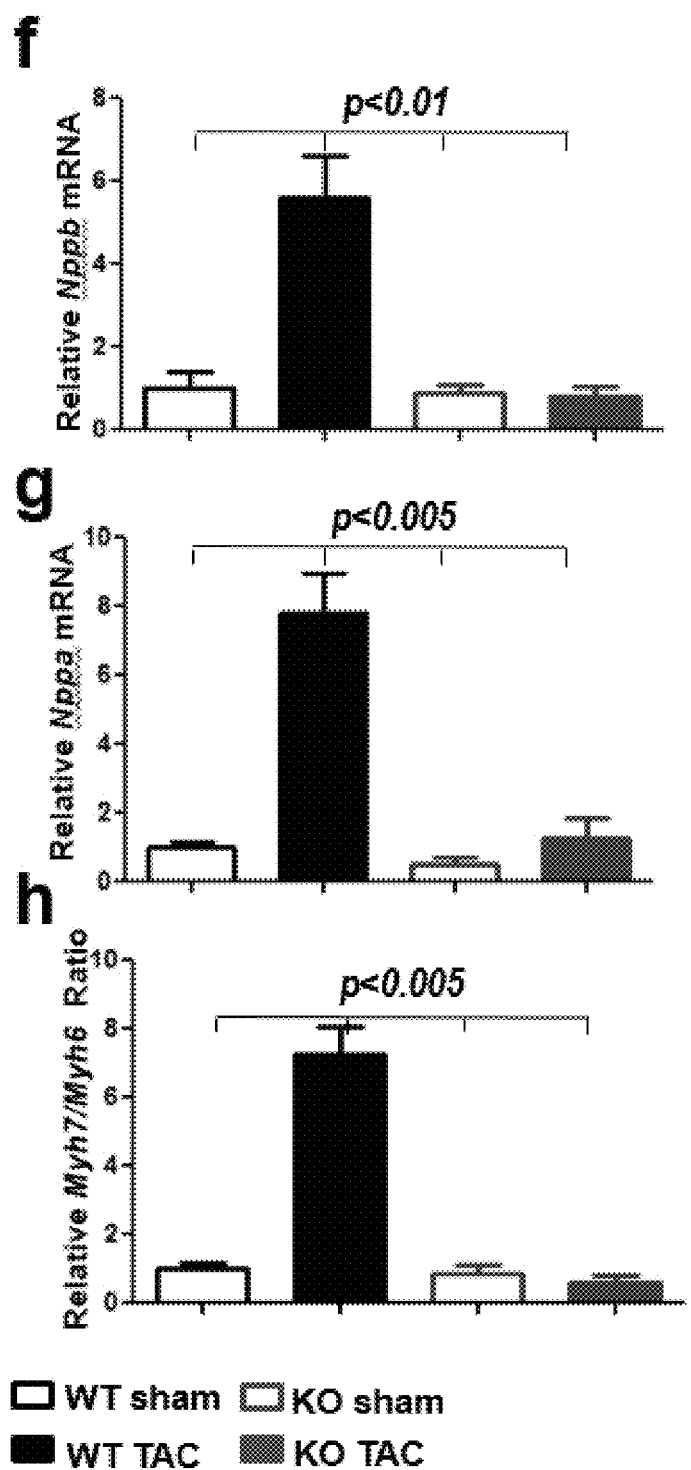
Figure 4:
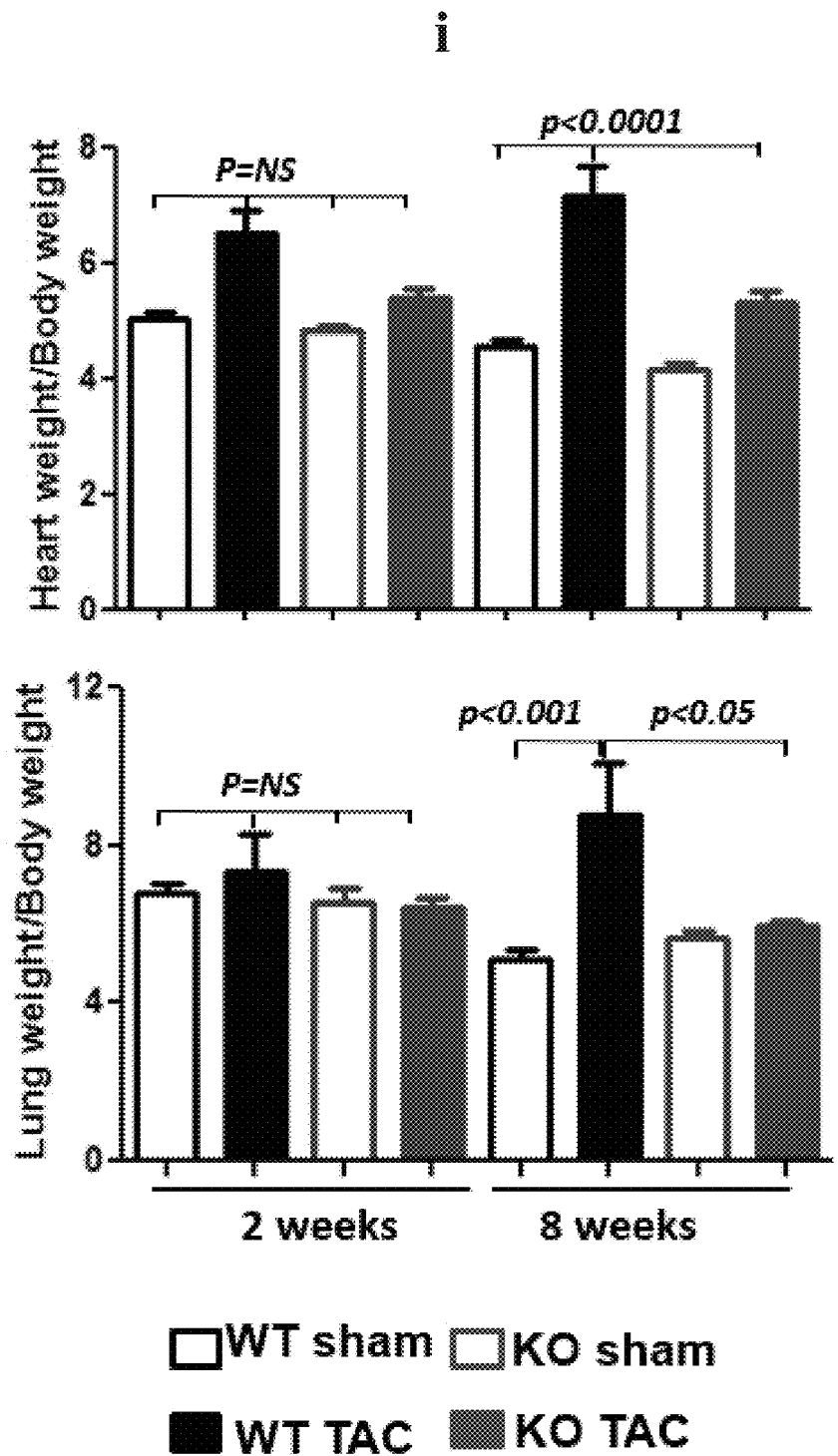
Figure 4:
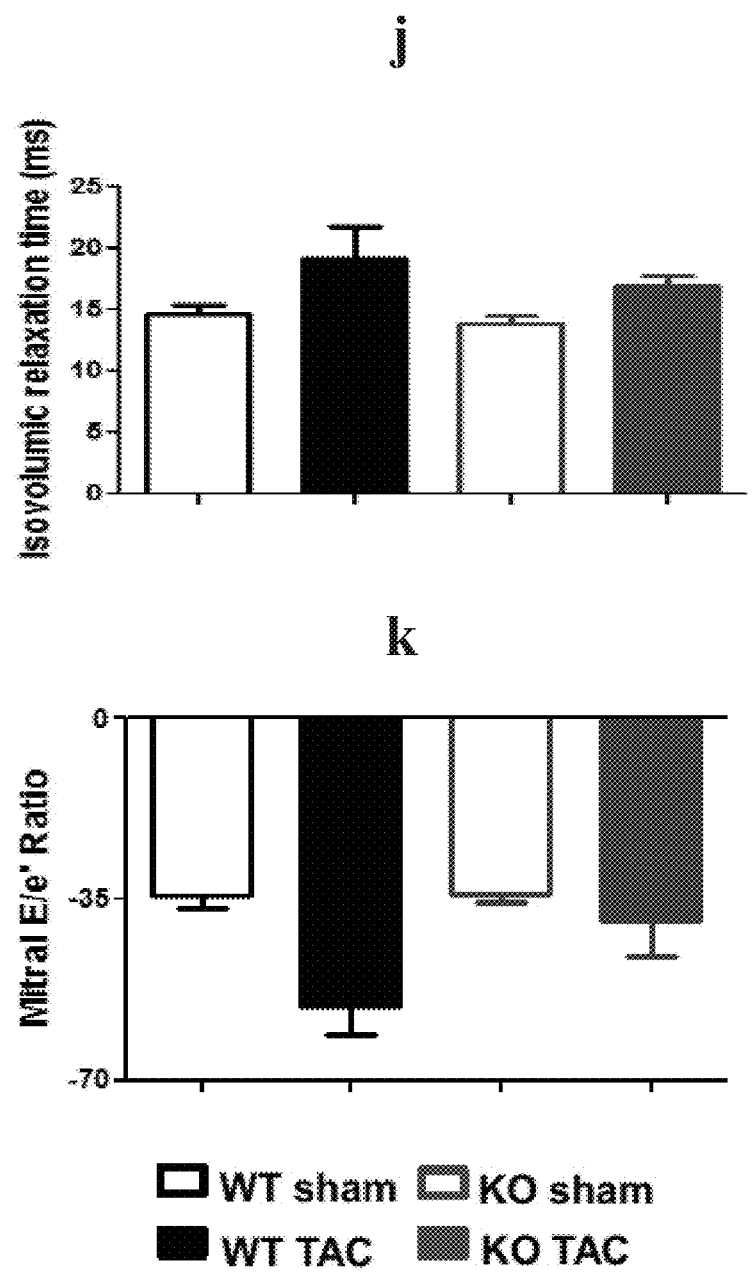
Figure 4:
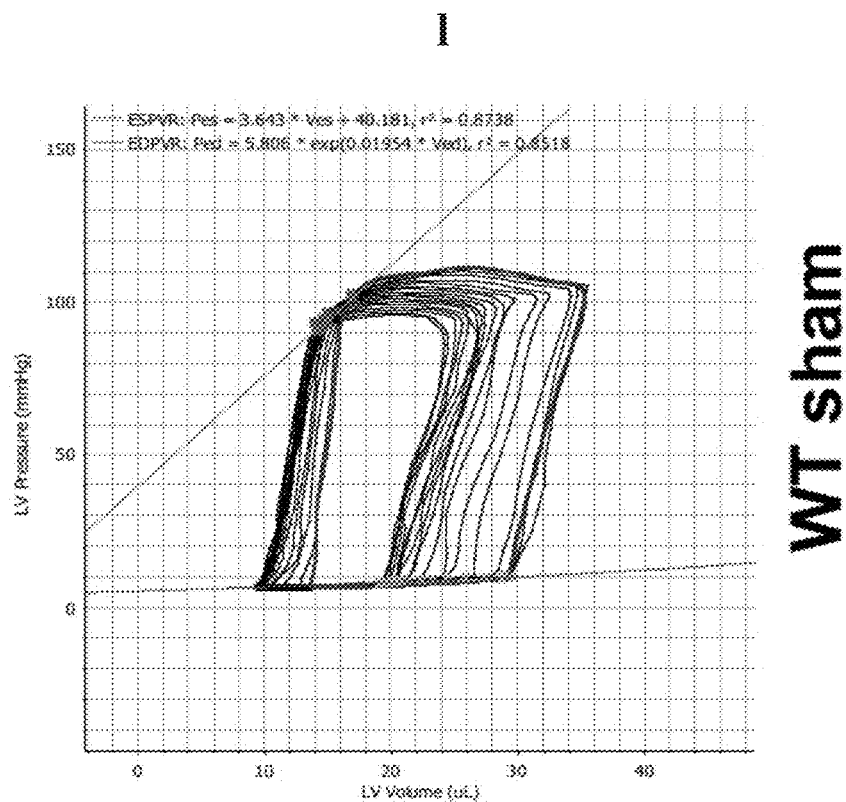
Figure 4:
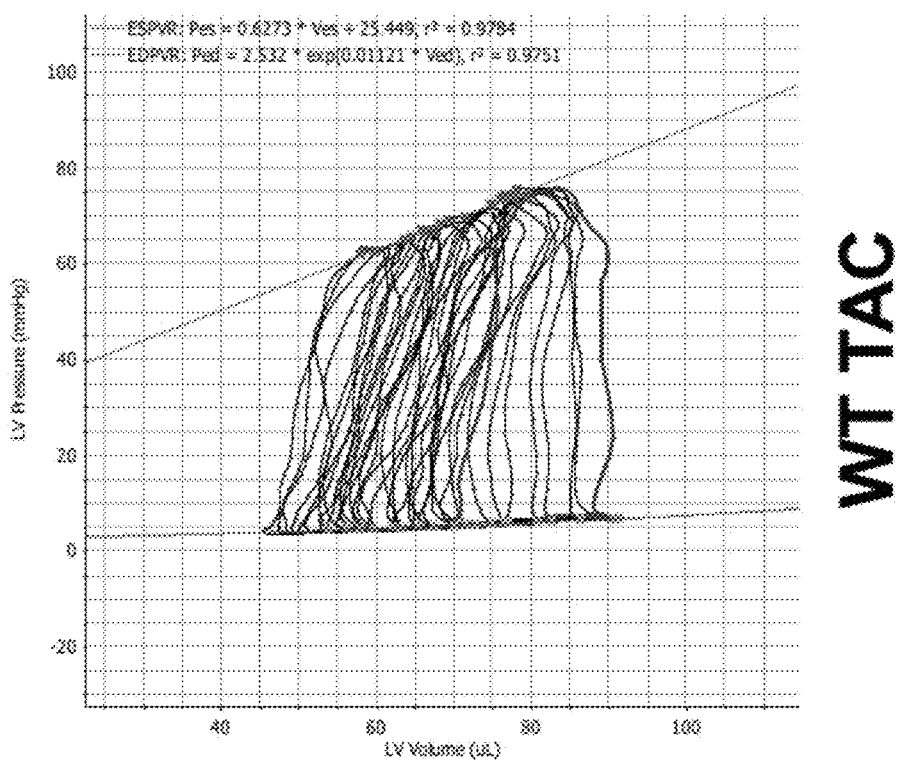
Figure 4:
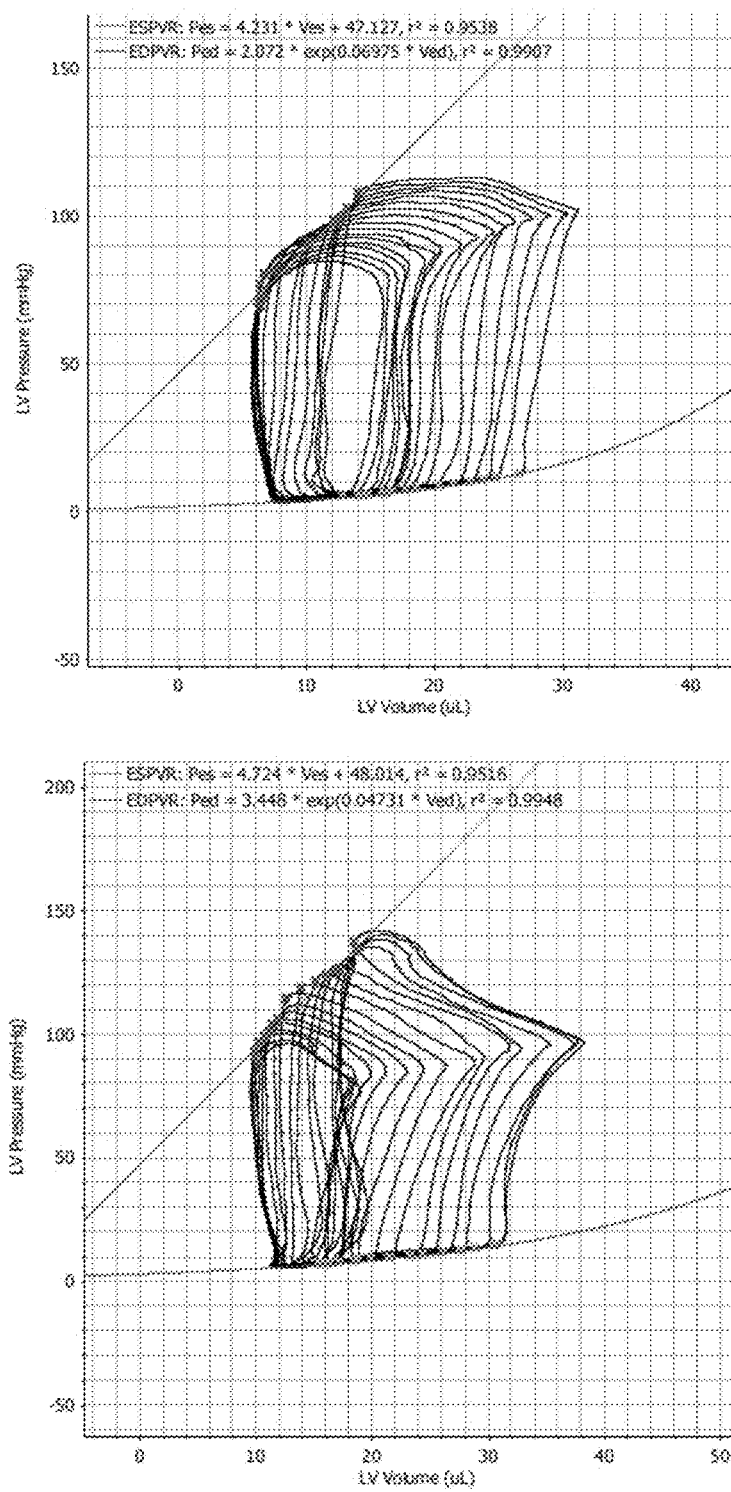
Figure 4:
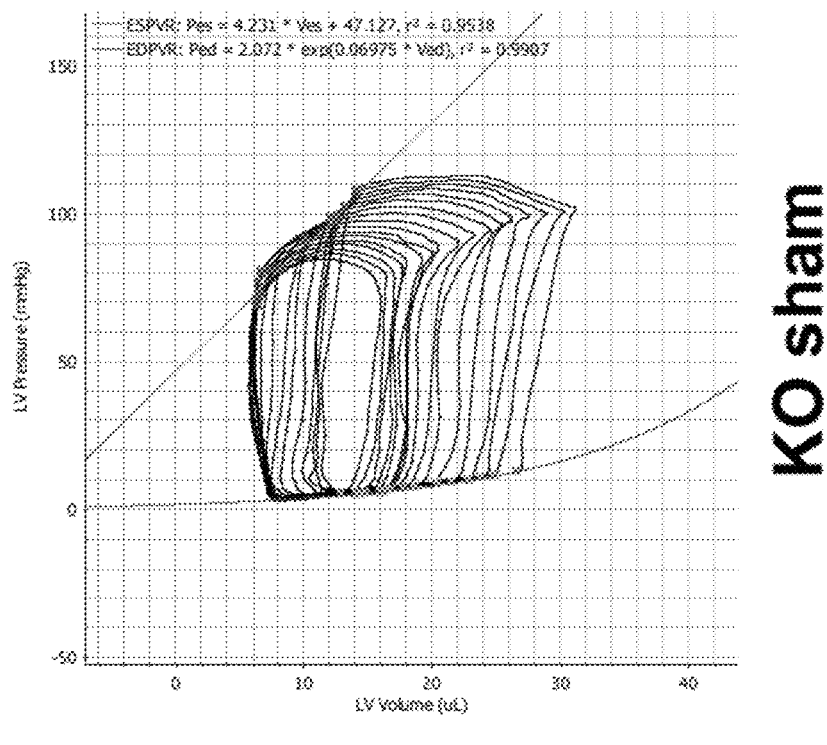
Figure 4:
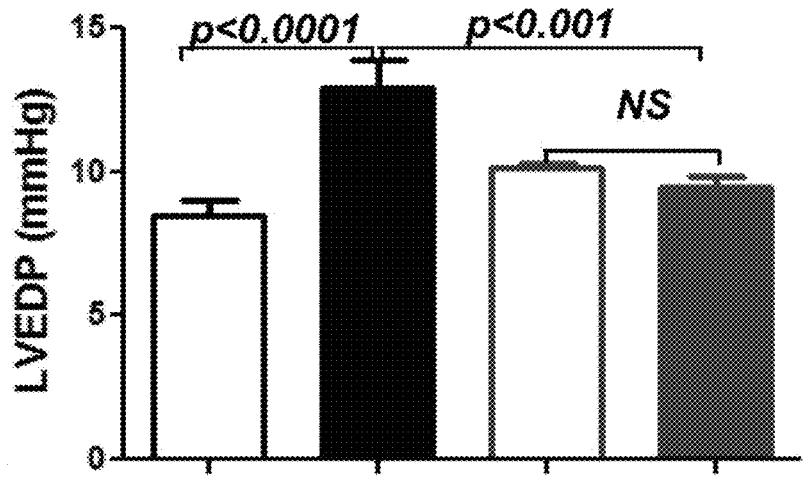
Figure 4:
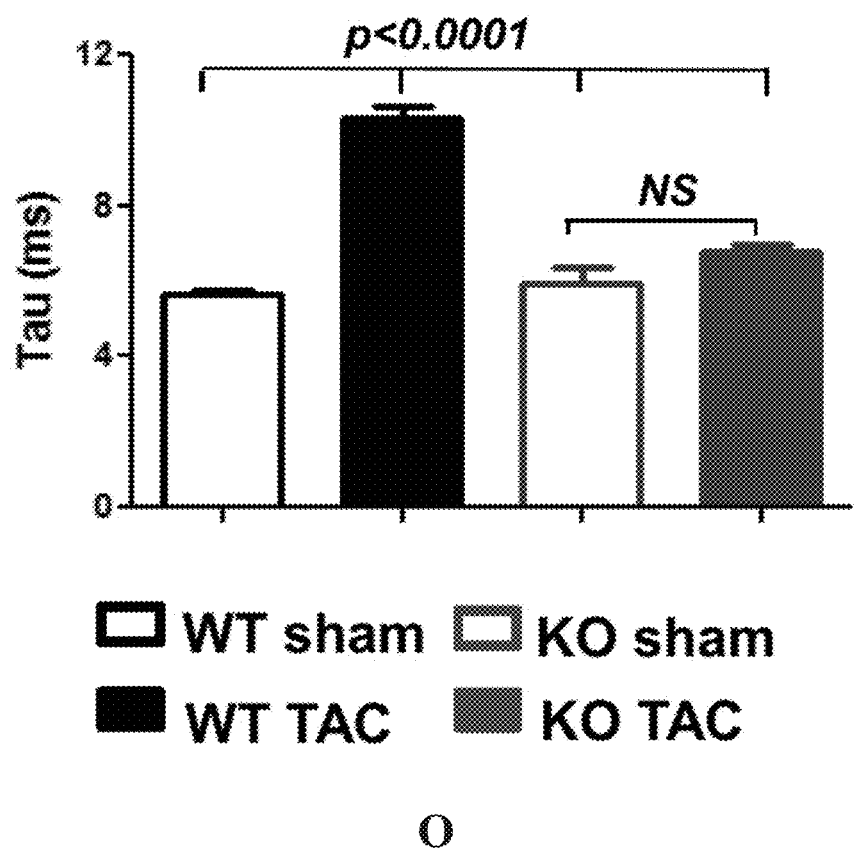

Indeed, in FIG. 4, IGFBP7$^{-/-}$ and WT mice were subjected to transaortic constriction (TAC) or sham surgery and analyzed 2-8 weeks after the operation. In FIG. 4(a), serial echocardiographic measurement of left ventricular (LV) fractional shortening (FS=(LVEDD-LVESD)/LVEDD× 100%); n=10-12 for each group; is provided. In FIG. 4(b), heart weight/tibia length ratios (HW/TL) at 8 weeks is shown. In FIG. 4(c), lung weight/tibia length ratios (LW/TL) at 8 weeks are shown. In FIG. 4(d), representative wheat germ agglutinin (WGA) staining of transverse heart (8 weeks) cross-sections showing myocyte cross sectional area (scale bars=200 μm) is shown. FIG. 4(e) provides quantitation. FIGS. 4(f)-(h) show RT-qPCR indicating that IGFBP7 deficiency abolished elevated fatal gene expression in TAC heart 2 weeks post surgery. Relative gene expression of (f) Nppb/Hprt1, (g) Nppa/Hprt1, and (h) Myh7/Myh6 ratio is shown as fold changes against WT sham group (n=3 per group).

One of the main characteristics of HEpEF is an increased LV diastolic stiffness. Next, the heart functions of WT and Igfbp$^{-/-}$ mice were assessed by serious echocardiography before surgery and at 2, 4, 6 and 8 weeks post-surgery. No cardiac physiological functional differences between WT and Igfbp7$^{-/-}$ mice at baseline (FIG. 4(a)) was observed. However, pressure overload induced by TAC triggers gradually declined heart muscular contractility in WT TAC mice, as measured by decreased Fractional Shortening (FS) % (FIG. 4a, Table 1). However, in Igfbp$^{-/-}$ TAC heart, there was only a moderate decrease in FS % at 2 weeks post TAC which maintained until 8 weeks post TAC when the experiments were terminated. More importantly, by 8 weeks post TAC, signs of LV diastolic dysfunction were also evidenced in WT TAC. Transmitral Doppler flow velocity showed a more rapid deceleration of the mitral E wave (FIG. 4(j)), suggesting an increase in LV chamber stiffness. (Schnelle M, et al. Echocardiographic evaluation of diastolic function in mouse models of heart disease. J Mol Cell Cardiol. 2017; 114:20-28) The ratio of mitral E velocity to mitral annular e' velocity (E/e'), a reliable predictor of LV end-diastolic pressure, (Methawasin M et al Circulation. 2016; 134:1085-1099) was elevated in WT TAC groups (FIG. 4(k)). The ratio of mitral E/A velocity was increased, also suggesting a restrictive LV filling pattern (FIG. 4(l)). Intriguingly, diastolic function of Igfbp$^{-/-}$ TAC heart remains normal. Invasive hemodynamics in-vivo pressure-volume measurements further demonstrated that Igfbp7 deficiency rescued TAC induced cardiac diastolic dysfunction as show by maintaining ESPVR (FIG. 4(l)), LVEDP and Tau at the similar level with sham operated control mice (FIG. 4(m)-4(n)). Parameters of LV systolic function measured by in-vivo pressure-volume further confirmed IGFBP7 deficiency also abolished TAC induced LV systolic dysfunction (Table 1, FIG. 4(o)). In summary, Igfbp7 deficiency not only abolished TAC induced LV systolic dysfunction but also maintained a normal LV diastolic Function in these studies. Igfbp7 deficiency protected mice from pressure overload induced heart failure.

TABLE 1

Tissue Morphometry, as well as Echocariographic and PV Analysis Parameters at 8 Weeks Post TAC and Sham Operation

| At 8 weeks post surgery | Igfbp7$^{+/+}$ sham | Igfbp7$^{+/+}$ TAC | Igfbp7$^{-/-}$ sham | Igfbp7$^{-/-}$ TAC |
|---|---|---|---|---|
| N (Tissue morphomertry) | 24 | 24 | 22 | 31 |
| heart weight, mg | 208 ± 3.97 | 290 ± 18.17** | 133 ± 3.93 | 161 ± 6.51 |
| Lung weight, mg | 232 ± 9.21 | 345 ± 39.19** | 181 ± 6.67 | 181 ± 3.48 |
| Body weight, g | 45.85 ± 1.04 | 41.38 ± 1.06 | 32.28 ± 1.08 | 30.81 ± 0.84 |

TABLE 1-continued

Tissue Morphometry, as well as Echocariographic and PV Analysis Parameters at 8 Weeks Post TAC and Sham Operation

| At 8 weeks post surgery | Igfbp7$^{+/+}$ sham | Igfbp7$^{+/+}$ TAC | Igfbp7$^{-/-}$ sham | Igfbp7$^{-/-}$ TAC |
|---|---|---|---|---|
| Tibia length, mm | 21 ± 0.24 | 21 ± 0.28 | 20 ± 0.15 | 20 ± 0.21 |
| HW/BW, mg/g | 4.58 ± 0.10 | 7.16 ± 0.52*** | 4.16 ± 0.13 | 5.31 ± 0.23 |
| LW/BW, mg/g | 5.12 ± 0.23 | 8.79 ± 1.27* | 5.64 ± 0.16 | 5.95 ± 0.15 |
| HW/TL, mg/mm | 9.78 ± 0.19 | 13.67 ± 0.93*** | 6.61 ± 0.21 | 7.93 ± 0.31 |
| LW/TL, mg/mm | 10.85 ± 0.37 | 16.33 ± 1.97** | 9.02 ± 0.34 | 8.89 ± 0.18 |
| N (echocardiography) | 6 | 7 | 6 | 9 |
| LVESD (mm) | 2.55 ± 0.04 | 3.95 ± 0.12** | 1.96 ± 0.06 | 2.16 ± 0.07 |
| LVEDD (mm) | 4.19 ± 0.0.06 | 5.21 ± 0.15** | 3.53 ± 0.08 | 3.58 ± 0.08 |
| FS (%) | 40.85 ± 1.05 | 27.88 ± 0.74*** | 44.37 ± 0.99 | 39.88 ± 0.96 |
| IVRT | 18.43 ± 4.39 | 29.13 ± 3.43 | 14.86 ± 1.16 | 17.75 ± 1.13 |
| IVCT | 14.58 ± 0.76 | 19.17 ± 2.66 | 13.87 ± 0.66 | 16.96 ± 0.86 |
| E/e' | −34.37 ± 2.44 | −55.72 ± 5.56 | −33.82 ± 1.95 | −39.22 ± 6.83 |
| N (invasive hemodynamics) | 6 | 7 | 6 | 9 |
| HR (bpm) | 606 ± 4.79 | 571 ± 6.01 | 580 ± 6.68 | 564 ± 3.09 |
| Arterial elastance (Ea) | 4.68 ± 0.08 | 3.64 ± 0.17* | 4.49 ± 0.20 | 4.84 ± 0.21 |
| dP/dt max (mmHg/sec) | 9676 ± 204 | 6511 ± 239*** | 9836 ± 624 | 7853 ± 166 |
| dP/dt min (mmHg/sec) | −8278 ± 217 | −5461 ± 247*** | −7863 ± 552 | −7637 ± 139 |
| EF (%) | 79.8 ± 1.98 | 67.56 ± 3.18*** | 81.80 ± 3.92 | 77.68 ± 1.69 |
| LVEDP (mmHg) | 9.69 ± 0.35 | 13.17 ± 0.79** | 9.57 ± 0.79 | 10.35 ± 0.38 |
| LVESP (mmHg) | 87.11 ± 1.64 | 97.72 ± 2.35** | 83 ± 9.57 | 105 ± 2.21 |
| Tau (Weiss' method) (ms) | 6.68 ± 0.33 | 9.64 ± 0.35*** | 6.06 ± 0.28 | 7.02 ± 0.11 |

N = number of mice per group;
Sham = Sham-operated;
TAC = transaortic constriction;
LVEDD = Left ventricular end-diastolic dimension;
LVESD = Left ventricular end-systolic dimension;
FS = LV Fractional Shortening;
IVRT = Isovolumic relaxation time;
IVCT = isovolumic contraction time;
E/e' = Ratio of the Doppler derived E to tissue Doppler derived E';
EF = ejection fraction; LVEDP = Left ventricular end-diastolic pressure;
LVESP = Left ventricular end-systolic pressure;
HR = heart rate;
See Table 1 for other abbreviations;
*P < 0.05,
**P < 0.01 and
***P < 0.001 comparing Igfbp7$^{-/-}$ TAC with Igfbp7$^{+/+}$ TAC.

Together, these experimental results indicate that IGFBP7 deficiency protects mice from pressure overload induced heart failure under the conditions tested.

Example 4: IGFBP7 Deficiency Attenuates Pressure Overload Induced Myocardial Fibrosis (Cardiac Fibrosis in TAC Mouse Heart)

This example indicates that under the conditions tested, IGFBP7 deficiency attenuates pressure overload induced cardiac fibrosis in TAC mouse heart. Experimental protocols are provided in the Methods section below, and results are provided in FIG. 5.

Myocardial fibrosis accumulation is another key pathophysiological feature of HEpEF. One of the most widely used methods to visualize fibrosis in histological tissue is Picrosirius red (PSR) staining (Cell Oncol 2011 34. 343-354). PRC staining of 8 weeks post TAC or sham heart cross-sections showed there is increased collagens deposition in WT TAC myocardium, and that knockout of Igfbp7 attenuated this increase (FIG. 5(a)). The structure and function of IGFBP7 share similarities with the CCN family of matricellular proteins, which plays important roles in cardiac matrix remodeling and fibrosis (Li J. et al. Emerging role of CCN family proteins in tumorigenesis and cancer metastasis (Review). Int J Mol Med. 2015 36:1451-63. & Li A H, Liu P P, Villarreal F J, Garcia R A. Dynamic changes in myocardial matrix and relevance to disease: Translational perspectives. Circulation Research. 2014; 114(5):916-27). The central mediator of this process is connective tissue growth factor (CTGF) which, when elevated, affects multiple signaling pathways and processes important in pathophysiology of myocardial fibrosis. Immunoblotting of heart tissue revealed increased CTGF protein expression in WT TAC heart 8 weeks post-surgery, and this increase is abolished by Igfbp7 deficiency (FIG. 5(b)). This is further confirmed in gene expression changes of ctgf and Tβ2, anther kye regulator of myocardial fibrosis (FIGS. 5c & 5d). IGFBP7 may thus have important matrix modulatory properties in concert with CTGF, which in turn contribute to cardiac fibrosis.

Figure 5:
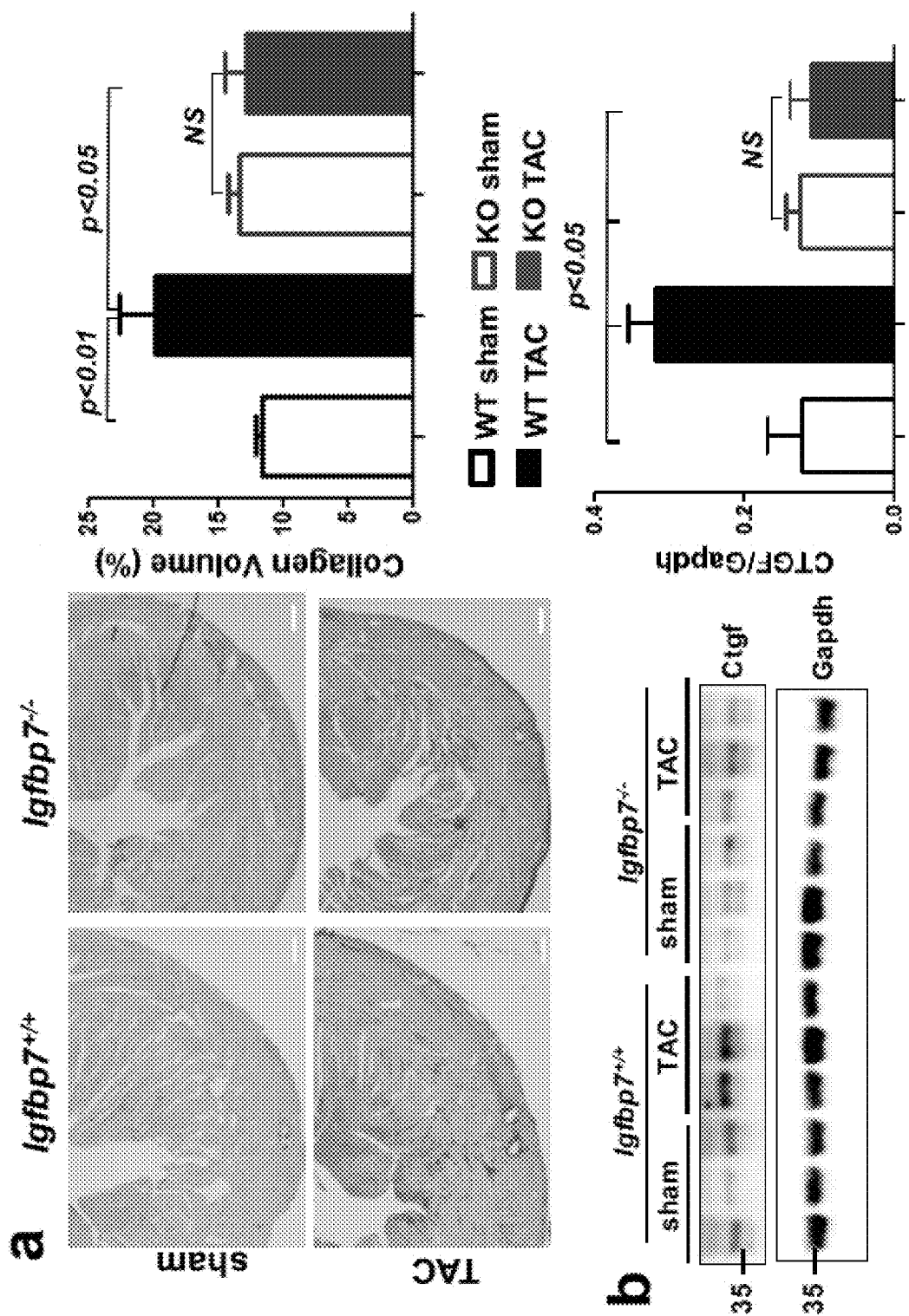
FIG. 5 shows that IGFBP7 deficiency attenuates pressure overload induced cardiac fibrosis in TAC mouse heart. IGFBP7$^{-/-}$ and WT mice were subjected to transaortic constriction (TAC) or sham surgery and analyzed 8 weeks after the operation. (a) Representative Picrosirius Red staining for collagen of transverse heart cross-sections and quantization showing increased collagen deposition in WT TAC heart, which is much attenuated by IGFBP7 deficiency. Scale bars=1 mm. (b) immunoblotting and quantification for connective tissue growth factor (CTGF) in heart extracts (n=3 per group), GAPDH were used as loading control. (c) & (d) RT-qPCR further confirmed Igfbp7 deficiency abolished elevated ctgf and tgfβ2 gene expression in TAC heart 2 weeks post-surgery. In all panels, error bars represent s.e.m., one way ANOVA was used to calculate P values.
Figure 5:
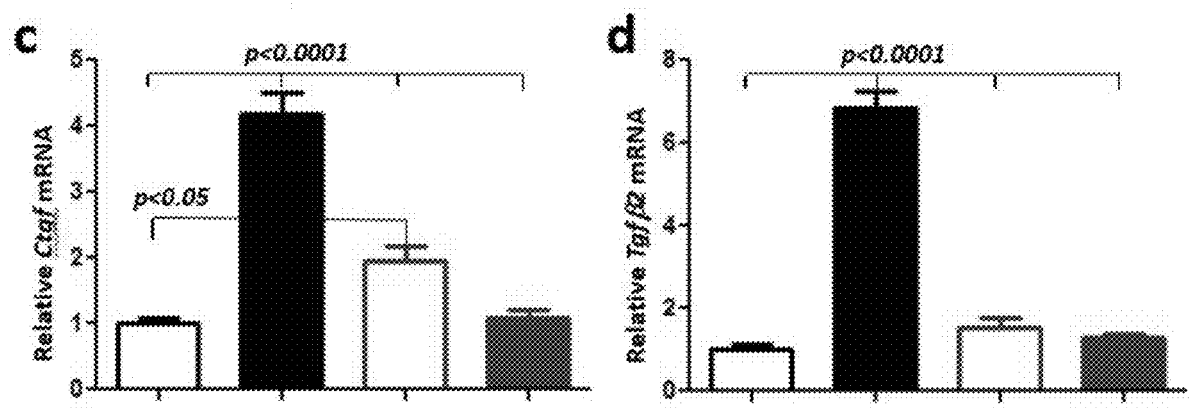

Indeed, in FIG. 5, IGFBP7$^{-/-}$ and WT mice were subjected to transaortic constriction (TAC) or sham surgery and analyzed 8 weeks after the operation. FIG. 5(a) shows representative Picrosirius Red staining for collagen of transverse heart cross-sections and quantization showing increased collagen deposition in WT TAC heart, which is much attenuated by IGFBP7 deficiency. FIG. 5(b) shows immunoblotting and quantification for connective tissue growth factor (CTGF) in heart extracts, revealing increased CTGF protein expression in WT TAC heart 8 weeks post-surgery, and this increase is abolished by Igfbp7 deficiency. FIGS. 5(c) & 5(d) show qRT-PCR quantisation of ctgf and Tgfβ2 gene expression in heart extracts.

Together, these experimental results indicate that IGFBP7 deficiency attenuates pressure overload induced cardiac fibrosis in TAC mouse heart under the conditions tested.

Figure 6:
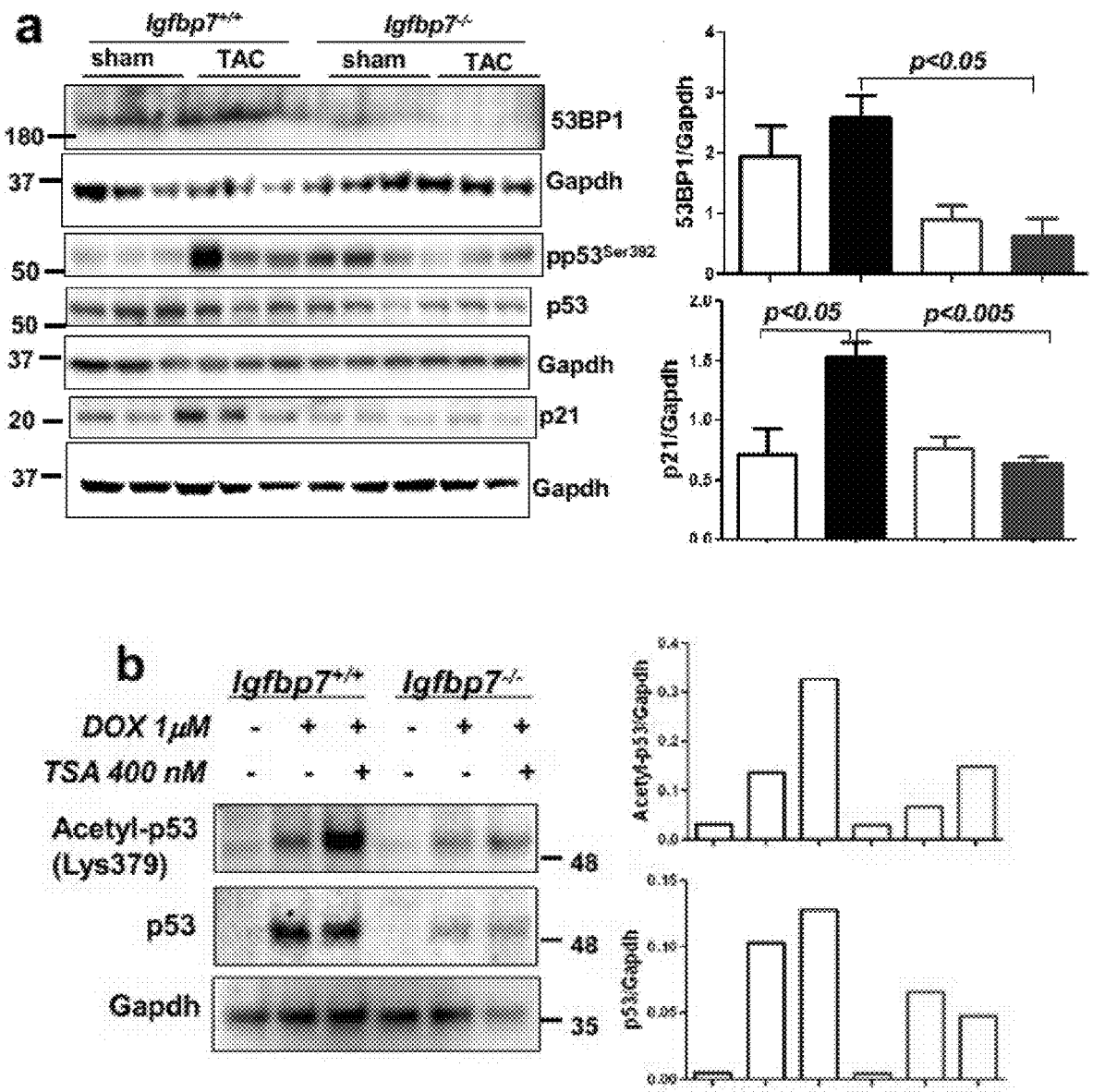
FIG. 6 shows IGFBP7 plays an important role in stress induced cellular senescence in mouse myocardium. (a) IGFBP7$^{-/-}$ and WT mice were subjected to transaortic constriction (TAC) or sham surgery and analyzed 8 weeks after the operation. Representative immunoblotting and quantification for cellular senescence markers 53BP1, phosphor (pp53$^{ser392}$) and total p53, and p21 in heart extracts (n=3 per group), GAPDH were used as loading control. In all panels, error bars represent s.e.m., one way ANOVA was used to calculate P values. (b) and (c) show IGFBP7$^{-/-}$ and WT neonatal cardiomyocyte (NCM) isolated from new born pups and subjected to Doxorubicin (DOX) treatment to induce cellular senescence. (b) shows representative immunoblotting for the cellular senescence markers acetylated p53 (Acetl-p53) and total p53 in Dox (1 μM) or Dox (1 μM)+Trichostatin A (TSA) (400 nM) treated NCM for 3 days. Solvent treated cells were use as control (NT), GAPDH was used as loading control. (c) shows representative microscopy images of Cellular Senescence Assay staining of IGFBP7$^{-/-}$ and WT NCM treated with Dox (1 μM) for 7 days, showing increased SA-β-gal positive senescent cells (blue) in WT but not in IGFBP7$^{-/-}$ NCM (Bar=200 μm for top panels and 20 μm for bottom panels). (d) RT-qPCR reveals IGFBP7 deficiency abolished elevated Trp53 expression in TAC heart 2 weeks post-surgery. Relative Trp53/Hprt1 expression was shown as fold change against WT sham group, n=3 per group. (e) and (f) Measuring of cytokine level in blood samples of TAC mice by Elisa, indicated IGFBP7 deficiency blocked TAC triggered elevated IL-6 in plasmas samples, n=3, per group. In all panels error bars represent s.e.m., one way ANOVA were used to calculate P values. (g) RT-qPCR reveals Igfbp7 deficiency abolished elevated Cdkn1a expression in TAC heart 2 weeks post-surgery. Relative Cdkn1a/Hprt1 expression was shown as fold change again WT sham group, n=3 per group.
Figure 6:
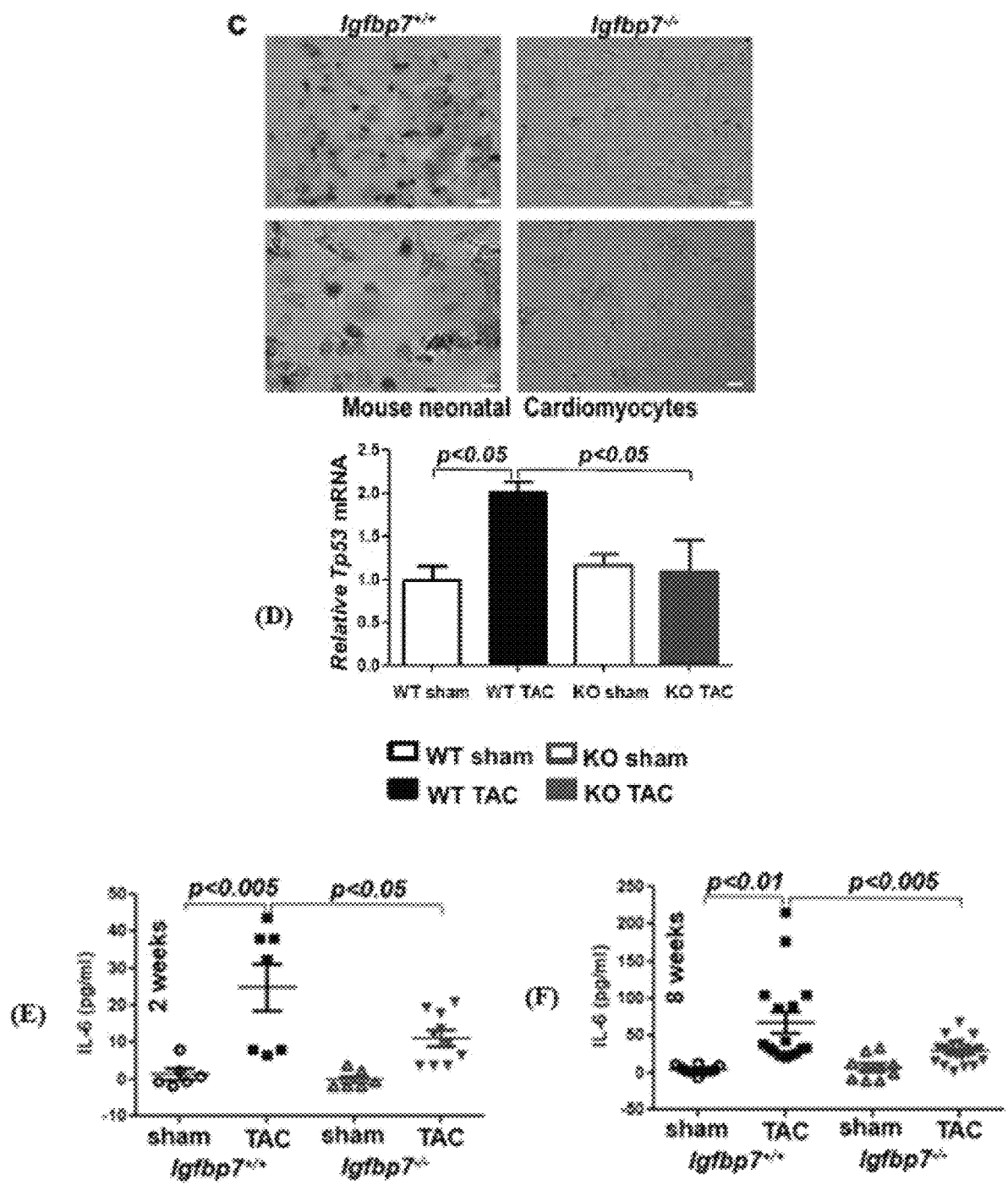
Figure 6:
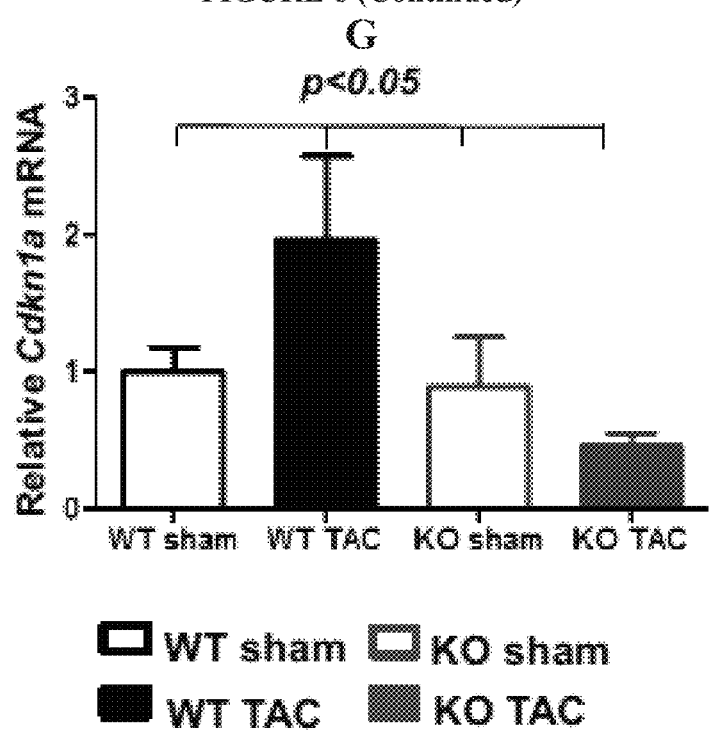

Example 5: IGFBP7 Plays an Important Role in Stress Induced Cellular Senescence in Mouse Myocardium—IGFBP7 Deficiency Protects Myocardium from Stress Induced Cellular Senescence This example indicates that under the conditions tested, IGFBP7 plays an important role in stress induced cellular senescence in mouse myocardium. Experimental protocols are provided in the Methods section below, and results are provided in FIG. 6.

Heart failure with preserved ejection fraction typically is associated with oxidative stress, inflammation and accelerated cardiovascular aging (Ouzounian M, Lee D S, Liu P P. Diastolic heart failure: mechanisms and controversies. Nature Clin Pract Cardiovasc Med. July 2008; 5(7):375-86. & Wood P, Piran S, Liu P P. Diastolic heart failure: progress, treatment challenges, and prevention. Can J Cardiol. May-June 2011; 27(3):302-10). IGFBP7 is part of the stress-senescence pathway, and is a member of the senescence associated secretory phenotype proteome or secretome (SASP) (Campisi J. Aging, cellular senescence, and cancer. Annu Rev Physiol. 2013; 75:685-705). Multiple stresses such as DNA damage, oxidative stress, oncogenic activation (e.g Erk, p53) or innate immunity/inflammasome formation trigger cellular senescence. To test if lack of Igfbp7 will protect myocardium from pressure overload induced cellular senescence, protein levels of several well established senescence markers were measured by immunoblotting in WT and Igfbp7$^{-/-}$ heart tissue 8 weeks post TAC or sham operation. As shown in FIG. 6a, elevated 53BP1, phosphor-p53, total p53 and p21 were detected in WT TAC heart, but not in Igfbp7$^{-/-}$ heart. This was further confirmed in mRNA level of Tp53 and Cdkn1a when measured by q-RT-PCR (FIGS. 6d and g). Doxorubicin (Dox), a chemotherapy drug, induces premature senescence mediated cardiotoxicity. When neonatal cardiomyocytes (NCM) isolated from both WT and Igfbp7$^{-/-}$ mice were exposed to Dox treatment, both elevated p53 acetylation, and total p53, hallmarks of cellular senescence (Tonnessen-Murray C A, Lozano G, Jackson J G. The Regulation of Cellular Functions by the p53 Protein: Cellular Senescence. Cold Spring Harb Perspect Med. 2017; 7(2). & Johmura Y, Nakanishi M. Multiple facets of p53 in senescence induction and maintenance. Cancer Sci. 2016; 107:1550-1555), were detected in WT NCM, but not in Igfbp7$^{-/-}$ NCM (FIG. 6b). Further, when subjecting NCM to senescence associated β-galactosidase staining, significantly increased β-galactosidase positive cells were found in WT NCM treated with Dox compared to Igfbp7$^{-/-}$ NCM with same treatment (FIG. 6c). Increased secretion of interleukins such as IL-6 to peripheral blood is another indicator of accelerated cellular senescence in stressed myocardium (Kuilman T, et al. Oncogene-induced senescence relayed by an interleukin-dependent inflammatory network. Cell. 2008; 133:1019-31). IL-6 ELISA assay confirmed there is significantly increased IL-6 in plasma samples of WT TAC mice compared with Igfbp7$^{-/-}$ mice plasma (FIG. 6e-6f). All the above indicated IGFBP7, when persistently elevated, promoted accelerated myocyte senescence. Based on these results, inhibition of IGFBP7 may therefore be indicated for treatment of age related heart failure.

Indeed, in FIG. 6(a), IGFBP7$^{-/-}$ and WT mice were subjected to transaortic constriction (TAC) or sham surgery and analyzed 8 weeks after the operation. Representative immunoblotting and quantification for cellular senescence markers 53BP1 and p21 in heart extracts are provided. In FIGS. 6(b) and 6(c), IGFBP7$^{-/-}$ and WT neonatal cardiomyocytes (NCM) were isolated from new born pups and subjected to Doxorubicin (DOX) treatment to induce cellular senescence. FIG. 6(b) shows representative immunoblotting for the cellular senescence markers acetylated p53 (Acetl-p53) and total p53 in Dox (1 µM) or Dox (1 µM)+ Trichostatin A (TSA) (400 nM) treated NCM for 3 days. Solvent treated cells were used as control (NT). FIG. 6(c) shows representative microscopy images of Cellular Senescence Assay staining of IGFBP7$^{-/-}$ and WT NCM treated with Dox (1 µM) for 7 days, showing increased SA-β-gal positive senescent cells (blue) in WT but not in IGFBP7$^{-/-}$ NCM. In FIG. 6(d), RT-qPCR indicates that IGFBP7 deficiency abolished elevated Trp53 expression in TAC heart 2 weeks post-surgery. Relative Trp53/Hprt1 expression is shown as fold change against WT sham group. In FIGS. 6(e) and (f), measurement of cytokine levels in blood samples of TAC mice using ELISA indicated that IGFBP7 deficiency blocked TAC triggered elevated IL-6 in plasma samples.

Together, these experimental results indicate that IGFBP7 plays an important role in stress induced cellular senescence in mouse myocardium under the conditions tested.

Example 6: IGFBP7 Regulates Cardiac Remodeling by Modulating IGF-1 Signaling—IGFBP7 Deficiency Partially Blocked IGF-1/Insulin Receptor-Dependent Signaling, Resulting in Blunted Cardiac Hypertrophy in IGFBP7$^{-/-}$ TAC Hearts This example indicates that under the conditions tested, IGFBP7 deficiency partially blocked IGF-1/insulin receptor-dependent signaling, resulting in blunted cardiac hypertrophy in IGFBP7$^{-/-}$ TAC hearts. Experimental protocols are provided in the Methods section below, and results are provided in FIG. 7.

All members of insulin-like growth factor binding proteins share the IGFBP motif, are capable of binding to insulin-like growth factor, and modulate their availability and function. IGF-1, IGF-2 and Insulin are potent growth factors that activate AKT signaling through IGF-1 receptors (IGF-1R). IGFBP7 can significantly influence IGF/insulin signaling dynamics at high concentrations, and can also influence IGF/insulin signaling intracellularly (Nawathe A R, et al. Insulin-like growth factor axis in pregnancies affected by fetal growth disorders. Clin Epigenetics. 2016 Jan. 27; 8:11). To explore if Igfbp controls cardiac remodeling by regulation of IGF-1 signaling, first, Igf-1 protein levels in both heart and plasma samples from WT and Igfbp7$^{-/-}$ mice were measured by ELISA. Igfbp7 deficiency significantly lowered Igf-1 protein levels in both heart tissue and in plasma (FIG. 7c). As indicated, Igfbp7 is important for maintaining Igf-1 levels. More importantly, Igfbp7 deficiency suppressed the whole IGF-1 receptor/Insulin receptor signaling pathway, from decreased IGF-1R and Insulin receptor phosphorylation (FIG. 7d-e), to reduced phosphorylation of Insulin receptor substrate (IRS-1) (FIG. 7f-g). Furthermore downstream of IGF1-R and IRS-1, Akt signaling, a key regulator of cardiac hypertrophy, was also suppressed by Igfbp7 deficiency as illustrated by immonoblotting of TAC and sham heart 8 weeks post-surgery (FIG. 7h-i). Activation of Erk1/2, another key regulator of cardiac hypertrophic/senescence pathway downstream of IGF-1R/IRS-1, was also down regulated (FIG. 7c).

Figure 7:
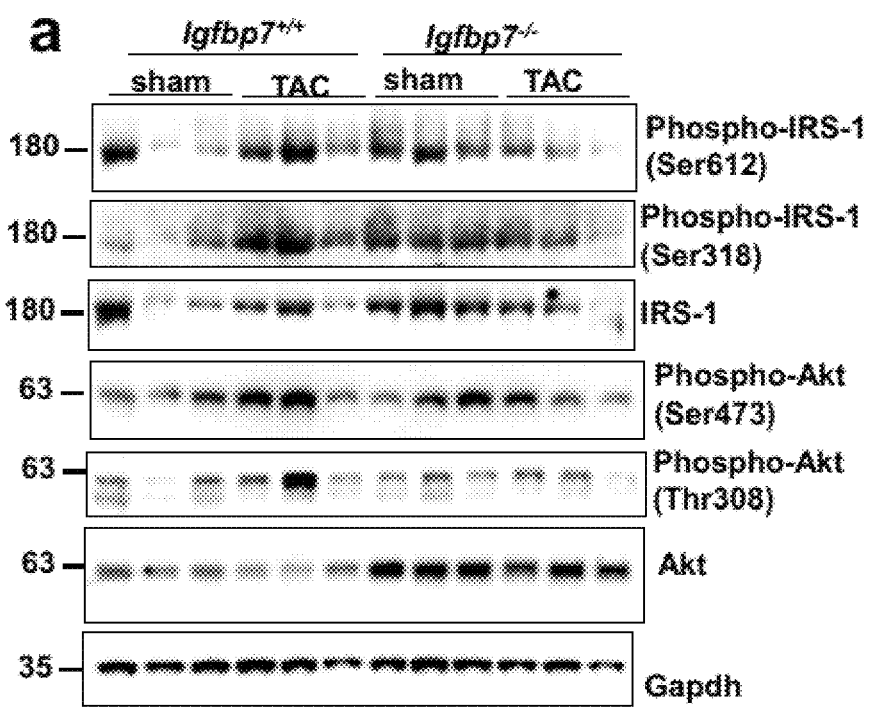
FIG. 7 shows that IGFBP7 deficiency partially blocked IGF-1/Insulin receptor-dependent signaling, resulting in blunted cardiac hypertrophy in IGFBP7$^{-/-}$ TAC hearts. IGFBP7 is indicated as regulating cardiac remodeling by modulating IGF-1 signaling. IGFBP7$^{-/-}$ and WT mice were subjected to transaortic constriction (TAC) or sham surgery and analyzed 8 weeks after the operation. Representative immunoblotting and quantification for (a) activation of insulin receptor substrate (IRS-1), shown by the ratio of phosphor-IRS-1 to total IRS-1; and its downstream activation of Akt, shown by the ratio of phospho-Akt to total Akt, were all down regulated in IGFBP7$^{-/-}$ TAC hearts; (b) activation of p44/42 MAPK, another major IGF-1/Insulin receptor-dependent pathway was also down regulated in IGFBP7$^{-/-}$ TAC hearts, as shown by the ratio of phosphor-p44/42 MAPK to total p44/42 MAPK in heart extracts (n=2-3 per group), GAPDH were used as loading control. In all panels error bars represent s.e.m., one way ANOVA was used to calculate P values. (c) Measuring of Igf-1 level in heart lysates and blood samples of TAC mice by ELIZA, indicated Igfbp7 deficiency reduces Igf-1 levels in both heart and plasmas samples, n=3, per group. (d-i) Representative immunoblotting and quantification for activation of IGF-1 receptor and insulin receptor (d-e), insulin receptor substrate (IRS-1), shown by the ratio of phosphor-IRS-1 to total IRS-1 (f-g); and its downstream activation of Akt, shown by the ratio of phospho-Akt to total Akt (h-i) were all down regulated in Igfbp7$^{-/-}$ TAC hearts.
Figure 7:
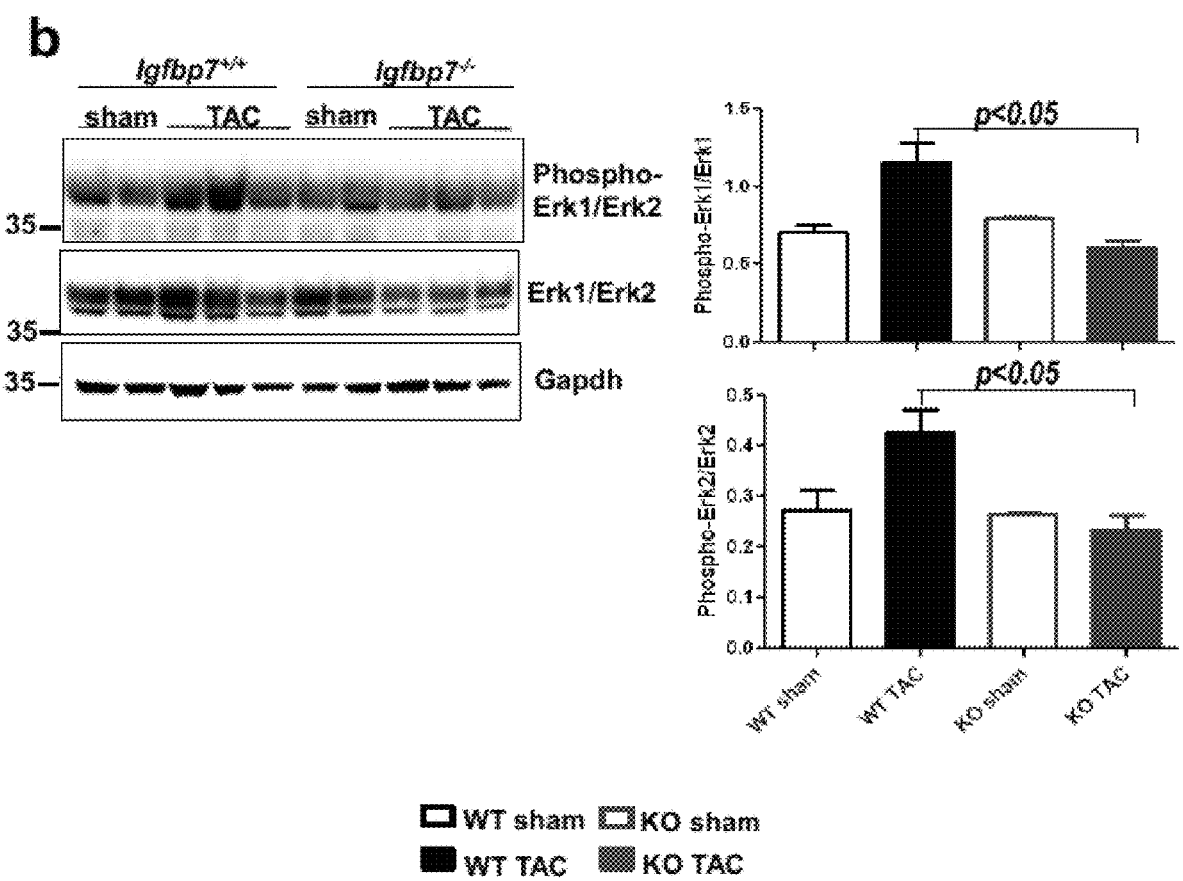
Figure 7:
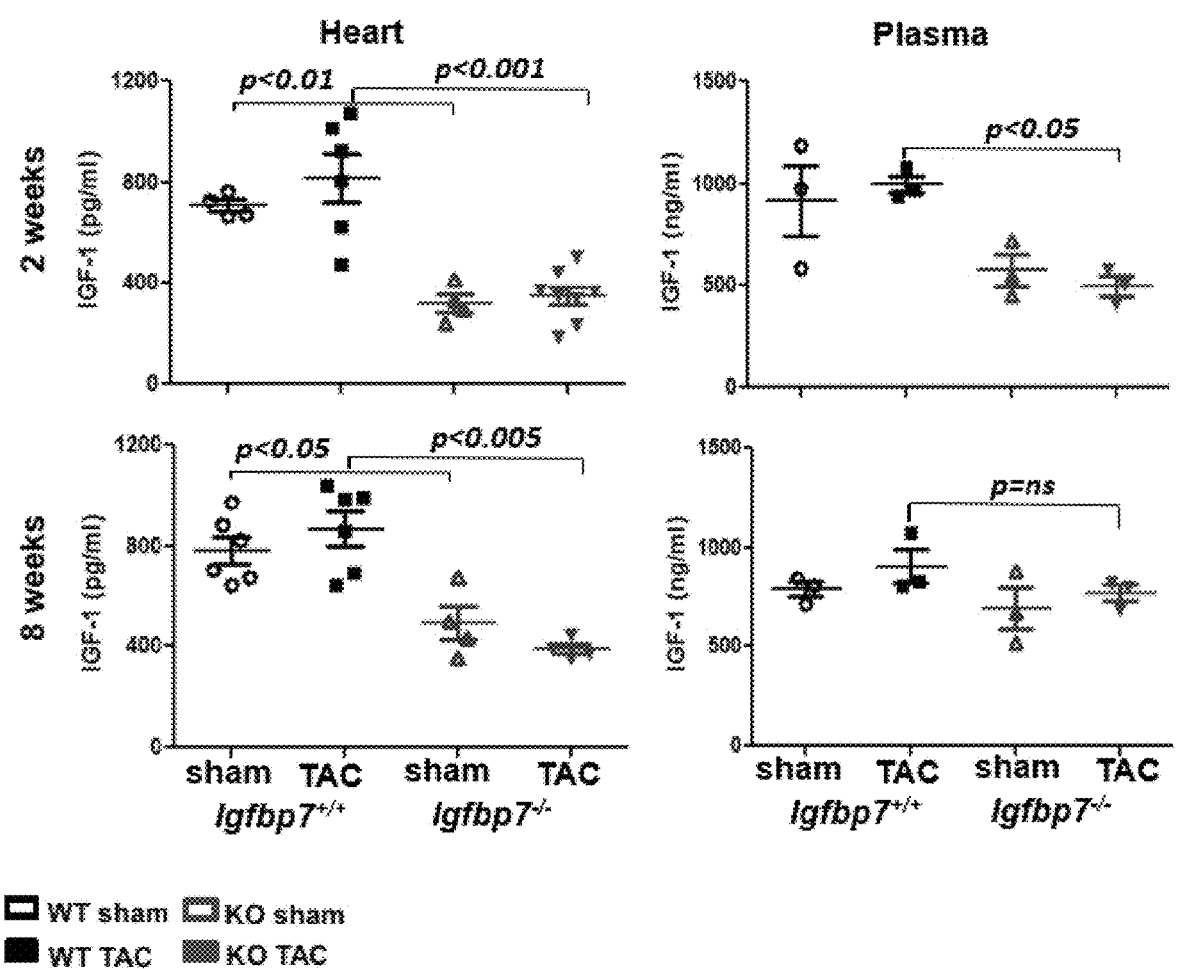
Figure 7:
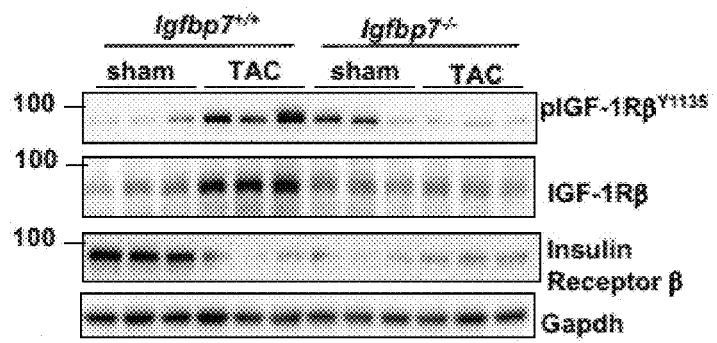
Figure 7:
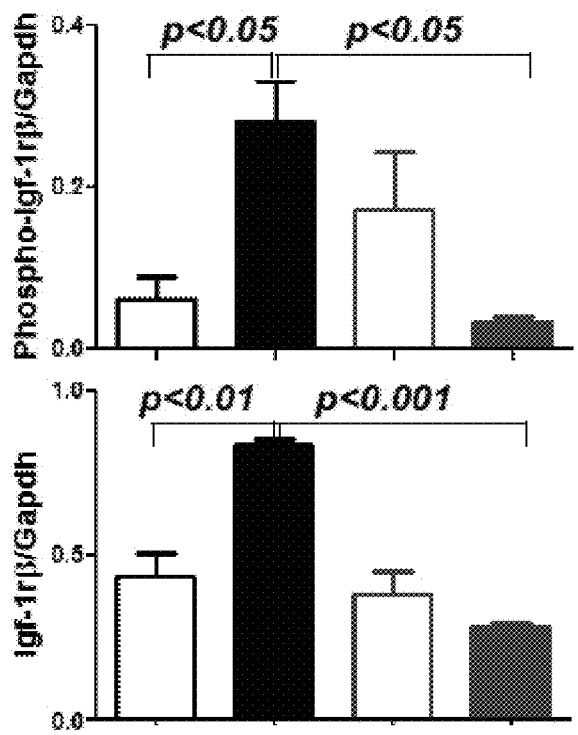
Figure 7:
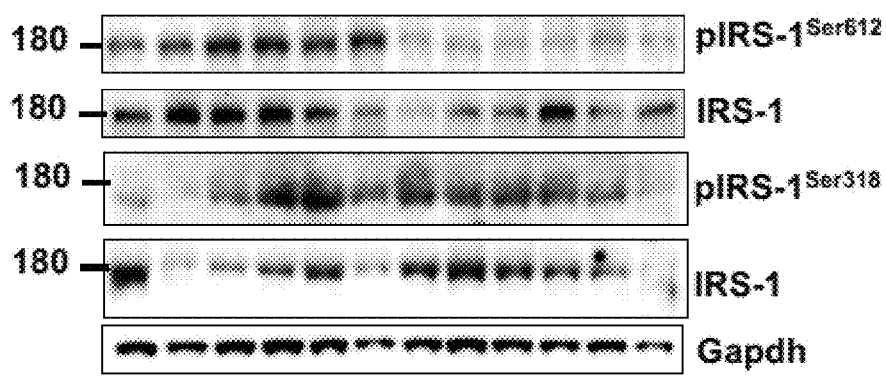
Figure 7:
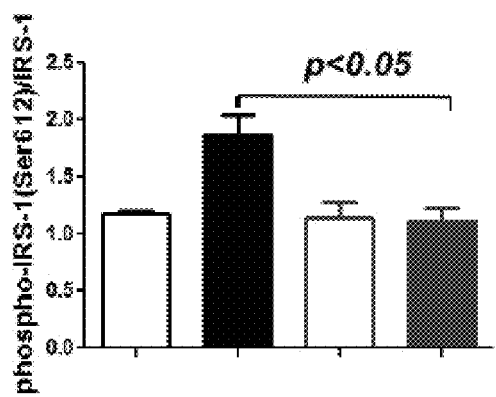
Figure 7:
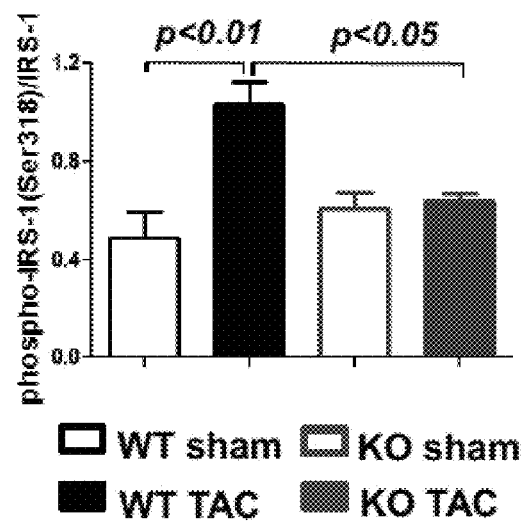
Figure 7:
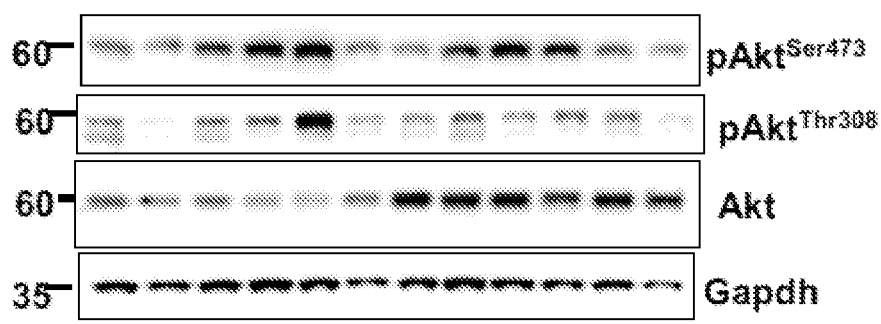
Figure 7:
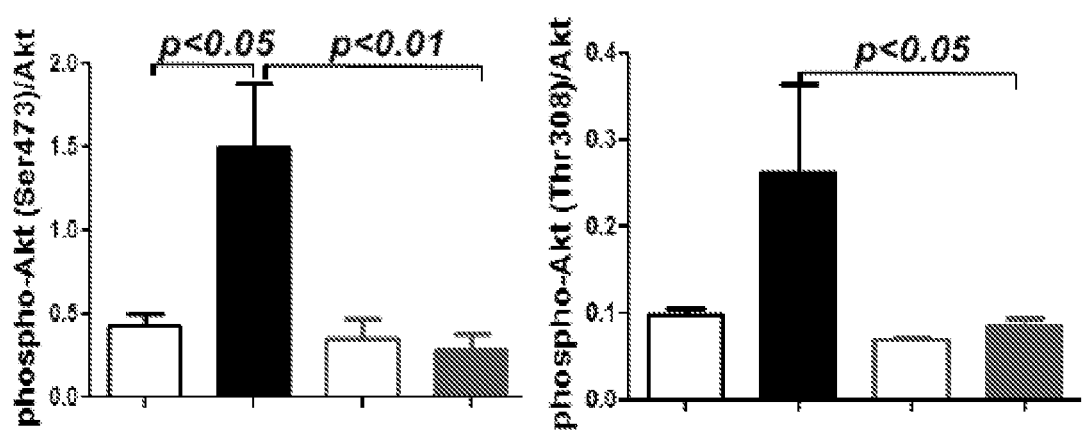

Indeed, in FIG. 7, IGFBP7$^{-/-}$ and WT mice were subjected to transaortic constriction (TAC) or sham surgery and analyzed 8 weeks after the operation. Representative immunoblotting and quantification for activation of insulin receptor substrate (IRS-1), shown by the ratio of phosphor-IRS-1 to total IRS-1; and its downstream activation of Akt, shown by the ratio of phospho-Akt to total Akt, were all down regulated in IGFBP7$^{-/-}$ TAC hearts as shown in FIG. 7(a); and activation of p44/42 MAPK, another major IGF-1/Insulin receptor-dependent pathway, was also down regulated in IGFBP7$^{-/-}$ TAC hearts, as shown by the ratio of phosphor-p44/42 MAPK to total p44/42 MAPK in heart extracts, as shown in FIG. 7(b).

Together, these experimental results indicate that IGFBP7 deficiency partially blocked IGF-1/insulin receptor-dependent signaling, resulting in blunted cardiac hypertrophy in IGFBP7$^{-/-}$ TAC hearts under the conditions tested.

Example 7: IGFBP7 Knockdown Blocked Hypertrophic and Cellular Senescence Signaling in Human Cardiac Myocytes This example indicates that under the conditions tested, IGFBP7 knockdown blocked hypertrophic and cellular senescence signaling in human cardiac myocytes. Experimental protocols are provided in the Methods section below, and further described as follows.

Results described hereinabove obtained from an in vivo TAC model shown Igfbp7 deficiency protects mice from pressure overload induced heart failure. To investigate inhibition of IGFBP7 expression as a therapeutic treatment for heart failure, a few IGFBP7 small interfering RNA (siRNA) were selected and tested their knockdown efficiency with human cardiac myocyte (HCM) culture. Two of the IGFBP7 siRNA oligos tested shown efficient knockdown of IGFBP7 gene expression as measured by q-RT-PCR (FIG. 8a). Angiotensin II (Ang II) is known to induce myocardium hypertrophy and premature senescence (Circulation 2006; 114:953-960). To verify if siRNA knockdown of IGFBP7 in HCM will block Ang II induced hypertrophy and senescence, again, q-RT-PCR was used to assay selected hypertrophic and senescence marker gene expression. As shown in FIG. 8b-d, Ang II treatment triggered significantly induction in nppb (BNP), Tp53 (p53) and Cdkn1a (p21) gene expression. Knockdown of IGFBP7 by siRNA abolished this increase. Moreover, β-galactosidase staining revealed IGFBP7 knockdown blocked DOX induce cellular senescence, as shown by reduced β-galactosidase positive cells in IGFBP7 siRNA treated HCM compared with control siRNA treated HCM (FIG. 8e). The above results suggest that IGFBP7 inhibitors, such as siRNA knockdown of IGFBP7 for example, may provide for therapeutic treatment of heart failure such as HEpEF.

Indeed, in this example, Human Cardiac Myocytes (HCM) obtained from PromoCell (Heidelberg, Germany; c-12810) were seeded in a 6 well plate containing myocyte growth medium (PromoCell C-22070), at a density of 10,000 cells per cm$^2$, in a humidity controlled incubator at 37° C., 5% CO$_2$ for about 24 hours until cells reached about 70% confluence before starting siRNA treatment. Knockdown of IGFBP7 in HCM were achieved using two silencer select pre-designed siRNAs specific to human IGFBP7 (Thermo Fisher Scientific (Waltham, Mass.), siRNA ID s7239, UGGUAUCUCCUCUAAGUAAtt (SEQ ID NO: 9, siRNA 1) and siRNA ID s7240, CGAGCAAGGUCCUUC-CAUAtt (SEQ ID NO: 10, siRNA 2)), which were used to knockdown IGFBP7 expression in HCM.

The sense strand sequences of these siRNAs are shown below and in FIG. 1F as SEQ ID NO: 9 and SEQ ID NO: 10 as follows:

```
siRNA ID s7239:         UGGUAUCUCCUCUAAGUAAtt
(SEQ ID NO: 9; siRNA 1; sense strand; uppercase =
RNA, lower case = DNA);
and siRNA ID s7240:         CGAGCAAGGUCCUUCCAUAtt
(SEQ ID NO: 10; siRNA 2; sense strand; uppercase =
RNA, lower case = DNA).
```

The antisense strand sequences of these siRNAs are shown below and in FIG. 1G as SEQ ID NO: 11 and SEQ ID NO: 12 as follows:

```
(siRNA 1 antisense strand, uppercase = RNA, lower
case = DNA)
                                        SEQ ID NO: 11
UUACUUAGAGGAGAUACCAgc (siRNA 2 antisense strand, uppercase = RNA, lower
case = DNA)
                                        SEQ ID NO: 12
UAUGGAAGGACCUUGCUCGca
```

Figure 8:
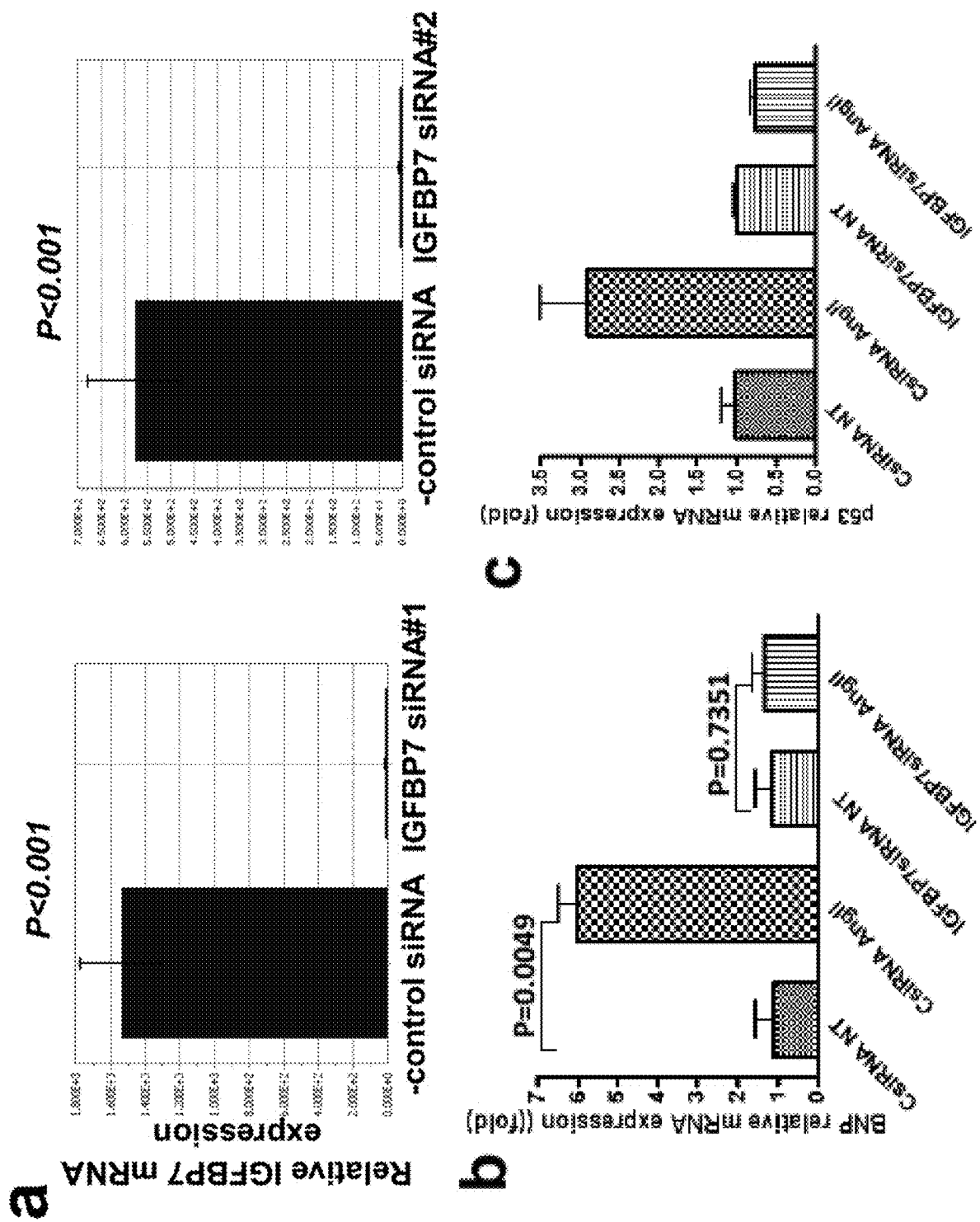
FIG. 8 shows that IGFBP7 knockdown blocked hypertrophic and cellular senescence signaling in human cardiac myocytes. Human cardiac myocytes obtained from Promo-Cell were treated with negative control siRNA and IGFBP7 siRNA. (a) Knockdown efficiency of two IGFBP7 siRNA oligos was checked 48 h post siRNA treatment by RT-qPCR with two IGFBP7 specific primer pairs. HTRP1 expression was used as control. IGFBP7 siRNA resulted in hundreds fold decrease in IGFBP7 gene expression shown as the ratio of IGFBP7/Htrp1 gene expression. n=3 per group, p<0.01 (unpaired two-tailed Student t-tests). (b), (c), and (d) show that knockdown of IGFBP7 diminished Angiotensin (AngII) induced hypertrophic and cellular senescence signaling in human cardiac myocytes. Human cardiac myocytes were treated with (−)control siRNA and IGFBP7 siRNA for 24 h, followed by AngII treatment for an additional 48 h. Solvent treated cells were used as control (NT). Relative Gene expression changes for hypertrophic marker Nppb (BNP) as well as cellular senescence markers Cdkn2a (p21) and Tp53 (p53) were measured by qRT-PCR, shown as fold change of indicated gene/HPRT1 against non-treated (−) control siRNA group (n=3 per group). In all panels, error bars represent s.e.m., one way ANOVA were used to calculate P values. (e) shows that knockdown of IGFBP7 reduced Dox induced cellular senescence in human cardiac myocytes. Cells were treated with (−) control siRNA and IGFBP7 siRNA for 24 h, followed by Dox (1 µM) treatment for an additional 72 h. Representative microscopy images showing increased SA-β-gal positive senescent cells (blue) in (−) control siRNA but not in IGFBP7 siRNA treatment human cardiac myocytes are shown. (Bar=20 µm)
Figure 8:
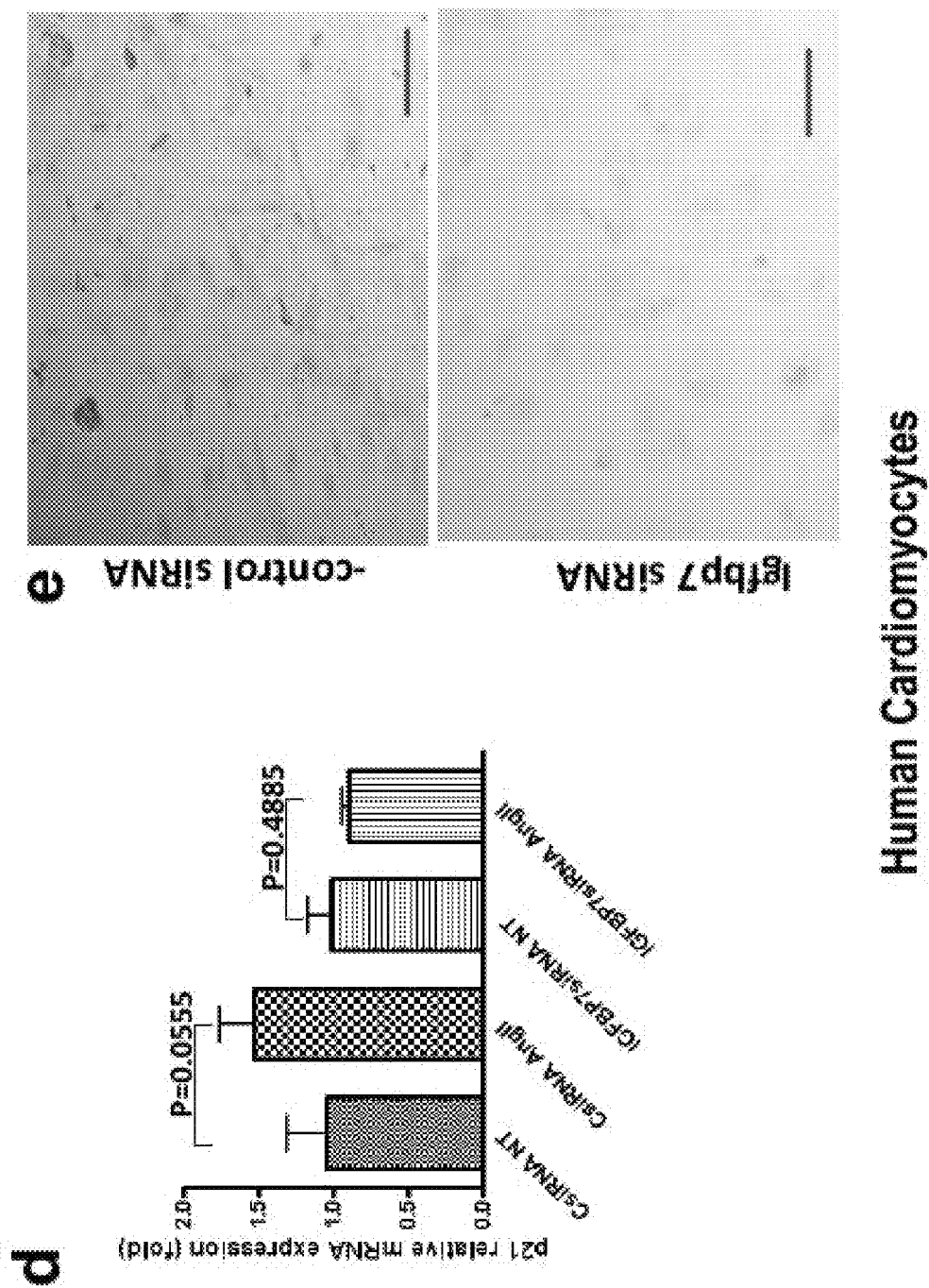

The combination of the above two siRNAs (siRNA 1 and siRNA 2) were delivered into HCM by using Lipofectamine RNAiMAX reagent (Thermo Fisher, Catalog number 13778) according to standard protocol provided by the supplier. Silencer select negative control No. 1 siRNA (Thermo Fisher, Catalog number: 4390844) treated cells were used as control. 72 hours post transfection, IGFBP7 mRNA knockdown efficacy was assayed by RT-qPCR as shown in FIG. 8a. Experimental results are provided in FIG. 8.

In FIG. 8, human cardiac myocytes obtained from PromoCell were treated with negative control siRNA and IGFBP7 siRNA. In FIG. 8(a), efficiency of IGFBP7 siRNA knockdown was checked 72 h post siRNA treatment by q-RT PCR with two IGFBP7 specific primer pairs. HTRP expression was used as control. IGFBP7 siRNA resulted in hundreds fold decrease in IGFBP7 gene expression shown as the ratio of IGFBP7/Htrp gene expression. In FIGS. 8(b), 8(c), and 8(d), knockdown of IGFBP7 diminished Angiotensin (AngII) induced hypertrophic and cellular senescence signaling in human cardiac myocytes. Human cardiac myocytes were treated with (−)control siRNA and IGFBP7 siRNA for 24 h, followed by AngII treatment for an additional 48 h. Solvent treated cells were used as control (NT). Relative Gene expression changes for hypertrophic marker Nppb (BNP) as well as cellular senescence markers p21 and p53 were measured by qRT-PCR, shown as fold change of indicated gene/HPRT1 against non-treated (−) control siRNA group. FIG. 8(e) shows that knockdown of IGFBP7 reduced Dox induced cellular senescence in human cardiac myocytes. Cells were treated with (−) control siRNA and IGFBP7 siRNA for 24 h, followed by Dox (1 μM) treatment for an additional 72 h. Representative microscopy images showing increased SA-β-gal positive senescent cells (blue) in (−) control siRNA but not in IGFBP7 siRNA treatment human cardiac myocytes are shown. (Bar=200 μm).

Together, these experimental results indicate that IGFBP7 knockdown using an example of an IGFBP7 inhibitor blocked hypertrophic and cellular senescence signaling in human cardiac myocytes under the conditions tested.

Example 8: IGFBP7 Knockdown Represses IGF-1/Insulin Induced AKT Activation in Human Cardiac Myocytes; and This Reduction was Further Enhanced by IGF-1R Inhibition This example indicates that under the conditions tested, IGFBP7 knockdown depresses IGF-1/Insulin induced AKT activation, and that this reduction may be further enhanced by IGF-1R inhibition. Experimental protocols are provided in the Methods section below, and results are provided in FIG. 9.

To further explore IGFBP7's role in controlling cardiac remodeling at the cellular level, we treated human cardiac myocytes with IGF-1, Insulin or Ang II to stimulate the IGF-1 pathway. Upon treatment, IGFBP7 were co-localized with both IGF-1 (FIG. 9f) and its receptor IGF-1Rb (FIG. 9g). To evaluate if inhibition of IGFBP7 will suppress IGF-1/IGF-1R induced AKT activation, siRNA were used to knockdown IGFBP7 in HCM. Both IGF-1 and Insulin treatment result in increased activation of AKT/GSK3β. However, inhibition of IGFBP7 by siRNA blocked this activation (FIG. 9a). Next, it was tested whether pre-treat HCM with IGF-1R inhibitor Picropodophyllin (PPP), before stimulation with IGF-1, will further depress AKT activation. As shown in FIG. 9d, AKT activation was further reduced by IGF-1R inhibition in IGFBP7 knock down cells but not in control siRNA cell. Down regulation of IGF-1 receptor-dependent signaling was further confirmed in IGFBP7 deficient MEF pre-treated with ppp (FIG. 9c). As indicated, inhibition of IGFBP7 may have a profound effect on IGF-1/Insulin dependent AKT activation. When IGFBP7 is intact, in the present of IGF-IR inhibitor, IGF-1 may still active AKT through Insulin receptor. Inhibition of IGFBP7 by siRNA reduced this activation. These results suggest that IGFBP7 inhibition may therefore affect both IGF-1 receptor and Insulin receptor medicated signaling.

IGFBP7 may regulate IGF-1/Insulin dependent signaling from external or internal of the cell. To investigate this, we treated HCM with either recombinant IGFBP7 protein or by internal over-expression of IGFBP7 with gene transfer. Internal over-expression of IGFBP7 in HCM significantly increased IGF-1/Insulin induced AKT and GSK3β activation, and this induction can be blocked by IGF-1/Insulin duel inhibitor BMS-754807 (FIG. 9e). In contrast, external IGFBP7 treatment has no such effect (FIG. 9d). There results indicate that IGFBP7 modulates IGF-1/Insulin dependent signaling within the cell.

Figure 9:
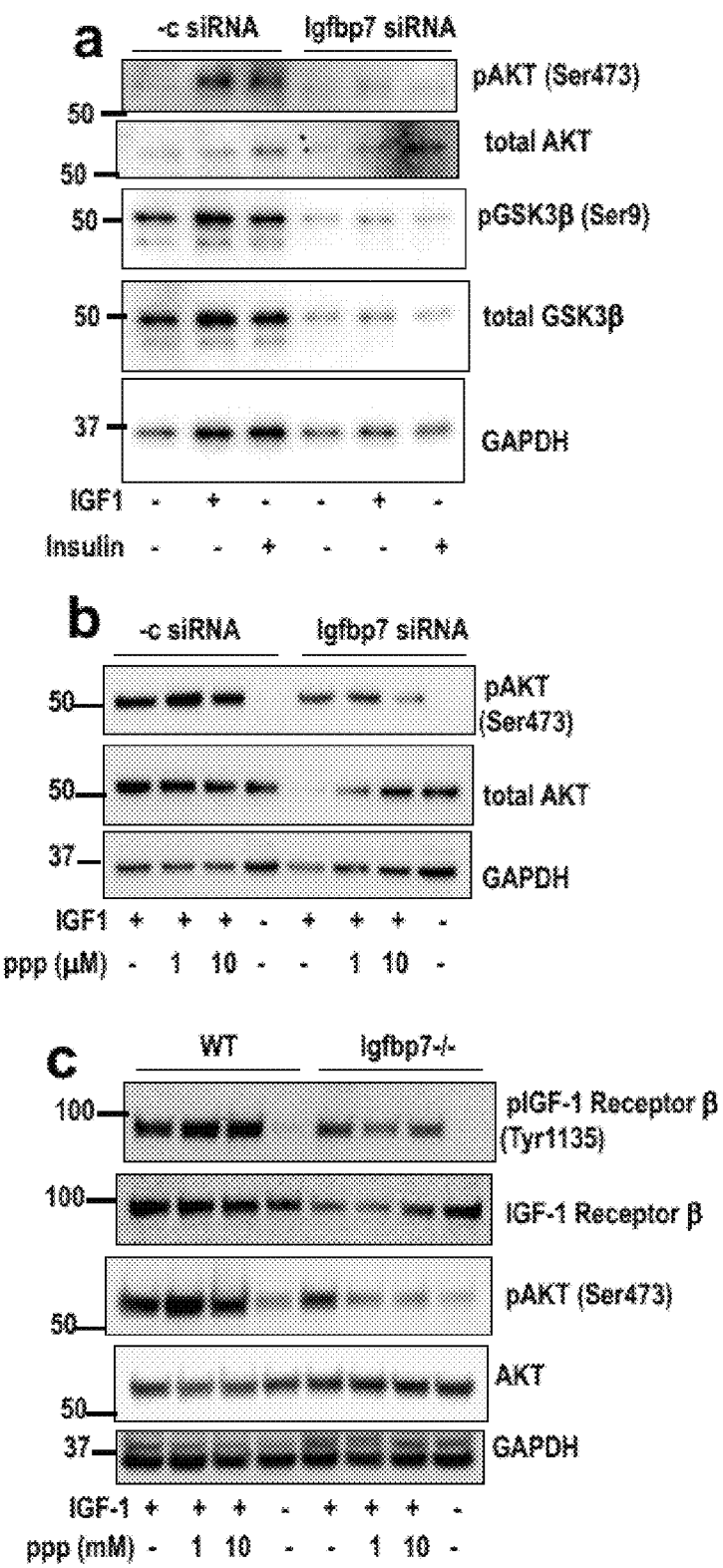
FIG. 9 shows that IGFBP7 knockdown depresses IGF-1/Insulin induced AKT activation, and that this reduction may be further enhanced by IGF-1R inhibition. Human cardiac myocytes were treated with (−)control siRNA and IGFBP7 siRNA for 48 h, followed by replacement with basic medium (serum and growth factors withdrew) for 4 h. In (a), the cells were then stimulated with IGF1 (100 ng/ml) or Insulin (4 µg/ml) for 15 min, before lyses of the cell for immunoblotting. Representative immunoblotting of phosphor-AKT, total AKT, phosph-GSK3β and total GSK3β are shown. GAPDH was used as loading control. In (b), before adding IGF-1, cells were pre-treated with IGF-1R inhibitor Picropodophyllin (PPP) ppp at 1 or 10 for 1 h, and finally stimulated with IGF-1 (100 ng/ml) for 15 min. Representative immunoblotting of phosphor-AKT and total AKT showing reduced AKT activity in IGFBP7 knock down cells is shown. GAPDH was used as loading control. Importantly, this reduction was further enhanced by IGF-1R inhibition in IGFBP7 knock down cells, but not in control siRNA cells. (c) shows that down-regulation of IGF-1 receptor-dependent signaling was further confirmed in IGFBP7 deficiency MEF pre-treated with ppp at 1 or 10 µM for 1 h, and finally stimulated with IGF-1 (100 ng/ml) for 15 min, as illustrated in panel (c) by the ratio of phosphor-IGF-1 Receptor β to total IGF-1 Receptor β; as well as phospho-Akt to total Akt. GAPDH were used as loading control. Moreover, pre-treatment with ppp further reduced IGF-1R and AKT phosphorylation in IGFBP7 deficient MEF but not in WT MEF. (d) Representative immunblotting showing external IGFBP7 had no observed effect on IGF-1/Insulin induced AKT and Gsk3β activation. HCM were pretreated with recombinant IGFBP7 protein at indicated concentration for 2 h, followed by IGF-1 or insulin induction for 15 min. Vinculin was used as loading control. (e) Representative immunblotting shown internal over-expression of IGFBP7 in HCM further increased IGF-1/Insulin induced Akt and Gsk3β activation, and this induction can be blocked by IGF-1/Insulin inhibitor BMS-754807 (500 nM). Representative Confocal Microscopy images showing (f) IGFBP7 (red) co-localized with both IGF-1 (green) and (g) IGF-1β (green) in HCM by immunofluoresent staining are shown. Nuclear were stained with DEPI (blue). Scale bars=10 µm in all images.
Figure 9:
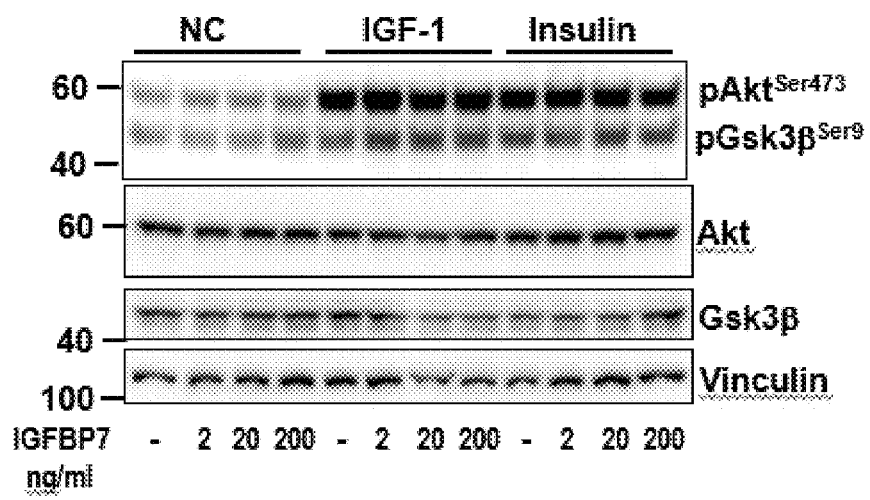
Figure 9:
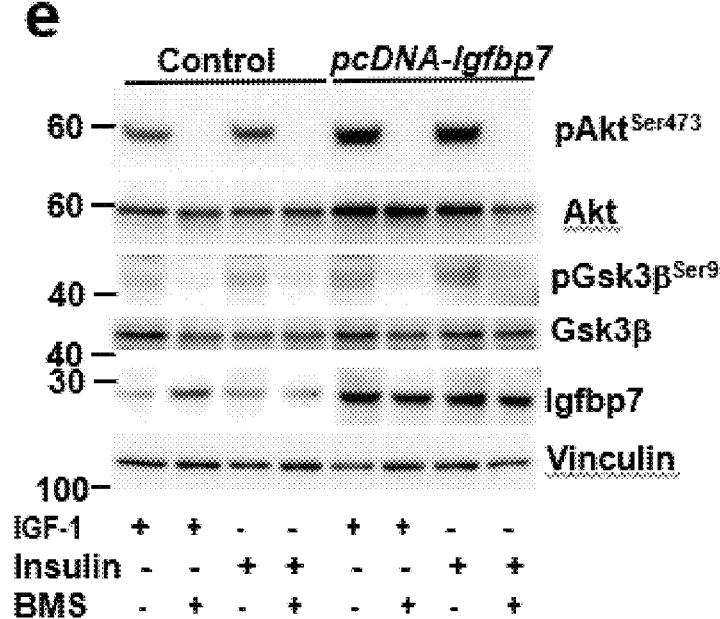
Figure 9:
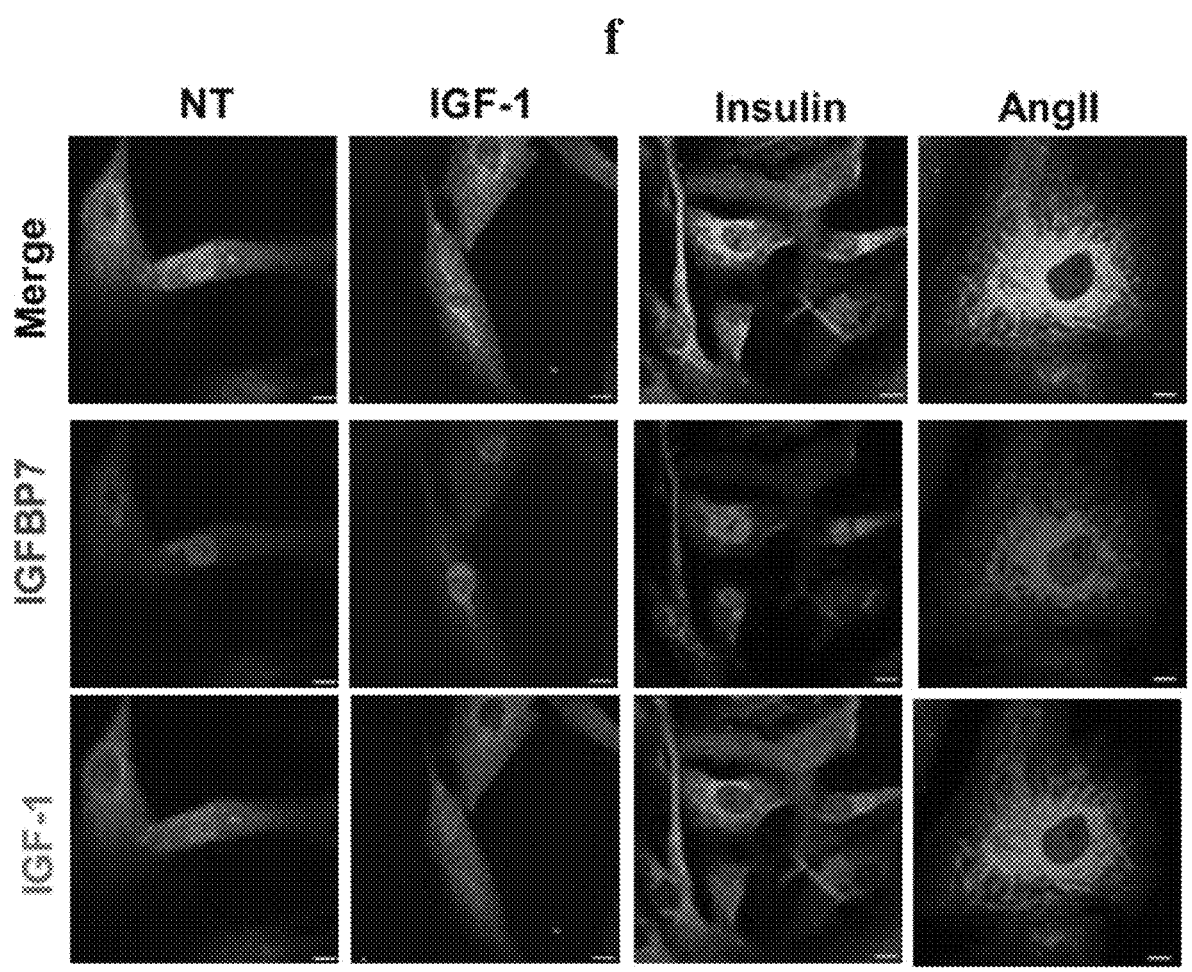
Figure 9:
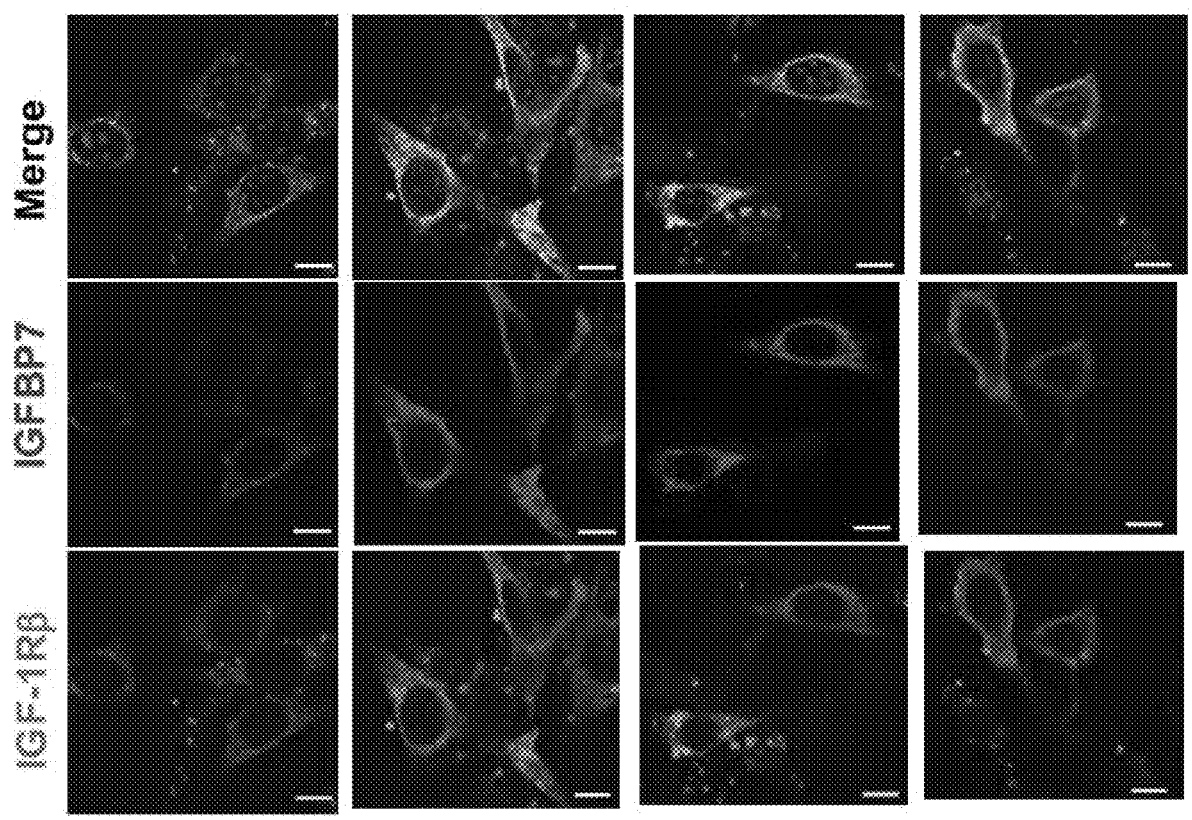

Indeed, in FIG. 9, human cardiac myocytes were treated with (−)control siRNA and IGFBP7 siRNA for 48 h, followed by replacement with basic medium (serum and growth factors withdrew) for 4 h. In FIG. 9(a), the cells were then stimulated with IGF1 (100 ng/ml) or Insulin (4 μg/ml) for 15 min, before lyses of the cell for immunoblotting. Representative immunoblotting of phosphor-AKT, total AKT, phosph-GSK3β and total GSK3β are shown. GAPDH was used as loading control. In FIG. 9(b), before adding IGF-1, cells were pre-treated with IGF-1R inhibitor Picropodophyllin (PPP) ppp at 1 or 10 μM for 1 h, and finally stimulated with IGF-1 (100 ng/ml) for 15 min. Representative immunoblotting of phosphor-AKT and total AKT showing reduced AKT activity in IGFBP7 knock down cells is shown. GAPDH was used as loading control. Importantly, this reduction was further enhanced by IGF-1R inhibition in IGFBP7 knock down cells, but not in control siRNA cells. FIG. 9(c) shows that down-regulation of IGF-1 receptor-dependent signaling was further confirmed in IGFBP7 deficiency MEF pre-treated with ppp at 1 or 10 μM for 1 h, and finally stimulated with IGF-1 (100 ng/ml) for 15 min, as illustrated in FIG. 9(c) by the ratio of phosphor-IGF-1 Receptor β to total IGF-1 Receptor β; as well as phospho-Akt to total Akt. GAPDH were used as loading control.

Pre-treatment with ppp further reduced IGF-1R and AKT phosphorylation in IGFBP7 deficient MEF but not in WT MEF.

In FIG. 9(d), representative immunblotting is provided showing that external IGFBP7 has no observed effect on IGF-1/Insulin induced AKT and Gsk3β activation. HCM were pretreated with recombinant IGFBP7 protein at indicated concentration for 2 h, followed by IGF-1 or insulin induction for 15 min. Vinculin was used as loading control. In FIG. 9(e), representative immunblotting is shown, indicating that internal over-expression of IGFBP7 in HCM further increased IGF-1/Insulin induced Akt and Gsk3β activation, and this induction can be blocked by IGF-1/Insulin inhibitor BMS-754807.

Together, these experimental results indicate that IGFBP7 knockdown depresses IGF-1/Insulin induced AKT activation, and that this reduction may be further enhanced by IGF-1R inhibition under the conditions tested.

Example 9: Igfbp7 Deficiency Reduced Reactive Oxygen Species (ROS) and Ubiquitinated Protein Accumulation in Myocardium This example indicates that under the conditions tested, IGFBP7 deficiency partially blocked reactive oxygen species (ROS) and ubiquitinated protein accumulation in myocardium. Experimental protocols are provided in the Methods section below, and results are provided in FIG. 10.

Increased reactive oxygen species (ROS) and ubiquitinated protein accumulation inside the cell is an important feature of cellular senescence. Autophagy is important to maintain cell stemness by preventing senescence (García-Prat L, Martínez-Vicente M, Perdiguero E, Ortet L, Rodríguez-Ubreva J, Rebollo E, Ruiz-Bonilla V, Gutarra S, Ballestar E, Serrano A L, Sandri M, Muñoz-Cánoves P. 2016, Autophagy maintains stemness by preventing senescence. Nature, 529:37-42.).

Autophagy mediated protein degradation is also important for protecting heart from stress induced ROS and abnormal protein accumulations in the myocardium (Zhang L, Chen X, Sharma P, Moon M, Sheftel A D, Dawood F, Nghiem M P, Wu J, Li R K, Gramolini A O, Sorensen P H, Penninger J M, Brumell J H, Liu P P. 2014, HACE1-dependent protein degradation provides cardiac protection in response to haemodynamic stress. Nat Commun., 5:3430).

To explore if autophagic protein degradation is regulated by IGFBP7, Igfbp7−/− and WT TAC heart lysate were subject to immunoblotting with antibody to LC3 and p62, makers for protein accumulation. As shown in FIG. 10a, both LC3 and p62 level are significantly reduced in Igfbp7$^{-/-}$ TAC heart, indicated, that Igfbp7 deficiency, reduced abnormal protein aggregation in stressed myocardium. Next we exposed control and Igfbp7 siRNA knockdown HL-1 cardiomycytes to proteasome inhibitor MG132, 48 hours after treatment, cell were fixed and co-stained with CellRox green and anti Ubiquitinylated proteins antibody. Again, both ROS and Ub+ staning are significantly reduced in Igfbp7 siRNA treated cells. This is a further indication that Igfbp7 deficiency reduced reactive oxygen species (ROS) and ubiquitinated protein accumulation in myocardium.

Figure 10:
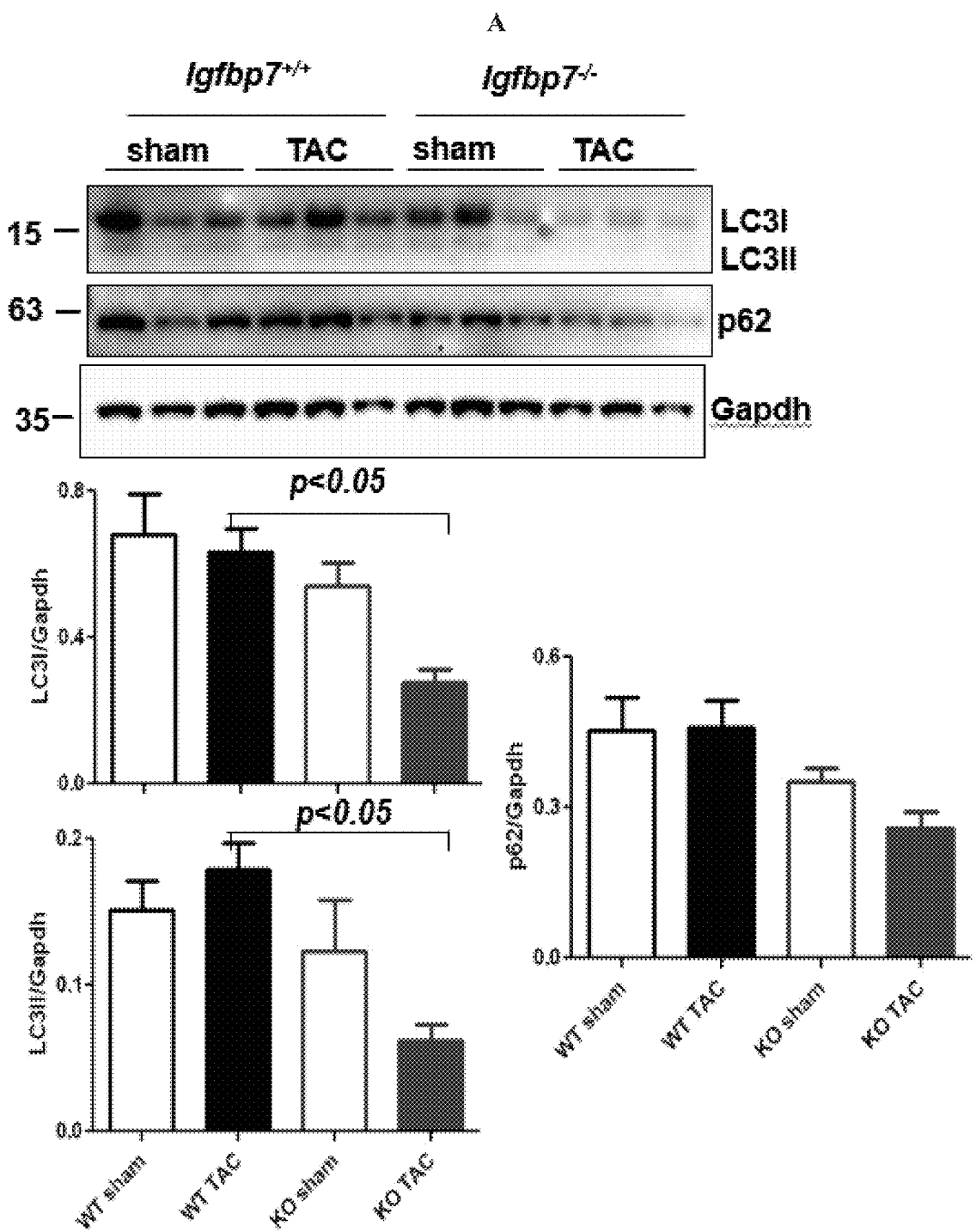
FIG. 10 shows that Igfbp7 deficiency reduced reactive oxygen species (ROS) and ubiquitinated protein accumulation in myocardium. Igfbp7$^{-/-}$ and WT mice were subjected to TAC or sham surgery and analyzed 8 weeks after the operation. (a) Representative Immunoblotting and quantification for selective autophagy markers LC3II and p62 in heart extracts (n=3 per group), Gapdh were used as loading control. In all panels error bars represent s.e.m., one way ANOVA were used to calculate P values. (b) representative confocal microscopy images showing knockdown of Igfbp7 by siRNA diminished MG132 induced ROS (green) and ubiquitinated protein (red) accumulation in HL-1 cardiomyocytes. HL-1 cardiomocytes were treated with −control and Igfbp7 siRNA for 24 hours, followed by treatment with MG132 for 48 hours.
Figure 10:
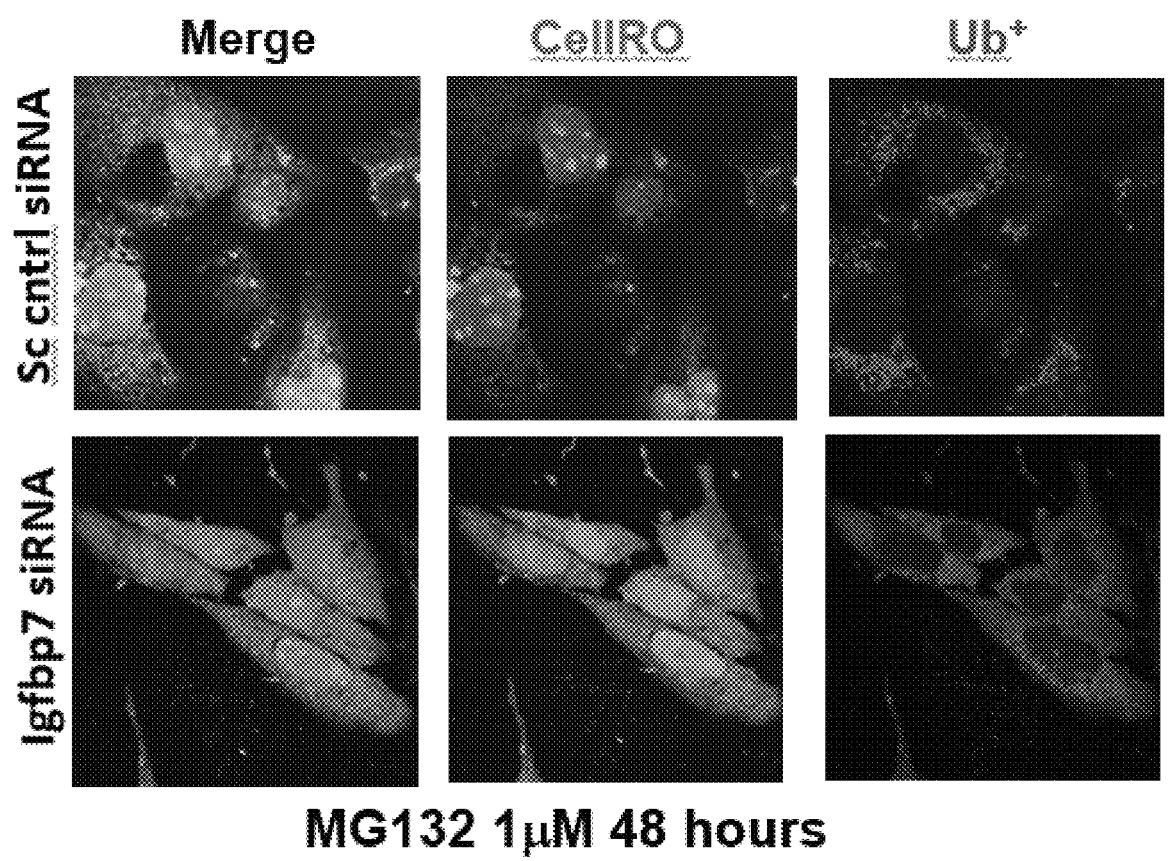

Indeed, in FIG. 10, Igfbp7$^{-/-}$ and WT mice were subjected to TAC or sham surgery and analyzed 8 weeks after the operation. (a) Representative Immunoblotting and quantification for selective autophagy markers LC3II and p62 in heart extracts (n=3 per group), Gapdh were used as loading control. In all panels error bars represent s.e.m., one way ANOVA were used to calculate P values. (b) representative confocal microscopy images showing knockdown of Igfbp7 by siRNA diminished MG132 induced ROS (green) and ubiquitinated protein (red) accumulation in HL-1 cardiomyocytes. HL-1 cardiomocytes were treated with –control and Igfbp7 siRNA for 24 hours, followed by treatment with MG132 for 48 hours.

Example 10: Igfbp7 Deficiency Lead to Down-Regulation of Innate Immune Responses in Stressed Myocardium This example indicates that under the conditions tested, IGFBP7 deficiency blocks excessive MyD88 mediated innate immune activation in response to Doxorubicin induced cardiac toxicity in Cardiomyocytes, as shown in FIG. 11.

Figure 11:
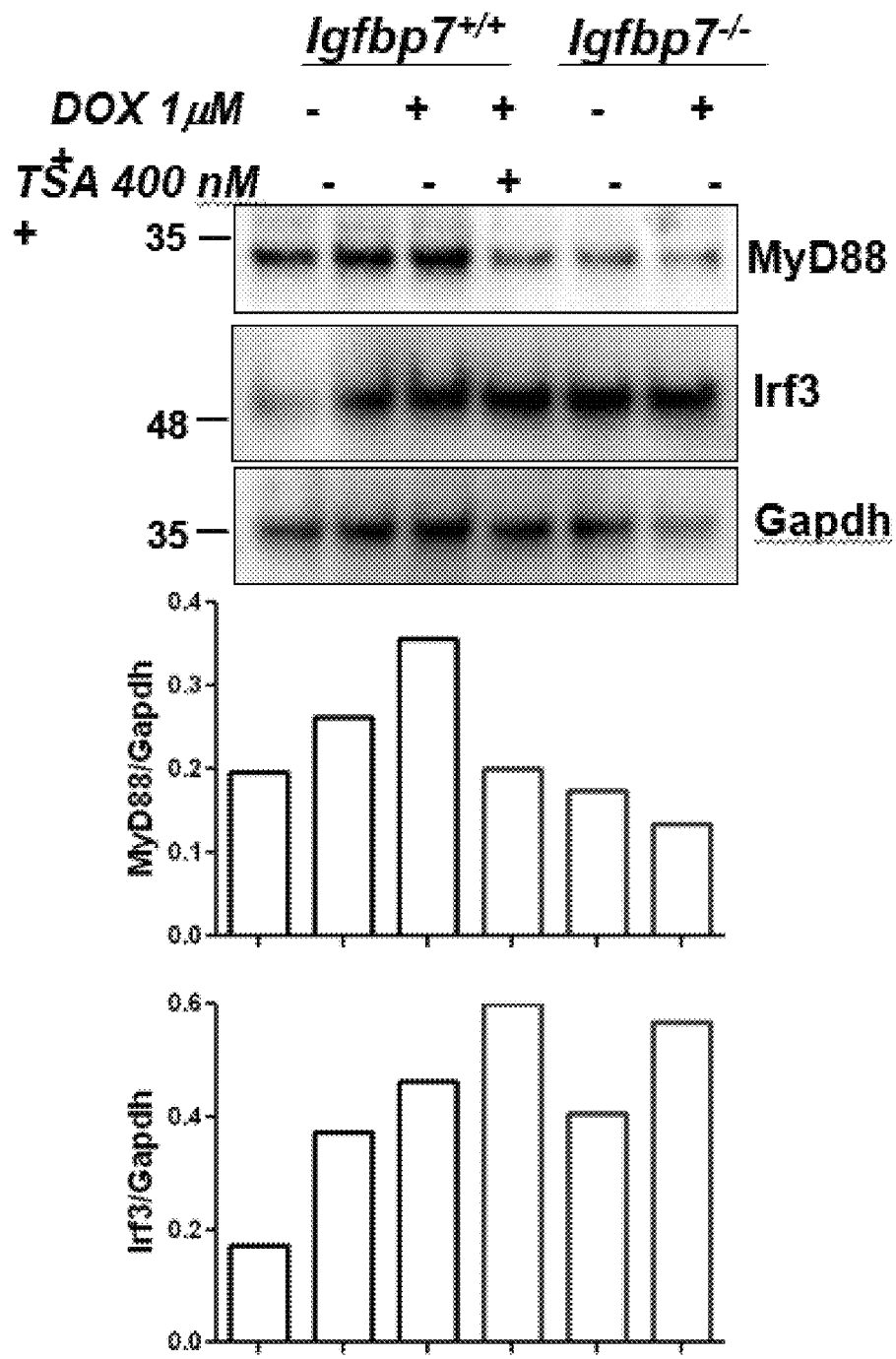
FIG. 11 shows that Igfbp7 deficiency led to down-regulation of innate immune responses in stressed myocardium. Igfbp7$^{-/-}$ and WT neonatal cardiomyocytes (NCM) were isolated from new born pups and were subject to Doxorubicin (DOX) (1 µM), or Doxorubicin plus Trichostatin A (TSA) (400 nM) for overnight treatment. Representative Immunoblotting and quantification for markers of activation of MyD88 dependent (MyD88) and Independent (Irf3) innate immune pathway, Gapdh were used as loading control.

Indeed, in FIG. 11, Igfbp7$^{-/-}$ and WT neonatal cardiomyocytes (NCM) were isolated from new born pups and were subject to Doxorubicin (DOX) (1 µM), or Doxorubicin plus Trichostatin A (TSA) (400 nM) for overnight treatment. Representative Immunoblotting and quantification for markers of activation of MyD88 dependent (MyD88) and Independent (Irf3) innate immune pathway, Gapdh were used as loading control.

Experimental Methods

Detection of IGFBP7 Protein.

The collection and use of human samples in these studies were approved by the Ottawa Health Science Network Research Ethics Board and informed consent was obtained from patients/family members. IGFBP7 protein expression in human and mouse samples was detected by immunofluorescent staining and immunoblotting analyses using standard procedures. Explanted heart samples (infarct zone and normal zone) from a transplant recipient that suffered from myocardial infarction were used for this study. Samples were fixed with neutral buffered 10% formalin solution (Sigma, HT501128) overnight, embedded in paraffin and sectioned to a thickness of 5 µm.

Mice Strains and Creation of Pressure Overload Mouse Model.

Igfbp7-null mice in CD1 background were obtained from Dr. Arun Seth's group at Sunnybrook Research Institute, and were generated as reported previously (Chatterjee S, Bacopulos S, Yang W, Amemiya Y, Spyropoulos D, Raouf A, Seth A. Loss of Igfbp7 causes precocious involution in lactating mouse mammary gland. *PLoS One.* 9, e87858 (2014); herein incorporated by reference in its entirety). Mice were genotyped by PCR (see Chatterjee et al., 2014) and maintained at the Animal Care and Veterinary Service Facility, University of Ottawa. All animal experimental protocols were approved by the Animal Care and Use Committee of University of Ottawa and performed in accordance with institutional guidelines.

8-10 weeks old Igfbp7$^{-/-}$ and control WT mice with a body weight at around 25 g were subjected to pressure overload by transverse aortic constriction (TAC) as previously described (Kuba K, Zhang L, Imai Y, Arab S, Chen M, Maekawa Y, Leschnik M, Leibbrandt A, Markovic M, Schwaighofer J, Beetz N, Musialek R, Neely G G, Komnenovic V, Kolm U, Metzler B, Ricci R, Hara H, Meixner A, Nghiem M, Chen X, Dawood F, Wong K M, Sarao R, Cukerman E, Kimura A, Hein L, Thalhammer J, Liu P P, Penninger J M. Impaired heart contractility in Apelin gene-deficient mice associated with aging and pressure overload. *Circ Res.* 101, e32-42 (2007); herein incorporated by reference in its entirety). In brief, mice were anesthetized with ketamine (IP; 90 mg/kg) and Rompan (IP; 10 mg/kg). The chest was opened, and a horizontal skin incision was made at the level of the 2 to 3 intercostal space. The start of the descending aorta was identified right after the subclavian branch. A 7-0 silk suture was placed around the beginning of the descending aorta and tied around a 26-gauge blunt needle, which was subsequently removed. At the end of the procedure, the chest and skin were closed. The mice were kept on a heating pad until responsive to stimuli. Sham-operated animals underwent the identical procedure, except that the aortic constriction was not placed. The mice were monitored for up to 8 weeks after surgery, and their heart functions were determined by serious echocardiography before surgery and at 2, 4, 6 and 8 weeks post-surgery. Mice were randomized to sacrifice on weeks 2 and 8 posts banding, for evaluation of morphology, function and detailed molecular expression analysis, as well as blood sampling for production of Igfbp7 in serum. For histological analysis, hearts and lung were arrested with 1 mol/L KCl, fixed with neutral buffered 10% formalin solution (Sigma, HT501128). For mRNA and protein analyses, hearts were snap-frozen in liquid nitrogen and stored at –80° C. until analysis.

Echocardiography and Invasive Hemodynamics.

Echocardiographic and hemodynamic measurements were performed as previously described (Kuba K, Zhang L, Imai Y, Arab S, Chen M, Maekawa Y, Leschnik M, Leibbrandt A, Markovic M, Schwaighofer J, Beetz N, Musialek R, Neely G G, Komnenovic V, Kolm U, Metzler B, Ricci R, Hara H, Meixner A, Nghiem M, Chen X, Dawood F, Wong K M, Sarao R, Cukerman E, Kimura A, Hein L, Thalhammer J, Liu P P, Penninger J M. Impaired heart contractility in Apelin gene-deficient mice associated with aging and pressure overload. Circ Res. 101, e32-42 (2007)). Briefly, mice were anesthetized with isoflurane (1%)/oxygen, and echocardiography was performed using an Acuson Sequoia C256 equipped with a 15-MHz linear transducer. Fractional shortening (FS) was calculated as follows: FS=[(LVEDD−LVESD)/LVEDD]×100. Vcfc was calculated as FS/ejection time corrected for heart rate. We used 2D-guided M-mode measurements to determine % FS. The heart was first imaged in 2D mode in the parasternal short-axis view. From this view, an M-mode cursor was positioned perpendicular to the interventricular septum and posterior wall of the LV at the level of the papillary muscles, and M-mode images were obtained for measurement of wall thickness and chamber dimensions with the use of the leading-edge convention adapted by the American Society of Echocardiography. For rescue experiments, osmotic minipumps (Alzet 1002) were loaded with Apelin-13 peptide (1 mg/kg/24 hour) in saline or saline alone and implanted subcutaneously into the dorsal region of control wild type or Apelin knockout mice. Mice were infused continuously for 2 weeks before echocardiography measurements were performed. For hemodynamic assessment, the right carotid artery was cannulated with a 1.4 French Millar catheter (Millar, Inc., Houston, Tex.) connected to an amplifier (TCP-500; Millar, Inc.). After insertion of the catheter into the carotid artery, the catheter was advanced into the aorta and then into the left ventricle to record aortic and ventricular pressures as well as volume conductance.

Histology, Immunohistochemistry.

For morphometry, fixed hearts and lungs were embedded in paraffin and sectioned to a thickness of 5 µm. Alexa Fluor 488 conjugated wheat germ agglutinin (WGA) (ThermoFisher, W11261) stained sections were used for measurement of heart morphology, and cardiomyocytes cross-sectional area were measured using FV10-ASW2.1 Viewer software (Olympus Corporation). For detection of fibrotic areas, sections were stained with Picro Sirius Red to visualize collagen fibers. For immunofluorensent staining, samples were fixed with buffered 4% paraformaldehyde, and paraffin sections were performed with minimal antigen retrieval (10 mM Sodium Citrate Buffer) followed by a cell permeabilization step with 0.1% Triton X-100 in PBS. After block with 10% FBS in PBS for 30 min at RT, the following antibodies were used for staining: Anti-IGFBP7 (Abcam, ab74169 1:200), FM 1-43FX membrane probe (ThermoFisher, F35355), anti-IGF1 (Abcam, ab9572). Following overnight incubation with primary antibody, the sections were incubated with a matching Alexa Fluor Dyes conjugated secondary antibody (ThermoFisher, 1:1000) at room temperature for 1 hour, and were mounted with SlowFade Gold antifade reagent with DAPI (ThermoFisher, S36939) and subjected to confocal examination on an Olympus FluoView 1000 Laser Scanning Confocal Microscope. The total fluorescence intensity from the staining was measured using Olympus FV10-ASW2.1 Viewer software.

Immunoblotting.

Whole-cell lysates from tissue and cell samples were prepared on ice with Cell Lysis Buffer (Cell Signaling, 9803) containing a Complete cocktail of proteases inhibitors (Roche Applied Science, 05892791001). Lysates were cleared by centrifugation at 12,000 rpm for 10 min. The supernatants were collected and protein concentrations determined using the Bio-Rad Bradford protein assay (Bio-Rad, 500-0006). 20 µg of protein lysate were separated by Bolt Bis-Tris Plus mini Gel System (ThermoFisher) and electrophoretically transferred to PVDF membranes (Bio-Rad, 162-0177). Membranes were incubated overnight at 4° C. with antibodies reactive to the following proteins: IGFBP7 (Abcam, ab171085, 1:1000), CTGF (Abcam, ab6992, 1:1000), 53BP1 (Santa Cruz Biotechnology, sc-22760, 1:200), p21 (Santa Cruz Biotechnology, sc-397, 1:200), Acetyl-p53 (Lys379) (Cell Signaling, #2570, 1:1000), p53 (1C12) (Cell Signaling, #2524, 1:1000), Phospho-IRS-1 (Ser612) (Cell Signaling, #3203, 1:500), Phospho-IRS-1 (Ser318) (Cell Signaling, #5610, 1:500), IRS-1 (Cell signaling, #3407, 1:500), Phospho-Akt (Ser473) (Cell Signaling, #4060, 1:1000), Phospho-Akt (Thr308) (Cell Signaling, #4056, 1:1000), Akt (pan) (Cell Signaling, #4691, 1:1000), Phospho-Erk1/2 (Thr202/Tyr204) (Cell Signaling, #4307, 1:1000), Erk1/2 (Cell Signaling, #9102, 1:1000), Phospho-GSK-3β (Ser9) (Cell Signaling, #9323, 1:1000), GSK-3β (Cell Signaling, #9315, 1:1000), Phospho-IGF-1 Receptor β ((Thy1135) (Cell Signaling, #3918, 1:500), IGF-1 Receptor β (Cell Signaling, #9750, 1:500). Blots were incubated with HRP-conjugated Goat anti-mouse IgG (Bio-Rad, 170-5046, 1:50,000), Goat anti-rabbit IgG (Bio-Rad, 170-5047, 1:100,000), monoclonal mouse anti-goat IgG (Jackson ImmunoResearch, 205-032-176, 1:50,000) and developed using Clarity Western ECL Substrate (Bio-Rad, 170-5061) or SuperSignal West Femto Maximum Sensitivity Substrate (ThermoFisher, 34095). The intensity of the chemiluminescence signals were detected by using the ChemiDoc XRS+ System (Bio-Rad, 1708265) and quantified using Image Lab software (version 5.2; Bio-Rad). To normalize signals to total protein, blot membranes were stripped and re-probed with antibody against GAPDH (ThermoFisher, MA5-15738, 1:5000) or Vinculin (Sigma, V4505, 1:1000).

Isolation and Culture of Mouse Neonatal Ventricular Cardiomyocytes (NCM).

Cell culture of neonatal mouse cardiomyocytes was prepared from newborn Igfbp7$^{-/-}$ and WT mouse hearts within 48 hours of birth. Briefly, after trimming, left ventricles were mechanically minced in $Ca^{2+}$ and $Mg^{2+}$ free Hanks balanced salt solution (HBSS) on ice, and then subjected to stepwise enzymatic digestion with 0.15% trypsin (ThermoFisher, 27250018) in disassociation solution (137 mmol/L NaCl, 5.36 mmol/L KCl, 0.81 mmol/L $MgSO_4$, 5.55 mmol/L dextrose, 0.44 mmol/L $KH_2PO_4$, 0.34 mmol/L $Na_2HPO_47H_2O$, and 20.06 mmol/L Hepes, pH 7.4). Cells released after the first digestion were discarded, whereas cells from subsequent digestion were transferred into GIBCO DMEM/F-12 medium (ThermoFisher, 11320033) supplemented with 10% FBS (ThermoFisher, 12483020) until all cardiac cells were isolated (~5 times). The resulting mixture was centrifuged for 5 min at 800 rpm, resuspended in DMEM/F-12 medium and preplating for 2 hours to remove non-cardiomyocytes based on the observation that non-muscle cells attach to the substrata more rapidly. The cardiomyocytes were then collected and plated on laminin-coated culture plates at a density of $2 \times 10^6$ cells/ml in DMEM/F-12 plus 10% FBS and 0.1 µM Brdu (to inhibit growth of non-myocytes). Cells were incubated at 37° C. with 5% $CO_2$ in a humidified atmosphere. A confluent monolayer of spontaneously beating cardiomyocytes was formed within 2 days and was ready for downstream gene transfer and treatment.

For induction of cellular senescence, Igfbp7$^{-/-}$ and WT NCM were treated with doxorubicin (Sigma, D1515) (1 µM) or Dox (1 µM)+Trichostatin A (Sigma,T8552) (400 nM) for 3 days, before harvesting for immunoblotting with cellular senescence marker acetylated p53 (Acetl-p53) and total p53 as described in the section of Immunobotting. Solvent treated cells were use as control (NT).

Quantitative Reverse Transcription PCR (RT-qPCR).

Isolation of total RNA from heart tissues was performed using the Trizol reagent (ThermoFisher, 15596026), and from culture cells using PureLink RNA Mini Kit (ThermoFisher, 12183018A). cDNAs were synthesized from 1 µg total RNA with the iScript Reverse Transcription Supermix for RT-PCR (Bio-Rad, 170-8841). Quantitative RT-PCR was carried out using SYBR green assays (Roche Applied Science, 04707516001) with IGFBP7 specific primers and both HPRT and GAPDH as endogenous control. Real-time PCR reactions were carried out in 96-well plates using a Roche-LightCycler 96 System. All primer sequences are listed in Table 2.

TABLE 2

Primer Sequences (5' to 3') used for RT-qPCR

Primer Pairs Used for RT-qPCR

Human IGFBP7: Primer Pair 1 actggctgggtgctggta (SEQ ID NO: 13)　　tggatgcatggcactcata (SEQ ID NO: 14)

Human IGFBP7: Primer Pair 2 gaatcccgacacctgtcctc (SEQ ID NO: 15)　　cagcacccagccagttactt (SEQ ID NO: 16)

Human HPRT1 tgacactggcaaaacaatgca (SEQ ID NO: 17)　　ggtccttttcaccagcaagct (SEQ ID NO: 18)

Human NPPB caccgcaaaatggtcctcta (SEQ ID NO: 19)　　gtccatcttcctcccaaagc (SEQ ID NO: 20)

Human Tp53 cagcacatgacggaggttgt (SEQ ID NO: 21)　　tcatccaaatactccacacgc (SEQ ID NO: 22)

Human p21 tgtccgtcagaacccatgc (SEQ ID NO: 23)　　Aaagtcgaagttccatcgctc (SEQ ID NO: 24)

Mouse Nppa gcttccaggccatattggag (SEQ ID NO: 25)　　gggggcatgacctcatctt (SEQ ID NO: 26)

Mouse Nppb gaggtcactcctatcctctgg (SEQ ID NO: 27)　　gccatttcctccgactttctc (SEQ ID NO: 28)

Mouse Trp53 cacgtactctcctccctcaat (SEQ ID NO: 29)　　aactgcacagggcacgtctt (SEQ ID NO: 30)

Mouse Myh6 tgcactacggaaacatgaagtt (SEQ ID NO: 31)　　cgatggaatagtacacttgctgt (SEQ ID NO: 32)

Mouse Myh7 actgtcaacacttaagagggtca (SEQ ID NO: 33)　　ttggatgatttgatcttccaggg (SEQ ID NO: 34)

Mouse Hprt1 gctgacctgctggattacat (SEQ ID NO: 35)　　ttggggctgtactgcttaac (SEQ ID NO: 36)

siRNA Knockdown of IGFBP7 in Human Cardiac Myocytes and Treatments.

Human cardiac myocytes (HCM) obtained from PromoCell (c-12810) were seeded in 6 well plate containing myocyte growth medium (PromoCell C-22070), at a density of 10,000 cells per cm$^2$, in a humidity controlled incubator at 37° C., 5% $CO_2$ for about 24 hours until cells reached about 70% confluent before starting siRNA treatment. Knockdown of IGFBP7 in HCM were achieved using two silencer select pre-designed siRNA specific to human IGFBP7 (ThermoFisher, siRNA ID s7239, UGGUAUCUC-CUCUAAGUAAtt and siRNA ID s7240, CGAGCAAGGU-CCUUCCAUAtt). The combination of the above two siRNA were delivered into HCM by using Lipofectamine RNAiMAX reagent (ThermoFisher, 13778). Silencer select negative control No. 1 siRNA (ThermoFisher, 4390844) treated cells were used as control. IGFBP7 mRNA knockdown in HCM was confirmed by RT-qPCR. 48 h after siRNA treatment, start the treatment first by replace the complete medium with basic myocyte growth medium without supplements for 4 h, followed by induction with IGF-1 (100 ng/ml) (R&D Systems, 291-G1-200) or insulin (40 µg/ml) (Sigma, 91007C) for 15 min. Whereas indicated, a pretreatment step with IGF-1R inhibitor Picropodophyllotoxin (ppp) (R&D Systems, 2956) or IGF1R/InsR inhibitor BMS-754807 (Selleckchem, S1124) were added 1 h prior to induction.

Generation of IGFBP7 Expression Plasmid and Recombinant Human IGFBP7 Protein.

To generate IGFBP7 expression plasmid, human IGFBP7 CDS with 6× His Epitope tag added to the 3'-end were generated by GeneArt gene synthesis and subcloned into pcDNA3.4 TOPO TA Cloning vector (ThermoFisher) to make plasmid pcDNA3.4-hIGFBP7-6× His. Sequences of hIGFBP7-CDS plasmid (no 6× His tag) and hIGFBP7-CDS-6× His (with 6× His tag) are shown in FIGS. 1I and 1J as SEQ ID NOs: 37 and 38, respectively. In order to generate high yield recombinant human IGFBP7 protein with biological activity, the new Expi293 Expression System was used, which features high-density mammalian transient protein expression. In brief, after establishing cell suspension culture of Expi293F cells, pcDNA3.4-hIGFBP7-6× His plasmid was transfected into Expi293F cells, using Expi293 Expression System kit (ThermoFisher, A14635) according to the standard protocol. Expression of secreted IGFBP7-6× His recombinant protein in culture media was monitored daily by immonoblotting with anti 6× His Epitope Tag antibody (ThermoFisher, MA1-21315). 6 days after transfection, cell culture media containing secreted IGFBP7 recombinant protein was collected, purified and concentrated by using Amicon Ultra centrifugal filter units (Sigma, Z706345). The purified recombinant IGFBP7 protein was used to test the effect of external IGFBP7 on IGF-1R/InsR activation in HCM. In brief HCM were pretreated with recombinant IGFBP7 protein at indicated concentration for 2 h, followed by IGF-1 or insulin induction for 15 min.

In order to test the effect of internal over-expression of IGFBP7 on the activation of IGF-1R/InsR signaling pathways, Transient transfection of pcDNA3.4-hIGFBP7-6× His plasmid constructs into HCM were carried out by using Lipofectamin 3000 Transfection Reagent (ThermoFisher, L3000015) or a Neon Transfection System (ThermoFisher) according to standard protocols. Expression of transit transfected IGFBP7 was confirmed by immunoblotting with either anti 6× His Epitope Tag antibody (ThermoFisher, MA1-21315) or IGFBP7 antibody. 48 h after transfection, HCM were pretreated with basic medium for 4 h, followed by treatment with IGF-1/Insulin inhibitor BMS-754807 (500 nM) for additional 1 h before induction with IGF-1 or Insulin for 15 min.

Cellular Senescence Assay.

Cellular senescence assay were performed with both human cardiac myocytes (HCM) and mouse neonatal cardiomyocytes (NCM) culture. HCM cultured on Millicell EZ slides (Millipore, PEZQSO416) were first treat with IGFBP7 siRNA or (−)control siRNA as described in the small interference RNA section. 24 h after siRNA treatment, Doxorubicin were added to the culture media with a final concentration at 1 µM for additional 72 h. After wash with PBS, cells were fixed and stained with cellular senescence assay kit (Millipore, KAA002) to detect the induction of senescence-associated β-galactosidase (AS-β-gal) activity following the standard procedure provided by the manufacture and the images were taken using Nikon light microscopy. Similarly, $Igfbp7^{-/-}$ and WT NCM were treated with doxorubicin for 7 days before process to cellular senescence assay.

Statistical Analysis.

For all multiple comparisons of normally distributed data, one way ANOVA followed by Bonferroni's multiple comparison post tests were used, while, for comparison of two groups of normally distributed data, unpaired two-tailed Student t-tests were used. Statistical analyses were conducted using GraphPad Prism 5 software. All values are presented as means±s.e.m. n refers to the sample size. $P<0.05$ was considered significant.

All references cited in this specification are herein incorporated by reference in their entirety.

One or more illustrative embodiments have been described by way of example. It will be understood to persons skilled in the art that a number of variations and modifications can be made without departing from the scope of the invention as defined in the claims.

What is claimed is:

1. A method for the treatment of heart failure in a subject in need thereof, said method comprising:
   administering an insulin-like growth factor-binding protein 7 (IGFBP7) inhibitor comprising a gene silencing nucleic acid targeting an IGFBP7 gene or an IGFBP7 mRNA in said subject to said subject to directly reduce IGFBP7 expression and/or activity levels in the heart of said subject,
   thereby treating heart failure in said subject.

2. The method of claim 1, additionally comprising:
   administering an insulin-like growth factor 1 receptor (IGF-1R) inhibitor to said subject to directly inhibit IGF-1R expression and/or activity levels in the heart of said subject, wherein the IGF-1R inhibitor is selected from a group consisting of a gene silencing nucleic acid targeting an IGF-1R gene or an IGF-1R mRNA; an anti-IGF-1R antibody and/or picropodophyllin.

3. The method of claim 1, wherein the subject is human.

4. The method of claim 1, wherein the heart failure is pressure overload induced heart failure.

5. The method of claim 1, wherein the method attenuates pressure overload induced cardiac fibrosis, fibrosis remodeling, or both, in said subject.

6. The method of claim 1, wherein the method reduces stress-induced cellular senescence in said subject.

7. The method of claim 1, wherein the method reduces cardiac hypertrophy, hypertrophic remodeling, or both, in said subject.

8. The method of claim 1, wherein the heart failure is heart failure with preserved ejection fraction (HFpEF).

9. A method for the treatment of heart failure in a subject in need thereof, said method comprising:
   administering an insulin-like growth factor-binding protein 7 (IGFBP7) inhibitor comprising an anti-IGFBP7 antibody to said subject to directly reduce IGFBP7 expression and/or activity levels in the heart of said subject,
   thereby treating heart failure in said subject.

10. The method of claim 9, wherein the heart failure is pressure overload induced heart failure.

11. The method of claim 9, wherein the method attenuates pressure overload induced cardiac fibrosis, fibrosis remodeling, or both, in said subject.

12. The method of claim 9, wherein the method reduces stress-induced cellular senescence in said subject.

13. The method of claim 9, wherein the method reduces cardiac hypertrophy, hypertrophic remodeling, or both, in said subject.

14. The method of claim 9, wherein the heart failure is heart failure with preserved ejection fraction (HFpEF).

15. The method of claim 9, wherein the subject is human.

16. The method of claim 9, additionally comprising:
   administering an insulin-like growth factor 1 receptor (IGF-1R) inhibitor to said subject to directly inhibit IGF-1R expression and/or activity levels in the heart of said subject, wherein the IGF-1R inhibitor is selected from a group consisting of a gene silencing nucleic acid targeting an IGF-1R gene or an IGF-1R mRNA, an anti-IGF-1R antibody and/or picropodophyllin.

17. A method for the treatment of heart failure in a subject in need thereof, said method comprising:
   administering an insulin-like growth factor-binding protein 7 (IGFBP7) inhibitor to said subject to directly reduce IGFBP7 expression and/or activity levels in the heart of said subject wherein the inhibitor is selected from a group consisting of a gene silencing nucleic acid directly targeting an IGFBP7 gene or an IGFBP7 mRNA and/or an anti-IGFBP7 antibody; and
   administering an insulin-like growth factor 1 receptor (IGF-1R) inhibitor comprising an anti-IGF-1R antibody to said subject to directly inhibit IGF-1R expression and/or activity levels in the heart of said subject;
   thereby treating heart failure in said subject.

* * * * *